US008846639B2

(12) United States Patent
Swayze et al.

(10) Patent No.: US 8,846,639 B2
(45) Date of Patent: Sep. 30, 2014

(54) OLIGOMERIC COMPOUNDS COMPRISING BICYCLIC NUCLEOSIDES AND HAVING REDUCED TOXICITY

(75) Inventors: Eric E. Swayze, Encinitas, CA (US); Andrew M. Siwkowski, Carlsbad, CA (US)

(73) Assignee: Isis Pharmaceutical, Inc., Carlsbad, CA (US)

( * ) Notice: Subject to any disclaimer, the term of this patent is extended or adjusted under 35 U.S.C. 154(b) by 563 days.

(21) Appl. No.: 12/936,156

(22) PCT Filed: Apr. 3, 2009

(86) PCT No.: PCT/US2009/039557
§ 371 (c)(1),
(2), (4) Date: Jan. 14, 2011

(87) PCT Pub. No.: WO2009/124295
PCT Pub. Date: Oct. 8, 2009

(65) Prior Publication Data
US 2011/0112170 A1    May 12, 2011

Related U.S. Application Data

(60) Provisional application No. 61/042,619, filed on Apr. 4, 2008.

(51) Int. Cl.
*A01N 43/04* (2006.01)
*A61K 31/70* (2006.01)

(52) U.S. Cl.
USPC ............... 514/51; 514/42; 514/43; 514/44 R; 514/44 A; 514/49; 514/50

(58) Field of Classification Search
None
See application file for complete search history.

(56) References Cited

U.S. PATENT DOCUMENTS

| | | | |
|---|---|---|---|
| 3,687,808 A | 8/1972 | Merigan et al. |
| 4,469,863 A | 9/1984 | Ts'o et al. |
| 4,587,044 A | 5/1986 | Miller et al. |
| 4,605,735 A | 8/1986 | Miyoshi et al. |
| 4,667,025 A | 5/1987 | Miyoshi et al. |
| 4,762,779 A | 8/1988 | Snitman |
| 4,789,737 A | 12/1988 | Miyoshi et al. |
| 4,824,941 A | 4/1989 | Gordon et al. |
| 4,829,979 A | 5/1989 | Moir |
| 4,835,263 A | 5/1989 | Nguyen et al. |
| 4,845,205 A | 7/1989 | Huynh Dinh et al. |
| 4,876,335 A | 10/1989 | Yamane et al. |
| 4,904,582 A | 2/1990 | Tullis |
| 4,948,882 A | 8/1990 | Ruth |
| 4,958,013 A | 9/1990 | Letsinger |
| 4,981,957 A | 1/1991 | Lebleu et al. |
| 5,023,243 A | 6/1991 | Tullis |
| 5,082,830 A | 1/1992 | Brakel et al. |
| 5,109,124 A | 4/1992 | Ramachandran et al. |
| 5,112,963 A | 5/1992 | Pieles et al. |
| 5,118,800 A | 6/1992 | Smith et al. |
| 5,118,802 A | 6/1992 | Smith et al. |
| 5,130,302 A | 7/1992 | Spielvogel et al. |
| 5,134,066 A | 7/1992 | Rogers et al. |
| 5,138,045 A | 8/1992 | Cook et al. |
| 5,175,273 A | 12/1992 | Bischofberger et al. |
| 5,177,198 A | 1/1993 | Spielvogel et al. |
| 5,214,136 A | 5/1993 | Lin et al. |
| 5,218,105 A | 6/1993 | Cook et al. |
| 5,223,618 A | 6/1993 | Cook et al. |
| 5,245,022 A | 9/1993 | Weis et al. |
| 5,254,469 A | 10/1993 | Warren, III et al. |
| 5,256,775 A | 10/1993 | Froehler |
| 5,258,506 A | 11/1993 | Urdea et al. |
| 5,262,536 A | 11/1993 | Hobbs, Jr. |
| 5,264,562 A | 11/1993 | Matteucci |
| 5,264,564 A | 11/1993 | Matteucci |
| 5,272,250 A | 12/1993 | Spielvogel et al. |
| 5,292,873 A | 3/1994 | Rokita et al. |
| 5,317,098 A | 5/1994 | Shizuya et al. |
| 5,319,080 A | 6/1994 | Leumann |
| 5,359,044 A | 10/1994 | Cook et al. |
| 5,366,878 A | 11/1994 | Pederson et al. |
| 5,367,066 A | 11/1994 | Urdea et al. |
| 5,371,241 A | 12/1994 | Brush |
| 5,378,825 A | 1/1995 | Cook et al. |
| 5,386,023 A | 1/1995 | Sanghvi et al. |

(Continued)

FOREIGN PATENT DOCUMENTS

WO    WO 94/02499    2/1994
WO    WO 94/17093    8/1994

(Continued)

OTHER PUBLICATIONS

Altmann et al., "Second-generation antisense oligonucleotides: structure-activity relationships and the design of improved signal-transduction inhibitors" Biochem. Soc. Trans. (1996) 24:630-637.
Altmann et al., "Second Generation of Antisense Oligonucleotides: From Nuclease Resistance to Biological Efficacy in Animals" Chimia (1996) 50(4):168-176.
Altmann et al., "Second Generation Antisense Oligonucleotides—Inhibition of PKC-a and c-RAF Kinase Expression by Chimeric Oligonucleotides Incorporating 6'-Substituted Carbocyclic Nucleosides and 2'—O—Ethylene Glycol Substituted Ribonucleosides" Nucleosides Nucleotides (1997) 16(7-9):917-926.
Ausubel et al., Current Protocols in Molecular Biology, vol. 2, pp. 11.12.1-11.12.9, John Wiley & Sons, 1997.

(Continued)

*Primary Examiner* — Patrick Lewis
(74) *Attorney, Agent, or Firm* — Casimir Jones, S.C.

(57) ABSTRACT

In certain embodiments, the present invention provides oligomeric compounds having favorable toxicity profiles and therapeutic indexes. Compounds of the present invention comprise bicyclic nucleosides. Certain such bicyclic nucleosides are pyrimidines that do not include a methyl group at the 5-carbon. Oligomeric compounds comprising such nucleosides are less toxic than compounds comprising bicyclic nucleosides that do include a methyl group at the 5-carbon. In certain embodiments, the present invention provides methods of preparing and using such compounds.

15 Claims, No Drawings

(56) References Cited

U.S. PATENT DOCUMENTS

| | | |
|---|---|---|
| 5,391,723 A | 2/1995 | Priest |
| 5,393,878 A | 2/1995 | Leumann |
| 5,414,077 A | 5/1995 | Lin et al. |
| 5,416,203 A | 5/1995 | Letsinger |
| 5,432,272 A | 7/1995 | Benner |
| 5,434,257 A | 7/1995 | Matteucci et al. |
| 5,451,463 A | 9/1995 | Nelson et al. |
| 5,457,187 A | 10/1995 | Gmeiner et al. |
| 5,459,225 A | 10/1995 | Kuze et al. |
| 5,466,137 A | 11/1995 | Bierlein et al. |
| 5,466,786 A | 11/1995 | Buhr et al. |
| 5,476,925 A | 12/1995 | Letsinger et al. |
| 5,484,908 A | 1/1996 | Froehler et al. |
| 5,486,603 A | 1/1996 | Buhr |
| 5,489,677 A | 2/1996 | Sanghvi et al. |
| 5,502,117 A | 3/1996 | Wood |
| 5,508,270 A | 4/1996 | Baxter et al. |
| 5,510,475 A | 4/1996 | Agrawal et al. |
| 5,512,439 A | 4/1996 | Hornes et al. |
| 5,512,667 A | 4/1996 | Reed et al. |
| 5,514,785 A | 5/1996 | Van Ness et al. |
| 5,519,134 A | 5/1996 | Acevedo et al. |
| 5,525,465 A | 6/1996 | Haralambidis et al. |
| 5,525,711 A | 6/1996 | Hawkins et al. |
| 5,541,313 A | 7/1996 | Ruth |
| 5,545,730 A | 8/1996 | Urdea et al. |
| 5,552,538 A | 9/1996 | Urdea et al. |
| 5,552,540 A | 9/1996 | Haralambidis |
| 5,565,552 A | 10/1996 | Magda et al. |
| 5,567,810 A | 10/1996 | Weis et al. |
| 5,567,811 A | 10/1996 | Misiura et al. |
| 5,574,142 A | 11/1996 | Meyer, Jr. et al. |
| 5,576,427 A | 11/1996 | Cook et al. |
| 5,578,717 A | 11/1996 | Urdea et al. |
| 5,578,718 A | 11/1996 | Cook et al. |
| 5,580,731 A | 12/1996 | Chang et al. |
| 5,585,481 A | 12/1996 | Arnold, Jr. et al. |
| 5,587,371 A | 12/1996 | Sessler et al. |
| 5,587,469 A | 12/1996 | Cook et al. |
| 5,591,584 A | 1/1997 | Chang et al. |
| 5,591,722 A | 1/1997 | Montgomery et al. |
| 5,594,121 A | 1/1997 | Froehler et al. |
| 5,595,726 A | 1/1997 | Magda et al. |
| 5,596,091 A | 1/1997 | Switzer |
| 5,597,696 A | 1/1997 | Linn et al. |
| 5,597,909 A | 1/1997 | Urdea et al. |
| 5,599,923 A | 2/1997 | Sessler et al. |
| 5,599,928 A | 2/1997 | Hemmi et al. |
| 5,602,240 A | 2/1997 | De Mesmaeker et al. |
| 5,608,046 A | 3/1997 | Cook et al. |
| 5,610,289 A | 3/1997 | Cook et al. |
| 5,610,300 A | 3/1997 | Altmann et al. |
| 5,614,617 A | 3/1997 | Cook et al. |
| 5,625,050 A | 4/1997 | Beaton et al. |
| 5,627,053 A | 5/1997 | Usman et al. |
| 5,639,873 A | 6/1997 | Barascut et al. |
| 5,645,985 A | 7/1997 | Froehler et al. |
| 5,646,265 A | 7/1997 | McGee |
| 5,646,269 A | 7/1997 | Matteucci et al. |
| 5,658,873 A | 8/1997 | Bertsch-Frank et al. |
| 5,670,633 A | 9/1997 | Cook et al. |
| 5,681,941 A | 10/1997 | Cook et al. |
| 5,688,941 A | 11/1997 | Cook et al. |
| 5,700,920 A | 12/1997 | Altmann et al. |
| 5,750,692 A | 5/1998 | Cook et al. |
| 5,763,588 A | 6/1998 | Matteucci et al. |
| 5,792,747 A | 8/1998 | Schally et al. |
| 5,830,653 A | 11/1998 | Froehler et al. |
| 6,005,096 A | 12/1999 | Matteucci et al. |
| 6,007,992 A | 12/1999 | Lin et al. |
| 6,028,183 A | 2/2000 | Lin et al. |
| 6,172,209 B1 | 1/2001 | Manoharan et al. |
| 6,268,490 B1 | 7/2001 | Imanishi et al. |
| 6,271,358 B1 | 8/2001 | Manoharan et al. |
| 6,426,220 B1 | 7/2002 | Bennett et al. |
| 6,426,221 B1 | 7/2002 | Ward et al. |
| 6,525,191 B1 | 2/2003 | Ramasamy |
| 6,531,584 B1 | 3/2003 | Cook et al. |
| 6,600,032 B1 | 7/2003 | Manoharan et al. |
| 6,617,162 B2 | 9/2003 | Dobie et al. |
| 6,670,461 B1 | 12/2003 | Wengel et al. |
| 6,699,677 B1 | 3/2004 | Schall et al. |
| 6,770,748 B2 | 8/2004 | Imanishi et al. |
| 6,794,499 B2 | 9/2004 | Wengel et al. |
| 7,034,133 B2 | 4/2006 | Wengel et al. |
| 7,053,207 B2 | 5/2006 | Wengel |
| 2003/0158403 A1 | 8/2003 | Manoharan et al. |
| 2003/0175906 A1 | 9/2003 | Manoharan et al. |
| 2003/0207804 A1 | 11/2003 | Manoharan et al. |
| 2005/0020525 A1 | 1/2005 | McSwiggen et al. |

FOREIGN PATENT DOCUMENTS

| | | |
|---|---|---|
| WO | WO 97/26270 | 7/1997 |
| WO | WO 98/39352 | 9/1998 |
| WO | WO 99/14226 | 3/1999 |
| WO | WO 01/48190 | 7/2001 |
| WO | WO 02/36743 | 5/2002 |
| WO | WO 03/004602 | 1/2003 |
| WO | WO 2004/046160 | 6/2004 |
| WO | WO 2004/106356 | 12/2004 |
| WO | WO 2005/021570 | 3/2005 |
| WO | WO 2007/027894 | 3/2007 |
| WO | WO 2007/090071 | 8/2007 |
| WO | WO 2007/131237 | 11/2007 |
| WO | WO 2007/134181 | 11/2007 |
| WO | WO 2007/146511 | 12/2007 |
| WO | WO 2008/049085 | 4/2008 |
| WO | WO 2008/068284 | 6/2008 |
| WO | WO 2009/043354 | 4/2009 |

OTHER PUBLICATIONS

Baker et al., "2'—O—(2-Methoxy)ethyl-modified Anti-intercellular Adhesion Molecule 1 (ICAM-1) Oligonucleotides Selectively Increase the ICAM-1 mRNA Level and Inhibit Formation of the ICAM-1 Translation Initiation Complex in Human Umbilical Vein Endothelial Cells" J. Biol. Chem. (1997) 272(18):11944-12000.

Barany et al., "A New Amino Protecting Group Removable by Reduction. Chemistry of the Dithiasuccinoyl (Dts) Function" J. Am. Chem. Soc. (1977) 99:7363.

Barany et al., "Kinetics and Mechanism of the Thiolytic Removal of the Dithiasuccinoyl (Dts) Amino Protecting Group" J. Am. Chem. Soc. (1980) 102(9):3084.

Beaucage et al., "The Functionalization of Oligonucleotides Via Phosphoramidite Derivatives" Tetrahedron (1993) 49(10):1925-1963.

Braasch et al., "Locked nucleic acid (LNA): fine-tuning the recognition of DNA and RNA" Chem. Biol. (2001) 8:1-7.

Chiang et al., "Antisense Oligonucleotides Inhibit Intercellular Adhesion Molecule 1 Expression by Two Distinct Mechanisms" J. Biol. Chem. (1991) 266(27):18162-18171.

Crooke et al., "Pharmacokinetic Properties of Several Novel Oligonucleotide Analogs in Mice" J. Pharmacol. Exp. Ther. (1996) 277(2):923-937.

Elayadi et al., "Application of PNA and LNA oligomers to chemotherapy" Curr. Opinions Invens. Drugs (2001) 2:558-561.

Englisch et al., "Chemically Modified Oligonucleotides as Probes and Inhibitors" Angewandte Chemie (1991)30:613.

Flanagan et al., "A cytosine analog that confers enhanced potency to antisense oligonucleotides" PNAS (1999) 96:3513-3518.

Freier et al., "The ups and downs of nucleic acid duplex stability: structure-stability studies on chemically-modified DNA:RNA duplexes" Nucleic Acids Research (1997) 25(22):4429-4443.

Frieden et al., "Expanding the design horizon of antisense oligonucleotides with alpha-L-LNA" Nucleic Acids Research (2003) 31(21):6365-6372.

Gait et al., Applications of Chemically Synthesized RNA in RNA: Protein Interactions, ed. Smith, 1998, 1-36.

Gallo et al., "2'—C—Methyluridine phosphoramidite: a new building block for the preparation of RNA analogues carrying the 2'-hydroxyl group" Tetrahedron (2001) 57:5707-5713.

(56) References Cited

OTHER PUBLICATIONS

Greene & Wuts, Protective Groups in Organic Synthesis, 2nd edition, John Wiley & Sons, New York, 1991.
Henry et al., "Chemically Modified Oligonucleotides Exhibit Decreased Immune Stimulation in Mice" J. Pharmacology and Experimental Therapeutics (2000) 292(2):468-479.
Jones et al., "RNA Quantitation by Fluorescence-Based Solution Assay: RiboGreen Reagent Chacaterization" Analytical Biochemistry (1998) 265:368-374.
Kabanov et al., "A new class of antivirals: antisense oligonucleotides combined with a hydrophobic substituent effectively inhibit influenza virus reproduction and synthesis of virus-specific proteins in MDCK cells" FEBS Lett. (1990) 259:327-330.
Koshkin et al., "LNA (Locked Nucleic Acids): Synthesis of the Adenine, Cytosine, Guanine, 5-Methylcytosine, Thymine and Uracil Bicyclonucleoside Monomers, Oligomerisation, and Unprecedented Nucleic Acid Recognition" Tetrahedron (1998) 54:3607-3630.
Kroschwitz, the Concise Encyclopedia of Polymer Science and Engineering, pp. 858-859, John Wiley & Sons, 1990.
Kumar et al., "The First Analogues of LNA (Locked Nucleic Acids): Phosphorothioate-LNA and 2'-ThioLNA" Bioorg. Med. Chem. Lett. (1998) 8:2219-2222.
Kurchavov et al., "A New Phosphoramidite Reagent for the Incorporation of Diazaphenoxazinone Nucleoside with Enhanced Base-Pairing Properties into Oligodeoxynucleotides" Nucleosides and Nucleotides (1997) 16(10 & 11):1837-1846.
Letsinger et al., "Cholesteryl-conjugated oligonucleotides: Synthesis, properties, and activity as inhibitors of replication of human immunodeficiency virus in cell culture" PNAS (1989) 86:6553-6556.
Lin et al., "Tricyclic 2'-Deoxycytidine Analogs: Synthesis and Incorporation into Oligodeoxynucleotides Which Have Enhanced Binding to Complementary RNA" J. Am. Chem. Soc. (1995) 117:3873-3874.
Lin et al., "A Cytosine Analogue Capable of Clamp-Like Binding to a Guanine in Helical Nucleic Acids" J. Am. Chem. Soc. (1998) 120:8531-8532.
Manoharan et al., "Chemical Modifications to Improve Uptake and Bioavailability of Antisense Oligonucleotides" Ann. N.Y. Acad. Sci. (1992) 660:306-309.
Manoharan et al., "Cholic Acid-Oligonucleotide Conjugates for Antisense Applications" Bioorg. Med. Chem. Lett. (1994) 4(8):1053-1060.
Manoharan et al., "Oligonucleotide Conjugates: Alteration of the Pharmacokinetic Properties of Antisense Agents" Nucleosides & Nucleotides (1995) 14(3-5):969-973.
Manoharan et al., "Lipidic Nucleic Acids" Tetrahedron Lett. (1995) 36(21):3651-3654.
Manoharan et al., "Introduction of a Lipophilic Thioether Tether in the Minor Groove of Nucleic Acids for Antisense Applications" Bioorg. Med. Chem. Lett. (1993) 3(12):2765-2770.
Martin, "Ein neuer Zugang zu 2'—O—Alkylribonucleosiden und Eigenschaften deren Oligonucleotide" Helv. Chim. Acta (1995) 78:486-504.
Mishra et al., "Improved leishmanicidal effect of phosphorothioate antisense oligonuceotides by LDL-mediated delivery" Biochim. Biophys. Acta (1995) 1264:229-237.

Morita et al., "Synthesis and Properties of 2'—O,4'—C—Ethylene-Bridged Nucleic Acids (ENA) as Effective Antisense Oligonucleotides" Bioorganic & Medicinal Chemistry (2003) 11:2211-2226.
Oberhauser et al., "Effective incorporation of 2'—O—methyl-oligoribonucleotides into liposomes and enhanced cell association through modification with thiocholesterol" Nucl. Acids Res. (1992) 20(3):533-538.
Orum et al., "Locked nucleic acids: A promising molecular family for gene-function analysis and antisense drug development" Curr. Opinion Mol. Ther. (2001) 3:239-243.
Saison-Behmoaras et al., "Short modified antisense oligonucleotides directed against Ha-ras point mutation induce selective cleavage of the RNA and inhibit T24 cells proliferation" EMBO J. (1991) 10(5):1111-1118.
Sambrook et al., "Molecular Cloning, A Laboratory Manual" 2nd Edition, Cold Spring Harbor Laboratory Press, 1989.
Sanghvi, Antisense Research and Applications, Chapter 15, Crooke & Lebleu ed., CRC Press, 1993.
Sanghvi & Cook, Carbohydrate Modifications in Antisense Research, American Chemical Society, Washington, D.C., 1994.
Scaringe, "RNA Oligonucleotide Synthesis via 5'-Silyl-2'-Orthoester Chemistry" Methods (2001) 23:206-217.
Shea et al., "Synthesis, hybridization properties and antiviral activity of lipid-oligodeoxynucleotide conjugates" Nucl. Acids Res. (1990) 18(13):3777-3783.
Singh et al., "LNA (locked nucleic acids): synthesis and high-affinity nucleic acid recognition" Chem. Commun. (1998) 4:455-456.
Singh et al., "Synthesis 2'-Amino-LNA: A Novel Conformationally Restricted High-Affinity Oligonucleotide Analogue with a Handle" J. Org. Chem. (1998) 63:10035-10039.
Skerra, Phosphorothioate primers improve the amplification of DNA sequences by DNA polymerase with proofreading activity Nucleic Acids Research (1992) 20(14):3551-3554.
Srivastava et al., "Five- and Six-Membered Conformationally Locked 2',4'-Carbocyclic ribo-Thymidines: Synthesis, Structure, and Biochemical Studies" J. Am. Chem. Soc. (2007) 129(26): 8362-8379.
Svinarchuk et al., "Inhibition of HIV proliferation in MT-4 cells by antisense oligonucleotide conjugated to lipophilic groups" Biochimie (1993) 75:49-54.
Swayze & Bhat, The Medicinal Chemistry of Oligonucleotides in Antisense Drug Technology 2nd edition, Chapter 6, pp. 143-182 (Crooke, S.T., ed., 2008).
Swayze et al., "Antisense oligonucleotides containing locked nucleic acid improve potency but cause significant hepatotoxicity in animals" Nucleic Acid Research (2007) 35(2):687-700.
Wahlestedt et al., "Potent and nontoxic antisense oligonucleotides containing locked nucleic acids" PNAS (2000) 97:5633-5638.
Wang et al., "Synthesis and binding property of an oligonucleotide containing tetrafluorophenoxazine" Tetrahedron Lett. (1998) 39:8385-8388.
International Search Report for application PCT/US06/11478 dated Nov. 6, 2006.
International Search Report for application PCT/US09/039557 dated Nov. 9, 2009.

SEQUENCE LISTING

<160> NUMBER OF SEQ ID NOS: 6

<210> SEQ ID NO 1
<211> LENGTH: 3160
<212> TYPE: DNA
<213> ORGANISM: Homo sapiens
<220> FEATURE:
<221> NAME/KEY: CDS
<222> LOCATION: (1035)..(2246)

<400> SEQUENCE: 1
cctcccctcg cccggcgcgg tcccgtccgc ctctcgctcg cctcccgcct cccctcggtc    60

```
ttccgaggcg cccgggctcc cggcgcggcg gcggaggggg cgggcaggcc ggcgggcggt      120
gatgtggcag gactctttat gcgctgcggc aggatacgcg ctcggcgctg ggacgcgact      180
gcgctcagtt ctctcctctc ggaagctgca gccatgatgg aagtttgaga gttgagccgc      240
tgtgaggcga ggccgggctc aggcgaggga gatgagagac ggcggcggcc gcggcccgga      300
gcccctctca gcgcctgtga gcagccgcgg gggcagcgcc ctcggggagc cggccggcct      360
gcggcggcgc cagcggcggc gtttctcgcc tcctcttcgt cttttctaac cgtgcagcct      420
cttcctcggc ttctcctgaa agggaaggtg gaagccgtgg gctcgggcgg gagccggctg      480
aggcgcggcg gcgcggcgg cggcacctcc cgctcctgga gcgggggga gaagcggcgg        540
cggcggcggc cgcggcggct gcagctccag ggaggggtc tgagtcgcct gtcaccattt       600
ccagggctgg gaacgccgga gagttggtct ctcccttct actgcctcca acacggcggc       660
ggcggcggcg gcacatccag ggacccgggc cggttttaaa cctcccgtcc gccgccgccg      720
cacccccgt ggcccgggct ccggaggccg ccggcggagg cagccgttcg gaggattatt       780
cgtcttctcc ccattccgct gccgccgctg ccaggcctct ggctgctgag gagaagcagg      840
cccagtcgct gcaaccatcc agcagccgcc gcagcagcca ttacccggct gcggtccaga      900
gccaagcggc ggcagagcga ggggcatcag ctaccgccaa gtccagagcc atttccatcc      960
tgcagaagaa gccccgccac cagcagcttc tgccatctct ctcctccttt ttcttcagcc     1020
```
acaggctccc agac atg aca gcc atc atc aaa gag atc gtt agc aga aac   1070
                Met Thr Ala Ile Ile Lys Glu Ile Val Ser Arg Asn
                 1               5                  10 aaa agg aga tat caa gag gat gga ttc gac tta gac ttg acc tat att   1118
Lys Arg Arg Tyr Gln Glu Asp Gly Phe Asp Leu Asp Leu Thr Tyr Ile
         15                  20                  25 tat cca aac att att gct atg gga ttt cct gca gaa aga ctt gaa ggc   1166
Tyr Pro Asn Ile Ile Ala Met Gly Phe Pro Ala Glu Arg Leu Glu Gly
     30                  35                  40 gta tac agg aac aat att gat gat gta gta agg ttt ttg gat tca aag   1214
Val Tyr Arg Asn Asn Ile Asp Asp Val Val Arg Phe Leu Asp Ser Lys
45                  50                  55                  60 cat aaa aac cat tac aag ata tac aat ctt tgt gct gaa aga cat tat   1262
His Lys Asn His Tyr Lys Ile Tyr Asn Leu Cys Ala Glu Arg His Tyr
                 65                  70                  75 gac acc gcc aaa ttt aat tgc aga gtt gca caa tat cct ttt gaa gac   1310
Asp Thr Ala Lys Phe Asn Cys Arg Val Ala Gln Tyr Pro Phe Glu Asp
             80                  85                  90 cat aac cca cca cag cta gaa ctt atc aaa ccc ttt tgt gaa gat ctt   1358
His Asn Pro Pro Gln Leu Glu Leu Ile Lys Pro Phe Cys Glu Asp Leu
         95                 100                 105 gac caa tgg cta agt gaa gat gac aat cat gtt gca gca att cac tgt   1406
Asp Gln Trp Leu Ser Glu Asp Asp Asn His Val Ala Ala Ile His Cys
    110                 115                 120 aaa gct gga aag gga cga act ggt gta atg ata tgt gca tat tta tta   1454
Lys Ala Gly Lys Gly Arg Thr Gly Val Met Ile Cys Ala Tyr Leu Leu
125                 130                 135                 140 cat cgg ggc aaa ttt tta aag gca caa gag gcc cta gat ttc tat ggg   1502
His Arg Gly Lys Phe Leu Lys Ala Gln Glu Ala Leu Asp Phe Tyr Gly
                145                 150                 155 gaa gta agg acc aga gac aaa aag gga gta act att ccc agt cag agg   1550
Glu Val Arg Thr Arg Asp Lys Lys Gly Val Thr Ile Pro Ser Gln Arg
            160                 165                 170 cgc tat gtg tat tat tat agc tac ctg tta aag aat cat ctg gat tat   1598
Arg Tyr Val Tyr Tyr Tyr Ser Tyr Leu Leu Lys Asn His Leu Asp Tyr

```
                175                 180                 185
aga cca gtg gca ctg ttg ttt cac aag atg atg ttt gaa act att cca      1646
Arg Pro Val Ala Leu Leu Phe His Lys Met Met Phe Glu Thr Ile Pro
    190                 195                 200 atg ttc agt ggc gga act tgc aat cct cag ttt gtg gtc tgc cag cta      1694
Met Phe Ser Gly Gly Thr Cys Asn Pro Gln Phe Val Val Cys Gln Leu
205                 210                 215                 220 aag gtg aag ata tat tcc tcc aat tca ggc ccc aca cga cgg gaa gac      1742
Lys Val Lys Ile Tyr Ser Ser Asn Ser Gly Pro Thr Arg Arg Glu Asp
                    225                 230                 235 aag ttc atg tac ttt gag ttc cct cag ccg tta cct gtg tgt ggt gat      1790
Lys Phe Met Tyr Phe Glu Phe Pro Gln Pro Leu Pro Val Cys Gly Asp
                240                 245                 250 atc aaa gta gag ttc ttc cac aaa cag aac aag atg cta aaa aag gac      1838
Ile Lys Val Glu Phe Phe His Lys Gln Asn Lys Met Leu Lys Lys Asp
            255                 260                 265 aaa atg ttt cac ttt tgg gta aat aca ttc ttc ata cca gga cca gag      1886
Lys Met Phe His Phe Trp Val Asn Thr Phe Phe Ile Pro Gly Pro Glu
270                 275                 280 gaa acc tca gaa aaa gta gaa aat gga agt cta tgt gat caa gaa atc      1934
Glu Thr Ser Glu Lys Val Glu Asn Gly Ser Leu Cys Asp Gln Glu Ile
285                 290                 295                 300 gat agc att tgc agt ata gag cgt gca gat aat gac aag gaa tat cta      1982
Asp Ser Ile Cys Ser Ile Glu Arg Ala Asp Asn Asp Lys Glu Tyr Leu
                305                 310                 315 gta ctt act tta aca aaa aat gat ctt gac aaa gca aat aaa gac aaa      2030
Val Leu Thr Leu Thr Lys Asn Asp Leu Asp Lys Ala Asn Lys Asp Lys
            320                 325                 330 gcc aac cga tac ttt tct cca aat ttt aag gtg aag ctg tac ttc aca      2078
Ala Asn Arg Tyr Phe Ser Pro Asn Phe Lys Val Lys Leu Tyr Phe Thr
            335                 340                 345 aaa aca gta gag gag ccg tca aat cca gag gct agc agt tca act tct      2126
Lys Thr Val Glu Glu Pro Ser Asn Pro Glu Ala Ser Ser Ser Thr Ser
350                 355                 360 gta aca cca gat gtt agt gac aat gaa cct gat cat tat aga tat tct      2174
Val Thr Pro Asp Val Ser Asp Asn Glu Pro Asp His Tyr Arg Tyr Ser
365                 370                 375                 380 gac acc act gac tct gat cca gag aat gaa cct ttt gat gaa gat cag      2222
Asp Thr Thr Asp Ser Asp Pro Glu Asn Glu Pro Phe Asp Glu Asp Gln
                385                 390                 395 cat aca caa att aca aaa gtc tga atttttttt atcaagaggg ataaacacc       2276
His Thr Gln Ile Thr Lys Val
                400 atgaaaataa acttgaataa actgaaaatg gacctttttt ttttaatgg caataggaca     2336 ttgtgtcaga ttaccagtta taggaacaat tctcttttcc tgaccaatct tgttttaccc    2396 tatacatcca cagggttttg acacttgttg tccagttgaa aaaaggttgt gtagctgtgt    2456 catgtatata cctttttgtg tcaaaaggac atttaaaatt caattaggat taataaagat    2516 ggcactttcc cgttttattc cagttttata aaaagtggag acagactgat gtgtatacgt    2576 aggaattttt tccttttgtg ttctgtcacc aactgaagtg gctaaagagc tttgtgatat    2636 actggttcac atcctacccc tttgcacttg tggcaacaga taagtttgca gttggctaag    2696 agaggtttcc gaaaggtttt gctaccattc taatgcatgt attcgggtta gggcaatgga    2756 ggggaatgct cagaaaggaa ataatttat gctggactct ggaccatata ccatctccag     2816 ctatttacac acaccttttct ttagcatgct acagttatta atctggacat tcgaggaatt   2876 ggccgctgtc actgcttgtt gtttgcgcat ttttttttaa agcatattgg tgctagaaaa    2936
```

```
ggcagctaaa ggaagtgaat ctgtattggg gtacaggaat gaaccttctg caacatctta    2996
agatccacaa atgaagggat ataaaaataa tgtcataggt aagaaacaca gcaacaatga    3056
cttaaccata taaatgtgga ggctatcaac aaagaatggg cttgaaacat tataaaaatt    3116
gacaatgatt tattaaatat gttttctcaa ttgtaaaaaa aaaa                     3160
```

```
<210> SEQ ID NO 2
<211> LENGTH: 26
<212> TYPE: DNA
<213> ORGANISM: Artificial sequence
<220> FEATURE:
<223> OTHER INFORMATION: Primer

<400> SEQUENCE: 2
aatggctaag tgaagatgac aatcat                                         26

<210> SEQ ID NO 3
<211> LENGTH: 25
<212> TYPE: DNA
<213> ORGANISM: Artificial sequence
<220> FEATURE:
<223> OTHER INFORMATION: Primer

<400> SEQUENCE: 3
tgcacatatc attacaccag ttcgt                                          25

<210> SEQ ID NO 4
<211> LENGTH: 30
<212> TYPE: DNA
<213> ORGANISM: Artificial sequence
<220> FEATURE:
<223> OTHER INFORMATION: Probe

<400> SEQUENCE: 4
ttgcagcaat tcactgtaaa gctggaaagg                                     30

<210> SEQ ID NO 5
<211> LENGTH: 14
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: 1, 2, 13, 14
<223> OTHER INFORMATION: Bases at these positions are RNA

<400> SEQUENCE: 5
cutagcactg gccu                                                      14

<210> SEQ ID NO 6
<211> LENGTH: 14
<212> TYPE: DNA
<213> ORGANISM: Artificial sequence
<220> FEATURE:
<223> OTHER INFORMATION: Synthetic oligonucleotide

<400> SEQUENCE: 6
cttagcactg gcct                                                      14
```

OLIGOMERIC COMPOUNDS COMPRISING BICYCLIC NUCLEOSIDES AND HAVING REDUCED TOXICITY

This application is the national phase entry pursuant to 35 U.S.C. §371 of International Application No. PCT/US2009/039557, which has the international filing date of Apr. 3, 2009, and which claims priority to U.S. Provisional Application Ser. No. 61/042,619, filed Apr. 4, 2008, all of which are incorporated herein by reference in their entireties.

FIELD OF THE INVENTION

The present invention provides compounds and methods for modulating nucleic acids and proteins.

SEQUENCE LISTING

The present application is being filed along with a Sequence Listing in electronic format. The Sequence Listing is provided as a file entitled BIOL0080SEQ.txt, created on Apr. 3, 2009 which is 8 Kb in size. The information in the electronic format of the sequence listing is incorporated herein by reference in its entirety.

BACKGROUND OF THE INVENTION

Antisense compounds have been used to modulate target nucleic acids. Antisense compounds comprising a variety of modifications and motifs have been reported. Certain oligonucleotides comprising nucleosides having bicyclic sugar moieties have been reported. In certain instances, such compounds are useful as research tools and as therapeutic agents. In certain instances antisense compounds have been shown to modulate protein expression by altering splicing of a pre-mRNA, by arresting translation and/or by interrupting polyadenylation of a pre-mRNA.

SUMMARY OF THE INVENTION

In certain embodiments, the present invention provides an oligonucleotide consisting of 8-26 linked nucleosides wherein at least one nucleoside is a bicyclic nucleoside comprising a bicyclic sugar moiety and a nucleobase wherein the nucleobase is selected from among Formula I and Formula II:

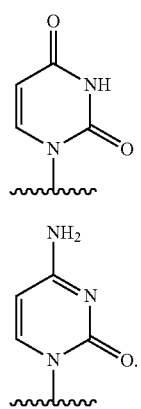

In certain such embodiments, the oligonucleotide has at least one bicyclic nucleoside that is a 4'-2' bridged bicyclic nucleoside. In certain such embodiments, such oligonucleotides have at least one bicyclic nucleoside has a bicyclic sugar moiety having Formula III:

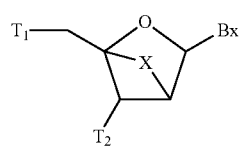

wherein independently for each of the at least one bicyclic nucleoside of formula III:

X is selected from among: 4'-$(CR_1R_2)_n$—Y-2';

wherein each $R_1$ and each $R_2$ is independently selected from among: hydrogen, a halogen, an optionally substituted $C_1$-$C_6$ alkyl, an optionally substituted $C_2$-$C_6$ alkenyl, an optionally substituted $C_2$-$C_6$ alkynyl, an optionally substituted heteroalkyl, an optionally substituted heteroalkenyl, and an optionally substituted heteroalkynyl;

Y is selected from among $CR_1R_2$, O, N(J), and S;

$T_1$ and $T_2$ are each, independently, an internucleoside linking group linking the bicyclic nucleoside to the oligonucleotide or one of $T_1$ and $T_2$ is an internucleoside linking group linking the bicyclic nucleoside to the oligonucleotide and the other of $T_1$ and $T_2$ is hydroxyl, a protected hydroxyl, a linked conjugate group or a 5' or 3'-terminal group;

n is from 1 to 3;

J is hydrogen, a halogen, an optionally substituted $C_1$-$C_5$ alkyl, an optionally substituted $C_1$-$C_5$ alkenyl, an optionally substituted $C_1$-$C_5$ alkynyl, an optionally substituted heteroalkyl, an optionally substituted heteroalkenyl, or an optionally substituted heteroalkynyl; and Bx is the heterocyclic base moiety of Formula I or Formula II.

In certain such embodiments X is selected from among: 4'-$CH_2$O-2', 4'-$CH(CH_3)$O-2', and 4'-$CH_2CH_2$O-2'. In certain embodiments, X is 4'-$CH_2$O-2' or 4'-$CH_2CH_2$O-2'. In certain embodiments, X is 4'-$CH_2CH_2$O-2'. In certain embodiments, X is 4'-$CH_2$O-2'.

In any of such embodiments, the bicyclic nucleoside may be in the α-L configuration or in the β-D configuration. In certain embodiments, the bicyclic nucleoside has the configuration:

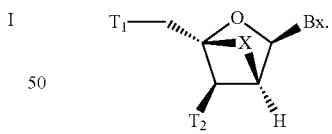

In certain embodiments, such oligonucleotides do not comprise any 5-methyl pyrimidine bicyclic nucleosides.

In certain embodiments, each nucleoside of an oligonucleotide of the present invention is a bicyclic nucleoside. In certain such embodiments, each nucleoside comprises the same bicyclic sugar moiety. In certain embodiments at least two nucleosides comprise bicyclic sugar moieties that are different from one another.

In certain embodiments, oligonucleotides of the present invention comprise at least one non-bicyclic nucleoside. Certain such oligonucleotides comprise at least one modified non-bicyclic nucleoside. In certain such embodiments, at least one modified nucleoside comprises at least one modified non-bicyclic nucleoside selected from among: 2'-O—

(CH$_2$)$_2$—OCH$_3$, 2'-OCH$_3$, and 2'-F. In certain embodiments, oligonucleotides of the present invention comprise at least one unmodified nucleoside, such as a ribonucleoside and/or a deoxyribonucleoside.

In certain embodiments, oligonucleotides of the present invention comprise two or more bicyclic nucleosides having a base moiety of Formula I or I and a sugar moiety of Formula III. In certain such embodiments, the two or more bicyclic nucleosides all comprise the same bicyclic sugar moiety. In certain embodiments, at least two of the two or more bicyclic nucleosides comprise bicyclic sugar moieties that are different from one another.

In certain embodiments, oligonucleotides of the present invention consist of 8-10 linked nucleosides. In certain embodiments, oligonucleotides of the present invention consist of 8-10 linked nucleosides. In certain embodiments, oligonucleotides of the present invention consist of 10-12 linked nucleosides. In certain embodiments, oligonucleotides of the present invention consist of 12-14 linked nucleosides. In certain embodiments, oligonucleotides of the present invention consist of 14-16 linked nucleosides. In certain embodiments, oligonucleotides of the present invention consist of 16-18 linked nucleosides. In certain embodiments, oligonucleotides of the present invention consist of 18-20 linked nucleosides. In certain embodiments, oligonucleotides of the present invention consist of 20-22 linked nucleosides. In certain embodiments, oligonucleotides of the present invention consist of 22-24 linked nucleosides. In certain embodiments, oligonucleotides of the present invention consist of 24-26 linked nucleosides. In certain embodiments, oligonucleotides of the present invention consist of 11-18 linked nucleosides.

In certain embodiments, oligonucleotides of the present invention are gapmers. In certain such embodiments, such gapmers comprise at least one bicyclic nucleoside of Formula III in at least one wing of the gapmer. In certain embodiments, such gapmers comprise at least one bicyclic nucleoside of Formula III in each wing of the gapmer. In certain embodiments, each nucleoside of each wing is a bicyclic nucleoside comprising a sugar moiety of Formula III. In certain embodiments, such gapmers consist of 1-6 nucleosides. In certain embodiments, such gapmers consist of 1-6 nucleosides. In certain embodiments, such gapmers consist of 1-5 nucleosides. In certain embodiments, such gapmers consist of 1-4 nucleosides. In certain embodiments, such gapmers consist of 1-3 nucleosides. In certain embodiments, such gapmers consist of 1-2 nucleosides.

In certain embodiments, such gapmers consist of 1 nucleoside.

In certain embodiments where an oligonucleotide of the present invention is a gapmer, the gap consists of 8-10 nucleosides. In certain embodiments where an oligonucleotide of the present invention is a gapmer, the gap consists of 10-12 nucleosides. In certain embodiments where an oligonucleotide of the present invention is a gapmer, the gap consists of 12-14 nucleosides. In certain embodiments where an oligonucleotide of the present invention is a gapmer, the gap consists of 14-16 nucleosides. In certain embodiments where an oligonucleotide of the present invention is a gapmer, the gap consists of 16-18 nucleosides. In certain embodiments where an oligonucleotide of the present invention is a gapmer, the gap consists of 18-20 nucleosides. In certain embodiments where an oligonucleotide of the present invention is a gapmer, the gap consists of 20-22 nucleosides. In certain embodiments where an oligonucleotide of the present invention is a gapmer, the gap consists of 8-9 nucleosides. In certain embodiments where an oligonucleotide of the present invention is a gapmer, the gap consists of 9-11 nucleosides.

In certain embodiments where an oligonucleotide of the present invention is a gapmer, the sugar modification of each nucleoside of one wing of the gapmer and the sugar modification of each nucleoside of the other wing of the gapmer are the same as one another. In certain embodiments where an oligonucleotide of the present invention is a gapmer, the sugar modification of each nucleoside of one wing of the gapmer and the sugar modification of each nucleoside of the other wing of the gapmer are different from one another.

In certain embodiments where an oligonucleotide of the present invention is a gapmer, the nucleosides of the gap are all unmodified nucleosides. In certain such embodiments, the nucleosides of the gap are all deoxyribonucleosides. In certain embodiments, the nucleosides of the gap are modified nucleosides.

In certain embodiments, oligonucleotide of the present invention have an alternating motif wherein regions of nucleosides having a sugar moiety of Formula III alternate with differently modified nucleosides. In certain such embodiments, oligonucleotides have at least four, at least five, at least six, at least seven, at least eight, an least nine, at least ten, at least eleven, or at least twelve separate regions. In certain embodiments the separate regions alternate between nucleosides of one type of modification and nucleoside of a different type of modification. In certain embodiments, the regions alternate among three types of modifications. In certain embodiments, each region comprises modifications that are different from the modifications of any other region.

In certain embodiments, an oligonucleotide of the present invention comprises at least one modified internucleoside linkage. In certain such embodiments, at least one modified internucleoside linkage is a phosphorothioate internucleoside linkages.

In certain embodiments, an oligonucleotide of the present invention is an antisense compound. In certain such embodiments, the oligonucleotide is complementary to a target nucleic acid selected from among: target mRNA, target pre-mRNA, target microRNA, and a target non-coding RNA. In certain embodiments, the target nucleic acid is a mammalian target nucleic acid, including, but not limited to a human nucleic acid, including, but not limited to a human mRNA. In certain embodiments where an oligonucleotide of the present invention is an antisense compound, the oligonucleotide is at least 85%, 90%, 95%, 98%, or 100% complementary to a target nucleic acid.

In certain embodiments, an oligonucleotide of the present invention consisting of 8-26 linked nucleosides wherein at least four nucleosides are bicyclic nucleoside comprising a bicyclic sugar moiety and a nucleobase wherein none of the nucleobases of the at least four bicyclic nucleosides has the structure of Formula IV or Formula V:

IV

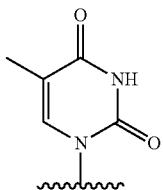

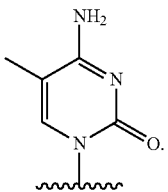

V

In certain embodiments, such oligonucleotides comprise at least five bicyclic nucleosides and none of the at least five bicyclic nucleosides has a nucleobase of structure IV or V. In certain embodiments, such oligonucleotides comprise at least six bicyclic nucleosides and none of the at least five bicyclic nucleosides has a nucleobase of structure IV or V. In certain embodiments, such oligonucleotides comprise at least seven bicyclic nucleosides and none of the at least five bicyclic nucleosides has a nucleobase of structure IV or V. In certain embodiments, such oligonucleotides comprise at least eight bicyclic nucleosides and none of the at least five bicyclic nucleosides has a nucleobase of structure IV or V. In certain embodiments, such oligonucleotides comprise at least nine bicyclic nucleosides and none of the at least five bicyclic nucleosides has a nucleobase of structure IV or V. In certain embodiments, such oligonucleotides comprise at least ten bicyclic nucleosides and none of the at least five bicyclic nucleosides has a nucleobase of structure IV or V. In certain such embodiments, at least one bicyclic nucleoside comprises a nucleobase selected from Formula I and Formula II. In certain embodiments, the sugar moiety of such nucleosides is a 4'-2' bridged bicyclic nucleoside. In certain embodiments, such nucleoside has formula III.

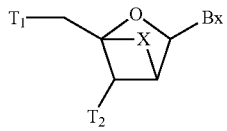

III wherein independently for each of the at least one bicyclic nucleoside of formula III:

X is selected from among: 4'-$(CR_1R_2)_n$—Y-2';

wherein each $R_1$ and each $R_2$ is independently selected from among: hydrogen, a halogen, an optionally substituted $C_1$-$C_6$ alkyl, an optionally substituted $C_2$-$C_6$ alkenyl, an optionally substituted $C_2$-$C_6$ alkynyl, an optionally substituted heteroalkyl, an optionally substituted heteroalkenyl, and an optionally substituted heteroalkynyl;

Y is selected from among $CR_1R_2$, O, N(J), and S;

$T_1$ and $T_2$ are each, independently, an internucleoside linking group linking the bicyclic nucleoside to the oligonucleotide or one of $T_1$ and $T_2$ is an internucleoside linking group linking the bicyclic nucleoside to the oligonucleotide and the other of $T_1$ and $T_2$ is hydroxyl, a protected hydroxyl, a linked conjugate group or a 5' or 3'-terminal group;

n is from 1 to 3;

J is hydrogen, a halogen, an optionally substituted $C_1$-$C_5$ alkyl, an optionally substituted $C_1$-$C_5$ alkenyl, an optionally substituted $C_1$-$C_5$ alkynyl, an optionally substituted heteroalkyl, an optionally substituted heteroalkenyl, or an optionally substituted heteroalkynyl; and Bx is the heterocyclic base moiety of Formula I or Formula II.

In certain embodiments, X is selected from among: 4'-$CH_2O$-2', 4'-$CH(CH_3)O$-2', and 4'-$CH_2CH_2O$-2'. In certain embodiments, X is selected from among 4'-$CH_2O$-2' and 4'-$CH_2CH_2O$-2'. In certain embodiments, X is 4'-$CH_2O$-2'. In certain embodiments, X is 4'-$CH_2CH_2O$-2'.

In any of such embodiments, the bicyclic nucleoside may be in the α-L configuration or in the β-D configuration. In certain embodiments, the bicyclic nucleoside has the configuration:

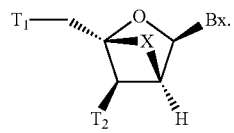

In certain embodiments, each nucleoside of an oligonucleotide of the present invention is a bicyclic nucleoside. In certain such embodiments, each nucleoside comprises the same bicyclic sugar moiety. In certain embodiments at least two nucleosides comprise bicyclic sugar moieties that are different from one another.

In certain embodiments, oligonucleotides of the present invention comprise at least one non-bicyclic nucleoside. Certain such oligonucleotides comprise at least one modified non-bicyclic nucleoside. In certain such embodiments, at least one modified nucleoside comprises at least one modified non-bicyclic nucleoside selected from among: 2'-O—$(CH_2)_2$—$OCH_3$, 2'-$OCH_3$, and 2'-F. In certain embodiments, oligonucleotides of the present invention comprise at least one unmodified nucleoside, such as a ribonucleoside and/or a deoxyribonucleoside.

In certain embodiments, oligonucleotides of the present invention comprise two or more bicyclic nucleosides having a base moiety of Formula I or I and a sugar moiety of Formula III. In certain such embodiments, the two or more bicyclic nucleosides all comprise the same bicyclic sugar moiety. In certain embodiments, at least two of the two or more bicyclic nucleosides comprise bicyclic sugar moieties that are different from one another.

In certain embodiments, oligonucleotides of the present invention consist of 8-10 linked nucleosides. In certain embodiments, oligonucleotides of the present invention consist of 8-10 linked nucleosides. In certain embodiments, oligonucleotides of the present invention consist of 10-12 linked nucleosides. In certain embodiments, oligonucleotides of the present invention consist of 12-14 linked nucleosides. In certain embodiments, oligonucleotides of the present invention consist of 14-16 linked nucleosides. In certain embodiments, oligonucleotides of the present invention consist of 16-18 linked nucleosides. In certain embodiments, oligonucleotides of the present invention consist of 18-20 linked nucleosides. In certain embodiments, oligonucleotides of the present invention consist of 20-22 linked nucleosides. In certain embodiments, oligonucleotides of the present invention consist of 22-24 linked nucleosides. In certain embodiments, oligonucleotides of the present invention consist of 24-26 linked nucleosides. In certain embodiments, oligonucleotides of the present invention consist of 11-18 linked nucleosides.

In certain embodiments, oligonucleotides of the present invention are gapmers. In certain such embodiments, such gapmers comprise at least one bicyclic nucleoside of Formula III in at least one wing of the gapmer. In certain embodiments, such gapmers comprise at least one bicyclic nucleoside of Formula III in each wing of the gapmer. In certain embodiments, each nucleoside of each wing is a bicyclic nucleoside comprising a sugar moiety of Formula III. In certain embodiments, such gapmers consist of 1-6 nucleosides. In certain embodiments, such gapmers consist of 1-6 nucleosides. In certain embodiments, such gapmers consist of 1-5 nucleosides. In certain embodiments, such gapmers consist of 1-4 nucleosides. In certain embodiments, such gapmers consist of 1-3 nucleosides. In certain embodiments, such gapmers consist of 1-2 nucleosides.

In certain embodiments, such gapmers consist of 1 nucleoside.

In certain embodiments where an oligonucleotide of the present invention is a gapmer, the gap consists of 8-10 nucleosides. In certain embodiments where an oligonucleotide of the present invention is a gapmer, the gap consists of 10-12 nucleosides. In certain embodiments where an oligonucleotide of the present invention is a gapmer, the gap consists of 12-14 nucleosides. In certain embodiments where an oligonucleotide of the present invention is a gapmer, the gap consists of 14-16 nucleosides. In certain embodiments where an oligonucleotide of the present invention is a gapmer, the gap consists of 16-18 nucleosides. In certain embodiments where an oligonucleotide of the present invention is a gapmer, the gap consists of 18-20 nucleosides. In certain embodiments where an oligonucleotide of the present invention is a gapmer, the gap consists of 20-22 nucleosides. In certain embodiments where an oligonucleotide of the present invention is a gapmer, the gap consists of 8-9 nucleosides. In certain embodiments where an oligonucleotide of the present invention is a gapmer, the gap consists of 9-11 nucleosides.

In certain embodiments where an oligonucleotide of the present invention is a gapmer, the sugar modification of each nucleoside of one wing of the gapmer and the sugar modification of each nucleoside of the other wing of the gapmer are the same as one another. In certain embodiments where an oligonucleotide of the present invention is a gapmer, the sugar modification of each nucleoside of one wing of the gapmer and the sugar modification of each nucleoside of the other wing of the gapmer are different from one another.

In certain embodiments where an oligonucleotide of the present invention is a gapmer, the nucleosides of the gap are all unmodified nucleosides. In certain such embodiments, the nucleosides of the gap are all deoxyribonucleosides. In certain embodiments, the nucleosides of the gap are modified nucleosides.

In certain embodiments, oligonucleotide of the present invention have an alternating motif wherein regions of nucleosides having a sugar moiety of Formula III alternate with differently modified nucleosides. In certain such embodiments, oligonucleotides have at least four, at least five, at least six, at least seven, at least eight, an least nine, at least ten, at least eleven, or at least twelve separate regions. In certain embodiments the separate regions alternate between nucleosides of one type of modification and nucleoside of a different type of modification. In certain embodiments, the regions alternate among three types of modifications. In certain embodiments, each region comprises modifications that are different from the modifications of any other region.

In certain embodiments, an oligonucleotide of the present invention comprises at least one modified internucleoside linkage. In certain such embodiments, at least one modified internucleoside linkage is a phosphorothioate internucleoside linkages.

In certain embodiments, an oligonucleotide of the present invention is an antisense compound. In certain such embodiments, the oligonucleotide is complementary to a target nucleic acid selected from among: target mRNA, target pre-mRNA, target microRNA, and a target non-coding RNA. In certain embodiments, the target nucleic acid is a mammalian target nucleic acid, including, but not limited to a human nucleic acid, including, but not limited to a human mRNA. In certain embodiments where an oligonucleotide of the present invention is an antisense compound, the oligonucleotide is at least 85%, 90%, 95%, 98%, or 100% complementary to a target nucleic acid.

In certain embodiments, the invention provides oligomeric compounds comprising an oligonucleotide of the present invention. In certain embodiments, such oligomeric compounds comprise at least one terminal group. In certain embodiments, such terminal group is selected from: a conjugate group, either directly attached or attached through a linker; a capping group, an additional modified or unmodified nucleoside; an inverted nucleoside; and an abasic nucleoside. In certain embodiments, such terminal group is attached to the 3' terminal end and/or the 5' terminal end. In certain embodiments, oligomeric compounds comprise one or more internally attached conjugate groups.

In certain embodiments, oligomeric compounds of the present invention are not toxic when administered to an animal, including a mouse or human. In certain embodiments, oligomeric compounds of the present invention are less toxic when administered to an animal when compared to the same compound comprising one or more bicyclic nucleosides comprising a nucleobase of Formula IV or Formula V. In certain embodiments, oligomeric compounds of the present invention have a MNTD of less than 66 mg/kg when administered to an animal. In certain embodiments, oligomeric compounds of the present invention have a MNTD of less than 33 mg/kg when administered to an animal. In certain embodiments, oligomeric compounds of the present invention have a MNTD of less than 1 mg/kg when administered to an animal.

In certain embodiments, although the oligomeric compounds of the present invention are not toxic, or less toxic compared to counterpart oligomeric compounds comprising bicyclic nucleosides having a nucleobase of Formula IV or V, such oligomeric compounds of the present invention have the same or only slightly reduced antisense activity. Accordingly, in certain embodiments, the oligomeric compounds of the present invention have improved therapeutic index compared to counterpart oligomeric compounds comprising one or more bicyclic nucleoside having a nucleobase of Formula IV or V. In certain embodiments, oligomeric compounds of the present invention have a therapeutic index of greater than 5 when tested in an animal, including, but not limited to, a mouse or human.

In certain embodiments, the present invention provides methods comprising contacting a cell with an oligomeric compound according to the present invention. In certain embodiments, such methods include detecting antisense activity. In certain such embodiments such detecting antisense activity comprises detecting a phenotypic change in the cell, detecting a change in the amount of target nucleic acid in the cell, and/or detecting a change in the amount of a target protein. In certain embodiments, such cell is in vitro or in an animal, such as a mouse or human.

In certain embodiments, the present invention provides methods of modulating mRNA in a cell comprising contacting a cell with an oligomeric compound according to the present invention. In certain embodiments, such methods include detecting antisense activity. In certain such embodiments such detecting antisense activity comprises detecting a phenotypic change in the cell, detecting a change in the amount of target nucleic acid in the cell, and/or detecting a change in the amount of a target protein. In certain embodiments, such cell is in vitro or in an animal, such as a mouse or human.

In certain embodiments, the present invention provides methods comprising administering an oligomeric compound according to the present invention to an animal. In certain embodiments, such methods include detecting antisense activity in the animal. In certain such embodiments such detecting antisense activity comprises detecting a phenotypic change in the animal. In certain such embodiments, the phenotypic change is a change in the amount or quality of a biological marker of activity; a change in the amount of target nucleic acid in the animal; and/or a change in the amount of a target protein. In certain embodiments, the animal is a mouse or human. In certain embodiments, such methods comprising assessing toxicity in the animal. In certain such embodiments, assessing toxicity in the animal comprises measuring a marker for toxicity including, but not limited to, the serum concentration of one or more liver transaminase such as alanine aminotranferease or aspartate aminotransferase.

In certain embodiments, the invention provides duplexes comprising two oligomeric compounds, wherein one or both oligomeric compounds comprises an oligonucleotide of the present invention.

In certain embodiments, the invention provides an oligonucleotide of Formula:

5'-LDLDDLLDDLDLDLL-3' wherein, each L is a bicylcic nucleoside comprising a bicyclic sugar moiety and a nucleobase, wherein none of the nucleobases of the L nucleosides has the structure of Formula IV or Formula V:

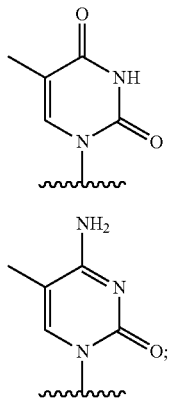

and
wherein each D is an unmodified deoxynucleoside.

In certain such embodiments the sugar moiety of each L nucleoside comprises a 4'-2' bridge having the formula: 4'-CH$_2$O-2'.

In certain embodiments, the invention provides oligonucleotides having the Formula:

5'-LLLLDDDDDDDDLLLL-3' wherein, each L is a bicylcic nucleoside comprising a bicyclic sugar moiety and a nucleobase, wherein none of the nucleobases of the L nucleosides has the structure of Formula IV or Formula V:

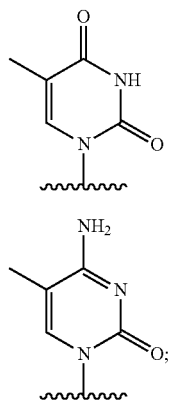

and
wherein each D is an unmodified deoxynucleoside.

In certain such embodiments the sugar moiety of each L nucleoside comprises a 4'-2' bridge having the formula: 4'-CH$_2$O-2'.

In certain embodiments, the invention provides oligonucleotides having the Formula:

5'-(L)$_{2-4}$(D)$_{6-14}$(L)$_{2-4}$-3' wherein, each L is a bicylcic nucleoside comprising a bicyclic sugar moiety and a nucleobase, wherein none of the nucleobases of the L nucleosides has the structure of Formula IV or Formula V:

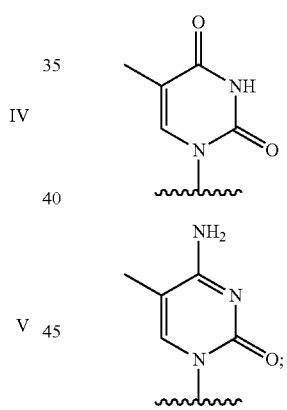

and
wherein each D is an unmodified deoxynucleoside.

In certain such embodiments the sugar moiety of each L nucleoside comprises a 4'-2' bridge having the formula: 4'-CH$_2$O-2'.

In certain embodiments, the invention provides methods of producing a compound having reduced toxicity when compared to a parent compound wherein the parent compound comprises at least one bicyclic nucleoside comprising a 5-methyl pyrimidine, comprising:

preparing a compound wherein at least one bicyclic nucleoside comprising a 5-methyl pyrimidine in the parent is instead a bicyclic nucleoside comprising an unmodified pyrimidine; and thereby producing a compound having reduced toxicity compared to the parent compound.

In certain embodiments, the invention provides methods of treating a disease or condition in an animal comprising:

administering an oligomeric compound of the present invention to an animal;

monitoring the effect of the compound on the disease or condition; and monitoring the animal for toxicity.

In certain embodiments, the invention provides methods of treating a disease or condition in an animal comprising:

administering an oligomeric compound of any of originally filed claims 152-168 to an animal;

monitoring the effect of the compound on the disease or condition;

monitoring the animal for toxicity; and calculating the therapeutic index for the oligomeric compound.

In certain embodiments, the present invention provides pharmaceutical compositions comprising an oligomeric compound of any of originally filed claims 152-168 and a pharmaceutically acceptable carrier or diluent.

DETAILED DESCRIPTION OF THE INVENTION

It is to be understood that both the foregoing general description and the following detailed description are exemplary and explanatory only and are not restrictive of the invention, as claimed. Herein, the use of the singular includes the plural unless specifically stated otherwise. As used herein, the use of "or" means "and/or" unless stated otherwise. Furthermore, the use of the term "including" as well as other forms, such as "includes" and "included", is not limiting. Also, terms such as "element" or "component" encompass both elements and components comprising one unit and elements and components that comprise more than one subunit, unless specifically stated otherwise.

The section headings used herein are for organizational purposes only and are not to be construed as limiting the subject matter described. All documents, or portions of documents, cited in this application, including, but not limited to, patents, patent applications, articles, books, and treatises, are hereby expressly incorporated by reference in their entirety for any purpose.

Definitions

Unless specific definitions are provided, the nomenclature utilized in connection with, and the procedures and techniques of, analytical chemistry, synthetic organic chemistry, and medicinal and pharmaceutical chemistry described herein are those well known and commonly used in the art. Standard techniques may be used for chemical synthesis, and chemical analysis. Certain such techniques and procedures may be found for example in "Carbohydrate Modifications in Antisense Research" Edited by Sangvi and Cook, American Chemical Society, Washington D.C., 1994; "Remington's Pharmaceutical Sciences," Mack Publishing Co., Easton, Pa., 18th edition, 1990; and "Antisense Drug Technology, Principles, Strategies, and Applications" Edited by Stanley T. Crooke, CRC Press, Boca Raton, Fla.; and Sambrook et al., "Molecular Cloning, A laboratory Manual," $2^{nd}$ Edition, Cold Spring Harbor Laboratory Press, 1989, which are hereby incorporated by reference for any purpose. Where permitted, all patents, applications, published applications and other publications and other data referred to throughout in the disclosure herein are incorporated by reference in their entirety.

Unless otherwise indicated, the following terms have the following meanings:

As used herein, "nucleoside" refers to a glycosylamine comprising a heterocyclic base moiety and a sugar moiety. Nucleosides include, but are not limited to, naturally occurring nucleosides, abasic nucleosides, modified nucleosides, and nucleosides having mimetic bases and/or sugar groups. Nucleosides may be modified with any of a variety of substituents.

As used herein, "nucleotide" refers to a nucleoside comprising a phosphate linking group. As used herein, nucleosides include nucleotides.

As used herein, "nucleobase" refers to the heterocyclic base portion of a nucleoside. Nucleobases may be naturally occurring or may be modified. In certain embodiments, a nucleobase may comprise any atom or group of atoms capable of hydrogen bonding to a base of another nucleic acid.

As used herein, "modified nucleoside" refers to a nucleoside comprising at least one modification compared to naturally occurring RNA or DNA nucleosides. Such modification may be at the sugar moiety and/or at the nucleobases.

As used herein, "unmodified nucleoside" refers to an RNA or DNA nucleoside. In certain embodiments, unmodified nucleosides may be linked by modified internucleoside linkages.

As used herein, "bicyclic nucleoside" or "BNA" refers to a nucleoside wherein the sugar moiety of the nucleoside comprises a bridge connecting two carbon atoms of the sugar ring, thereby forming a bicyclic sugar moiety.

As used herein, "4'-2' bicyclic nucleoside" refers to a bicyclic nucleoside wherein the bridge connecting two carbon atoms of the sugar ring connects the 2' carbon atom and the 4' carbon atom of the sugar ring.

As used herein, "2'-modified" or "2'-substituted" refers to a nucleoside comprising a sugar comprising a substituent at the 2' position other than H or OH. 2'-modified nucleosides, include, but are not limited to, bicyclic nucleosides wherein the bridge connecting two carbon atoms of the sugar ring connects the 2' carbon and another carbon of the sugar ring; and nucleosides with non-bridging 2'substituents, such as allyl, amino, azido, thio, O-allyl, O—$C_1$-$C_{10}$ alkyl, —$OCF_3$, O—$(CH_2)_2$—O—$CH_3$, 2'-O$(CH_2)_2SCH_3$, O—$(CH_2)_2$—O—N$(R_m)(R_n)$, or O—$CH_2$—C(=O)—N$(R_m)(R_n)$, where each $R_m$ and $R_n$ is, independently, H or substituted or unsubstituted $C_1$-$C_{10}$ alkyl. 2'-modified nucleosides may further comprise other modifications, for example at other positions of the sugar and/or at the nucleobase.

As used herein, "2'-F" refers to a nucleoside comprising a sugar comprising a fluoro group at the 2' position.

As used herein, "2'-OMe" refers to a nucleoside comprising a sugar comprising an O-Methyl group at the 2' position.

As used herein, "MOE" refers to a nucleoside comprising a sugar comprising a 2'-O-methoxyethyl substituent.

As used herein, "5-methyl pyrimidine bicyclic nucleoside" refers to a nucleoside having a bicyclic sugar moiety and a pyrimidine nucleobase comprising a methyl group at the 5 position.

As used herein, "non-methylated pyrimidine bicyclic nucleoside" refers to a nucleoside having a bicyclic sugar moiety and a pyrimidine nucleobase that does not comprise a methyl group at the 5 position.

As used herein, "oligonucleotide" refers to a compound comprising a plurality of linked nucleosides. In certain embodiments, one or more nucleosides of an oligonucleotide is modified. In certain embodiments, an oligonucleotide comprises one or more ribonucleosides (RNA) and/or deoxyribonucleosides (DNA).

As used herein "oligonucleoside" refers to an oligonucleotide in which none of the internucleoside linkages contains a phosphorus atom. As used herein, oligonucleotides include oligonucleosides.

As used herein, "modified oligonucleotide" refers to an oligonucleotide comprising at least one modified nucleoside and/or at least one modified internucleoside linkage.

As used herein "internucleoside linkage" refers to a covalent linkage between adjacent nucleosides.

As used herein "naturally occurring internucleoside linkage" refers to a 3' to 5' phosphodiester linkage.

As used herein, "modified internucleoside linkage" refers to any internucleoside linkage other than a naturally occurring internucleoside linkage.

As used herein, "oligomeric compound" refers to a polymeric structure comprising two or more sub-structures. In certain embodiments, oligomeric compounds comprise an oligonucleotide. In certain embodiments, an oligomeric compound comprises a single-stranded oligonucleotide. In certain embodiments, oligomeric compounds comprise one or more conjugate groups and/or terminal groups.

As used herein, "duplex" refers to two separate oligomeric compounds that are hybridized together.

As used herein, "terminal group" refers to one or more atom attached to either or both the 3' end or the 5' end of an oligonucleotide. In certain embodiments a terminal group is a conjugate group. In certain embodiments, a terminal group comprises one or more additional nucleosides.

As used herein, "conjugate" refers to an atom or group of atoms bound to an oligonucleotide or oligomeric compound. In general, conjugate groups modify one or more properties of the compound to which they are attached, including, but not limited to pharmacodynamic, pharmacokinetic, binding, absorption, cellular distribution, cellular uptake, charge and clearance. Conjugate groups are routinely used in the chemical arts and are linked directly or via an optional linking moiety or linking group to the parent compound such as an oligomeric compound. In certain embodiments, conjugate groups includes without limitation, intercalators, reporter molecules, polyamines, polyamides, polyethylene glycols, thioethers, polyethers, cholesterols, thiocholesterols, cholic acid moieties, folate, lipids, phospholipids, biotin, phenazine, phenanthridine, anthraquinone, adamantane, acridine, fluoresceins, rhodamines, coumarins and dyes. In certain embodiments, conjugates are terminal groups. In certain embodiments, conjugates are attached to internal nucleosides of an oligonucleotide.

As used herein, "conjugate linking group" refers to any atom or group of atoms used to attach a conjugate to an oligonucleotide or oligomeric compound. Linking groups or bifunctional linking moieties such as those known in the art are amenable to the present invention.

As used herein, "protecting group," as used herein, refers to a labile chemical moiety which is known in the art to protect reactive groups including without limitation, hydroxyl, amino and thiol groups, against undesired reactions during synthetic procedures. Protecting groups are typically used selectively and/or orthogonally to protect sites during reactions at other reactive sites and can then be removed to leave the unprotected group as is or available for further reactions. Protecting groups as known in the art are described generally in Greene and Wuts, Protective Groups in Organic Synthesis, 3rd edition, John Wiley & Sons, New York (1999).

As used herein, the term "orthogonally protected" refers to functional groups which are protected with different classes of protecting groups, wherein each class of protecting group can be removed in any order and in the presence of all other classes (see, Barany, G. and Merrifield, R. B., *J. Am. Chem. Soc.*, 1977, 99, 7363; idem, 1980, 102, 3084.) Orthogonal protection is widely used in for example automated oligonucleotide synthesis. A functional group is deblocked in the presence of one or more other protected functional groups which is not affected by the deblocking procedure. This deblocked functional group is reacted in some manner and at some point a further orthogonal protecting group is removed under a different set of reaction conditions. This allows for selective chemistry to arrive at a desired compound or oligomeric compound.

As used herein, "toxic oligomeric compound" refers to an oligomeric compound that, when administered to an animal results in a toxic response in the animal. In certain embodiments, administration of a toxic oligomeric compound to an animal results in a change in one or more markers of toxicity. In certain embodiments, a toxic oligomeric compound is a compound that results in a toxic response in an animal when it is administered at a dose of about 10 mg/kg, 20 mg/kg, 30 mg/kg, 33 mg/kg, 50 mg/kg, 60 mg/kg, 66 mg/kg, 100 mg/kg, 150 mg/kg, 200 mg/kg, or 500 mg/kg.

As used herein, "maximum non-toxic dose" or "MNTD" refers to the highest dose that may be administered to an animal that does not result in a toxic response.

As used herein, "toxic response" or "toxicity" refers to an undesired physiological responses attributable to a administration of a pharmaceutical agent. In certain embodiments, toxic response includes, without limitation, injection site reactions, liver function test abnormalities, renal function abnormalities, liver toxicity, renal toxicity, central nervous system abnormalities, and myopathies. For example, increased aminotransferase levels in serum may indicate liver toxicity or liver function abnormality. For example, increased bilirubin may indicate liver toxicity or liver function abnormality. In certain embodiments a toxic response is assessed by monitoring one or more markers of toxicity. In certain embodiments, a toxic response requires a substantial change in one or more marker of toxicity. In certain embodiments, a toxic response is characterized by a change in a marker of toxicity of more than 20%, more than 50%, more than 100% or more than 200%. In certain embodiments, a marker of toxicity is elevation of the serum concentration of one or more liver transaminase, such as alanine aminotranferease (ALT) and aspartate aminotransferase (AST).

As used herein, "antisense compound" refers to an oligomeric compound, at least a portion of which is at least partially complementary to a target nucleic acid to which it hybridizes. In certain embodiments, an antisense compound modulates (increases or decreases) expression or amount of a target nucleic acid. In certain embodiments, an antisense compound alters splicing of a target pre-mRNA resulting in a different splice variant. In certain embodiments, an antisense compound modulates expression of one or more different target proteins.

As used herein, "antisense oligonucleotide" refers to an antisense compound that is an oligonucleotide.

As used herein, "antisense activity" refers to any detectable and/or measurable activity attributable to the hybridization of an antisense compound to its target nucleic acid. In certain embodiments, such activity may be an increase or decrease in an amount of a nucleic acid or protein. In certain embodiments, such activity may be a change in the ratio of splice variants of a nucleic acid or protein. Detection and/or measuring of antisense activity may be direct or indirect. For example, in certain embodiments, antisense activity is assessed by detecting and/or measuring the amount of target protein or the relative amounts of splice variants of a target protein. In certain embodiments, antisense activity is assessed by detecting and/or measuring the amount of target nucleic acids and/or cleaved target nucleic acids and/or alternatively spliced target nucleic acids. In certain embodiments, antisense activity is assessed by observing a phenotypic change in a cell or animal.

As used herein "detecting" or "measuring" in connection with an activity, response, or effect indicate that a test for detecting or measuring such activity, response, or effect is performed. Such detection and/or measuring may include values of zero. Thus, if a test for detection or measuring results in a finding of no activity (activity of zero), the step of detecting or measuring the activity has nevertheless been performed. For example, in certain embodiments, the present invention provides methods that comprise steps of detecting antisense activity, detecting toxicity, and/or measuring a marker of toxicity. Any such step may include values of zero.

As used herein, "target nucleic acid" refers to any nucleic acid molecule the expression, amount, or activity of which is capable of being modulated by an antisense compound. Target nucleic acids include, but are not limited to, RNA (including, but not limited to pre-mRNA and mRNA or portions thereof) transcribed from DNA encoding a target protein, and also cDNA derived from such RNA, and miRNA. For example, the target nucleic acid can be a cellular gene (or mRNA transcribed from the gene) whose expression is associated with a particular disorder or disease state, or a nucleic acid molecule from an infectious agent. In certain embodiments, target nucleic acid is a viral or bacterial nucleic acid.

As used herein, "target mRNA" refers to a pre-selected RNA molecule that encodes a protein.

As used herein, "target pre-mRNA" refers to a pre-selected RNA transcript that has not been fully processed into mRNA. Notably, pre-RNA includes one or more intron.

As used herein, "target microRNA" refers to a pre-selected non-coding RNA molecule about 18-30 nucleobases in length that modulates expression of one or more proteins.

As used herein, "target pdRNA" refers to refers to a pre-selected RNA molecule that interacts with one or more promoter to modulate transcription.

As used herein, "target non-coding RNA" refers to a pre-selected RNA molecule that is not translated to generate a protein. Certain non-coding RNA are involved in regulation of expression.

As used herein, "target viral nucleic acid" refers to a pre-selected nucleic acid (RNA or DNA) associated with a virus. Such viral nucleic acid includes nucleic acids that constitute the viral genome, as well as transcripts (including reverse-transcripts and RNA transcribed from RNA) of those nucleic acids, whether or not produced by the host cellular machinery. In certain instances, viral nucleic acids also include host nucleic acids that are recruited by a virus upon viral infection.

As used herein, "targeting" or "targeted to" refers to the association of an antisense compound to a particular target nucleic acid molecule or a particular region of nucleotides within a target nucleic acid molecule.

As used herein, "nucleobase complementarity" refers to a nucleobase that is capable of base pairing with another nucleobase. For example, in DNA, adenine (A) is complementary to thymine (T). For example, in RNA, adenine (A) is complementary to uracil (U). In certain embodiments, complementary nucleobase refers to a nucleobase of an antisense compound that is capable of base pairing with a nucleobase of its target nucleic acid. For example, if a nucleobase at a certain position of an antisense compound is capable of hydrogen bonding with a nucleobase at a certain position of a target nucleic acid, then the position of hydrogen bonding between the oligonucleotide and the target nucleic acid is considered to be complementary at that nucleobase pair. Nucleobases comprising certain modifications may maintain the ability to pair with a counterpart nucleobase and thus, are still capable of nucleobase complementartity.

As used herein, "non-complementary nucleobase" refers to a pair of nucleobases that do not form hydrogen bonds with one another or otherwise support hybridization.

As used herein, "complementary" refers to the capacity of an oligomeric compound to hybridize to another oligomeric compound or nucleic acid through nucleobase complementarity. In certain embodiments, an antisense compound and its target are complementary to each other when a sufficient number of corresponding positions in each molecule are occupied by nucleobases that can bond with each other to allow stable association between the antisense compound and the target. One skilled in the art recognizes that the inclusion of mismatches is possible without eliminating the ability of the oligomeric compounds to remain in association. Therefore, described herein are antisense compounds that may comprise up to about 20% nucleotides that are mismatched (i.e., are not nucleobase complementary to the corresponding nucleotides of the target). Preferably the antisense compounds contain no more than about 15%, more preferably not more than about 10%, most preferably not more than 5% or no mismatches. The remaining nucleotides are nucleobase complementary or otherwise do not disrupt hybridization (e.g., universal bases). One of ordinary skill in the art would recognize the compounds provided herein are at least 80%, at least 85%, at least 90%, at least 95%, at least 96%, at least 97%, at least 98%, at least 99% or 100% complementary to a target nucleic acid.

As used herein, "hybridization" refers to the pairing of complementary oligomeric compounds (e.g., an antisense compound and its target nucleic acid or an antidote to its antisense compound). While not limited to a particular mechanism, the most common mechanism of pairing involves hydrogen bonding, which may be Watson-Crick, Hoogsteen or reversed Hoogsteen hydrogen bonding, between complementary nucleoside or nucleotide bases (nucleobases). For example, the natural base adenine is nucleobase complementary to the natural nucleobases thymidine and uracil which pair through the formation of hydrogen bonds. The natural base guanine is nucleobase complementary to the natural bases cytosine and 5-methyl cytosine. Hybridization can occur under varying circumstances.

As used herein, "specifically hybridizes" refers to the ability of an oligomeric compound to hybridize to one nucleic acid site with greater affinity than it hybridizes to another nucleic acid site. In certain embodiments, an antisense oligonucleotide specifically hybridizes to more than one target site.

As used herein, "modulation" refers to a perturbation of amount or quality of a function or activity when compared to the function or activity prior to modulation. For example, modulation includes the change, either an increase (stimulation or induction) or a decrease (inhibition or reduction) in gene expression. As further example, modulation of expression can include perturbing splice site selection of pre-mRNA processing, resulting in a change in the amount of a particular splice-variant present compared to conditions that were not perturbed.

As used herein, "chemical motif" refers to the pattern of unmodified and/or modified and/or differently modified nucleotides in an oligonucleotide or oligomeric compound.

As used herein, "blockmer" refers to an oligomeric compound comprising a sequence of nucleosides having uniform modifications that is internally interrupted by a block of two or more differently modified nucleosides.

As used herein, "hemimer" refers to an oligomeric compound comprising a sequence of nucleosides having uniform modifications that is flanked at one end by a block of two or more differently modified nucleosides.

As used herein, "gapmer" refers to an oligomeric compound having a chemical motif comprising a central region (a "gap") and a region on either side of the central region (the "wings"), wherein the gap comprises at least one modification that is different from that of each wing. Such modifications include nucleobase, monomeric linkage, and sugar modifications as well as the absence of modification (unmodified). Thus, in certain embodiments, the nucleotide linkages in each of the wings are different than the nucleotide linkages in the gap. In certain embodiments, each wing comprises nucleotides with high affinity modifications and the gap comprises nucleotides that do not comprise that modification. In certain embodiments the nucleotides in the gap and the nucleotides in the wings all comprise high affinity modifications, but the high affinity modifications in the gap are different than the high affinity modifications in the wings. In certain embodiments, the modifications in the wings are the same as one another. In certain embodiments, the modifications in the wings are different from each other. In certain embodiments, nucleotides in the gap are unmodified and nucleotides in the wings are modified. In certain embodiments, the modification(s) in each wing are the same. In certain embodiments, the modification(s) in one wing are different from the modification(s) in the other wing. In certain embodiments, oligomeric compounds are gapmers having 2'-deoxynucleotides in the gap and nucleotides with high-affinity modifications in the wing.

As used herein, "different modifications" or "differently modified" refer to nucleosides or internucleoside linkages that have different nucleoside modifications or internucleoside linkages than one another, including absence of modifications. Thus, for example, a MOE nucleoside and an unmodified DNA nucleoside are "differently modified," even though the DNA nucleoside is unmodified. Likewise, DNA and RNA are "differently modified," even though both are naturally-occurring unmodified nucleosides.

As used herein, "the same modifications" refer to nucleosides and internucleoside linkages (including unmodified nucleosides and internucleoside linkages) that are the same as one another. Thus, for example, two unmodified DNA nucleoside have "the same modification," even though the DNA nucleoside is unmodified.

As used herein, "separate regions" refers to a portion of an oligomeric compound wherein the nucleosides and internucleoside linkages within the region all comprise the same modifications; and the nucleosides and/or the internucleoside linkages of any neighboring portions include at least one different modification.

As used herein, "alternating motif" refers to an oligomeric compound or a portion thereof, having at lease four separate regions of modified nucleosides in a pattern $(AB)_nA_m$ where A represents a first type of modification; B represent a different type of modification; n is 2-15; and m is 0 or 1. Thus, in certain embodiments, alternating motifs include 4, 5, 6, 7, 8, 9, 10, 11, 12, 13, 14, 15, 16, 17, 18, 19, or 20 or more alternating regions. In certain embodiments, each region independently comprises 1-4 nucleosides.

As used herein, "fully modified" refers to an oligomeric compound or portion thereon wherein each nucleoside is a modified nucleoside. The modifications of the nucleosides of a fully modified oligomeric compound may all be the same or one or more may be different from one another.

As used herein, "pharmaceutically acceptable salts" refers to salts of active compounds that retain the desired biological activity of the active compound and do not impart undesired toxicological effects thereto.

As used herein, "cap structure" or "terminal cap moiety" refers to chemical modifications incorporated at either terminus of an antisense compound.

As used herein, "mitigation" refers to a lessening of at least one activity or one indicator of the severity of a condition or disease. The severity of indicators may be determined by subjective or objective measures which are known to those skilled in the art. In certain embodiments, the condition may be a toxic effect of a therapeutic agent.

As used herein, "pharmaceutical agent" refers to a substance that provides a therapeutic effect when administered to a subject. In certain embodiments, a pharmaceutical agent provides a therapeutic benefit. In certain embodiments, a pharmaceutical agent provides a toxic effect.

As used herein, "therapeutic index" refers to a measure of the therapeutic benefit of a pharmaceutical agent divided by a measure of a toxic effect of the pharmaceutical agent.

As used herein, "therapeutically effective amount" refers to an amount of a pharmaceutical agent that provides a therapeutic benefit to an animal.

As used herein, "activity to toxicity ratio" refers to any measure of antisense activity relative to any measure of toxicity.

As used herein, "administering" refers to providing a pharmaceutical agent to an animal, and includes, but is not limited to administering by a medical professional and self-administering.

As used herein, "co-administer" refers to administering more than one pharmaceutical agent to an animal. The more than one agent may be administered together or separately; at the same time or different times; through the same route of administration or through different routes of administration.

As used herein, "route of administration" refers to the means by which a pharmaceutical agent is administered to an animal.

As used herein, "pharmaceutical composition" refers to a mixture of substances suitable for administering to an animal. For example, a pharmaceutical composition may comprise an antisense oligonucleotide and a sterile aqueous solution.

As used herein, "pharmaceutically acceptable carrier or diluent" refers to any substance suitable for use in administering to an animal. In certain embodiments, a pharmaceutically acceptable carrier or diluent is sterile saline. In certain embodiments, such sterile saline is pharmaceutical grade saline.

As used herein, "animal" refers to a human or a non-human animal, including, but not limited to, mice, rats, rabbits, dogs, cats, pigs, and non-human primates, including, but not limited to, monkeys and chimpanzees.

As used herein, "parenteral administration," refers to administration through injection or infusion. Parenteral administration includes, but is not limited to, subcutaneous administration, intravenous administration, or intramuscular administration.

As used herein, "subcutaneous administration" refers to administration just below the skin. "Intravenous administration" refers to administration into a vein.

As used herein, "active pharmaceutical ingredient" refers to the substance in a pharmaceutical composition that provides a desired effect.

As used herein, "prodrug" refers to a therapeutic agent that is prepared in an inactive form that is converted to an active form (i.e., drug) within the body or cells thereof by the action of endogenous enzymes or other chemicals and/or conditions.

As used herein, "alkyl," refers to a saturated straight or branched hydrocarbon radical containing up to twenty four carbon atoms. Examples of alkyl groups include, but are not limited to, methyl, ethyl, propyl, butyl, isopropyl, n-hexyl, octyl, decyl, dodecyl and the like. Alkyl groups typically include from 1 to about 24 carbon atoms, more typically from 1 to about 12 carbon atoms ($C_1$-$C_{12}$ alkyl) with from 1 to about 6 carbon atoms being more preferred. The term "lower alkyl" as used herein includes from 1 to about 6 carbon atoms. Alkyl groups as used herein may optionally include one or more further substituent groups.

As used herein, "alkenyl," refers to a straight or branched hydrocarbon chain radical containing up to twenty four carbon atoms and having at least one carbon-carbon double bond. Examples of alkenyl groups include, but are not limited to, ethenyl, propenyl, butenyl, 1-methyl-2-buten-1-yl, dienes such as 1,3-butadiene and the like. Alkenyl groups typically include from 2 to about 24 carbon atoms, more typically from 2 to about 12 carbon atoms with from 2 to about 6 carbon atoms being more preferred. Alkenyl groups as used herein may optionally include one or more further substituent groups.

As used herein, "alkynyl," refers to a straight or branched hydrocarbon radical containing up to twenty four carbon atoms and having at least one carbon-carbon triple bond. Examples of alkynyl groups include, but are not limited to, ethynyl, 1-propynyl, 1-butynyl, and the like. Alkynyl groups typically include from 2 to about 24 carbon atoms, more typically from 2 to about 12 carbon atoms with from 2 to about 6 carbon atoms being more preferred. Alkynyl groups as used herein may optionally include one or more further substituent groups.

As used herein, "aminoalkyl" refers to an amino substituted alkyl radical. This term is meant to include $C_1$-$C_{12}$ alkyl groups having an amino substituent at any position and wherein the alkyl group attaches the aminoalkyl group to the parent molecule. The alkyl and/or amino portions of the aminoalkyl group can be further substituted with substituent groups.

As used herein, "aliphatic," refers to a straight or branched hydrocarbon radical containing up to twenty four carbon atoms wherein the saturation between any two carbon atoms is a single, double or triple bond. An aliphatic group preferably contains from 1 to about 24 carbon atoms, more typically from 1 to about 12 carbon atoms with from 1 to about 6 carbon atoms being more preferred. The straight or branched chain of an aliphatic group may be interrupted with one or more heteroatoms that include nitrogen, oxygen, sulfur and phosphorus. Such aliphatic groups interrupted by heteroatoms include without limitation polyalkoxys, such as polyalkylene glycols, polyamines, and polyimines. Aliphatic groups as used herein may optionally include further substituent groups.

As used herein, "alicyclic" or "alicyclyl" refers to a cyclic ring system wherein the ring is aliphatic. The ring system can comprise one or more rings wherein at least one ring is aliphatic. Preferred alicyclics include rings having from about 5 to about 9 carbon atoms in the ring. Alicyclic as used herein may optionally include further substituent groups.

As used herein, "alkoxy," refers to a radical formed between an alkyl group and an oxygen atom wherein the oxygen atom is used to attach the alkoxy group to a parent molecule. Examples of alkoxy groups include, but are not limited to, methoxy, ethoxy, propoxy, isopropoxy, n-butoxy, sec-butoxy, tert-butoxy, n-pentoxy, neopentoxy, n-hexoxy and the like. Alkoxy groups as used herein may optionally include further substituent groups.

As used herein, "halo" and "halogen," refer to an atom selected from fluorine, chlorine, bromine and iodine.

As used herein, "aryl" and "aromatic," refer to a mono- or polycyclic carbocyclic ring system radicals having one or more aromatic rings. Examples of aryl groups include, but are not limited to, phenyl, naphthyl, tetrahydronaphthyl, indanyl, idenyl and the like. Preferred aryl ring systems have from about 5 to about 20 carbon atoms in one or more rings. Aryl groups as used herein may optionally include further substituent groups.

As used herein, "aralkyl" and "arylalkyl," refer to a radical formed between an alkyl group and an aryl group wherein the alkyl group is used to attach the aralkyl group to a parent molecule. Examples include, but are not limited to, benzyl, phenethyl and the like. Aralkyl groups as used herein may optionally include further substituent groups attached to the alkyl, the aryl or both groups that form the radical group.

As used herein, "heterocyclic radical" refers to a radical mono-, or poly-cyclic ring system that includes at least one heteroatom and is unsaturated, partially saturated or fully saturated, thereby including heteroaryl groups. Heterocyclic is also meant to include fused ring systems wherein one or more of the fused rings contain at least one heteroatom and the other rings can contain one or more heteroatoms or optionally contain no heteroatoms. A heterocyclic group typically includes at least one atom selected from sulfur, nitrogen or oxygen. Examples of heterocyclic groups include, [1,3] dioxolane, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, quinoxalinyl, pyridazinonyl, tetrahydrofuryl and the like. Heterocyclic groups as used herein may optionally include further substitutent groups.

As used herein, "heteroaryl," and "heteroaromatic," refer to a radical comprising a mono- or poly-cyclic aromatic ring, ring system or fused ring system wherein at least one of the rings is aromatic and includes one or more heteroatom. Heteroaryl is also meant to include fused ring systems including systems where one or more of the fused rings contain no heteroatoms. Heteroaryl groups typically include one ring atom selected from sulfur, nitrogen or oxygen. Examples of heteroaryl groups include, but are not limited to, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzooxazolyl, quinoxalinyl, and the like. Heteroaryl radicals can be attached to a parent molecule directly or through a linking moiety such as an aliphatic group or hetero atom. Heteroaryl groups as used herein may optionally include further substitutent groups.

As used herein, "heteroarylalkyl," refers to a heteroaryl group as previously defined having an alky radical that can attach the heteroarylalkyl group to a parent molecule. Examples include, but are not limited to, pyridinylmethyl, pyrimidinylethyl, napthyridinylpropyl and the like. Heteroarylalkyl groups as used herein may optionally include further substitutent groups on one or both of the heteroaryl or alkyl portions.

As used herein, "mono or poly cyclic structure" refers to any ring systems that are single or polycyclic having rings that are fused or linked and is meant to be inclusive of single and mixed ring systems individually selected from aliphatic, alicyclic, aryl, heteroaryl, aralkyl, arylalkyl, heterocyclic, heteroaryl, heteroaromatic, heteroarylalkyl. Such mono and poly cyclic structures can contain rings that are uniform or have varying degrees of saturation including fully saturated, partially saturated or fully unsaturated. Each ring can comprise ring atoms selected from C, N, O and S to give rise to heterocyclic rings as well as rings comprising only C ring atoms which can be present in a mixed motif such as for example benzimidazole wherein one ring has only carbon ring atoms and the fused ring has two nitrogen atoms. The mono or poly cyclic structures can be further substituted with substituent groups such as for example phthalimide which has two =O groups attached to one of the rings. In another aspect, mono or poly cyclic structures can be attached to a parent molecule directly through a ring atom, through a substituent group or a bifunctional linking moiety.

As used herein, "acyl," refers to a radical formed by removal of a hydroxyl group from an organic acid an d has the general formula —C(O)—X where X is typically aliphatic, alicyclic or aromatic. Examples include aliphatic carbonyls, aromatic carbonyls, aliphatic sulfonyls, aromatic sulfinyls, aliphatic sulfinyls, aromatic phosphates, aliphatic phosphates and the like. Acyl groups as used herein may optionally include further substitutent groups.

As used herein, "hydrocarbyl" refers to any group comprising C, O and H. Included are straight, branched and cyclic groups having any degree of saturation. Such hydrocarbyl groups can include one or more heteroatoms selected from N, O and S and can be further mono or poly substituted with one or more substituent groups.

As used herein, "substituent" and "substituent group," include groups that are typically added to other groups or parent compounds to enhance desired properties or give desired effects. Substituent groups can be protected or unprotected and can be added to one available site or to many available sites in a parent compound. Substituent groups may also be further substituted with other substituent groups and may be attached directly or via a linking group such as an alkyl or hydrocarbyl group to a parent compound. Unless otherwise indicated, the term substituted or "optionally substituted" refers to the following substituents: halogen, hydroxyl, alkyl, alkenyl, alkynyl, acyl (—C—(O)$R_{aa}$), carboxyl (—C(O)O—$R_{aa}$), aliphatic groups, alicyclic groups, alkoxy, substituted oxo (—O—$R_{aa}$), aryl, aralkyl, heterocyclic, heteroaryl, heteroarylalkyl, amino (—$NR_{bb}R_{cc}$), imino (=$NR_{bb}$), amido (—C(O)$NR_{bb}R_{cc}$ or —N($R_{bb}$)C(O)$R_{aa}$), azido (—$N_3$), nitro (—$NO_2$), cyano (—CN), carbamido (—OC(O)$NR_{bb}R_{cc}$ or —N($R_{bb}$)C(O)O$R_{aa}$), ureido (—N($R_{bb}$)C(O)$NR_{bb}R_{cc}$), thioureido (—N($R_{bb}$)C—(S)$NR_{bb}R_{cc}$), guanidinyl (—N($R_{bb}$)C(=$NR_{bb}$)$NR_{bb}R_{cc}$), amidinyl (—C(=$NR_{bb}$)$NR_{bb}R_{cc}$ or —N($R_{bb}$)C($NR_{bb}$)$R_{aa}$), thiol (—$SR_{bb}$), sulfinyl (—S(O)$R_{bb}$), sulfonyl (—S(O)$_2R_{bb}$), sulfonamidyl (—S(O)$_2NR_{bb}R_{cc}$ or —N($R_{bb}$)S(O)$_2R_{bb}$) and conjugate groups. Wherein each $R_{aa}$, $R_{bb}$ and $R_{cc}$ is, independently, H, an optionally linked chemical functional group or a further substituent group with a preferred list including without limitation H, alkyl, alkenyl, alkynyl, aliphatic, alkoxy, acyl, aryl, aralkyl, heteroaryl, alicyclic, heterocyclic and heteroarylalkyl.

Certain Nucleosides

In certain embodiments, the present invention provides modified nucleosides. In certain embodiments modified nucleosides comprise a modified sugar moiety. In certain embodiments modified nucleosides comprise a modified nucleobase. In certain embodiments modified nucleosides comprise a modified sugar moiety and a modified nucleobase. In certain embodiments, modified nucleosides comprise a modified sugar moiety and a non-modified nucleobase.

Certain Modified Sugar Moieties

In certain embodiments, the present invention provides modified nucleosides comprising a modified sugar moiety. In certain embodiments, a modified sugar moiety is a bicyclic sugar moiety. In certain embodiments a modified sugar moiety is a non-bicyclic modified sugar moiety.

Certain modified sugar moiety moieties are known and can be used to alter, typically increase, the affinity of the antisense compound for its target and/or increase nuclease resistance. A representative list of preferred modified sugar moieties includes but is not limited to bicyclic modified sugar moieties (BNA's), including methyleneoxy (4'-$CH_2$—O-2') BNA and ethyleneoxy (4'-$(CH_2)_2$—O-2' bridge) BNA; substituted sugar moieties, especially 2'-substituted sugar moieties having a 2'-F, 2'-$OCH_3$ or a 2'-O$(CH_2)_2$—$OCH_3$ substituent group; and 4'-thio modified sugar moieties. Sugar moieties can also be replaced with sugar moiety mimetic groups among others. Methods for the preparations of modified sugar moieties are well known to those skilled in the art. Some representative patents and publications that teach the preparation of such modified sugar moieties include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; 5,792,747; 5,700,920; 6,531,584; 6,172,209; 6,271,358; and 6,600,032; and WO 2005/121371.

Bicyclic Sugar Moieties

In certain embodiments, the present invention provides modified nucleosides comprising a bicyclic sugar moiety. Certain such sugar moieties have been described. See, for example: Singh et al., Chem. Commun., 1998, 4, 455-456; Koshkin et al., Tetrahedron, 1998, 54, 3607-3630; Wahlestedt et al., Proc. Natl. Acad. Sci. U.S.A., 2000, 97, 5633-5638; Kumar et al., Bioorg. Med. Chem. Lett., 1998, 8, 2219-2222; Singh et al., J. Org. Chem., 1998, 63, 10035-10039; Srivastava et al., J. Am. Chem. Soc., 129(26) 8362-79 (Jul. 4, 2007); U.S. Pat. Nos. 7,053,207; 6,268,490; 6,770,748; 6,794,499; 7,034,133; and 6,525,191; Elayadi et al., *Curr. Opinion Invens. Drugs*, 2001, 2, 558-561; Braasch et al., *Chem. Biol.*, 2001, 8 1-7; and Orum et al., *Curr. Opinion Mol. Ther.*, 2001, 3, 239-243; and U.S. Pat. No. 6,670,461; International applications WO 2004/106356; WO 94/14226; WO 2005/021570; each of which is incorporated by reference in its entirety.

In certain embodiments, nucleosides comprising a bicyclic sugar moiety have increased affinity for a complementary nucleic acid. In certain embodiments, nucleosides comprising a bicyclic sugar moiety provide resistance to nuclease degradation of an oligonucleotide in which they are incorporated. For example, methyleneoxy (4'-$CH_2$—O-2') BNA and other bicyclic sugar moiety analogs display duplex thermal stabilities with complementary DNA and RNA (Tm=+3 to +10° C.), stability towards 3'-exonucleolytic degradation and good solubility properties. Antisense oligonucleotides comprising BNAs have been described (Wahlestedt et al., *Proc. Natl. Acad. Sci. U.S.A.*, 2000, 97, 5633-5638).

Certain bicyclic-sugar moiety containing nucleosides (or BNA nucleosides) comprise a bridge linking the 4' carbon and the 2' carbon of the sugar moiety. In certain embodiments, the bridging group is a methyleneoxy (4'-$CH_2$—O-2'). In certain embodiments, the bridging group is an ethyleneoxy (4'-$CH_2CH_2$—O-2') (Singh et al., Chem. Commun., 1998, 4, 455-456: Morita et al., *Bioorganic Medicinal Chemistry*, 2003, 11, 2211-2226).

In certain embodiments, bicyclic sugar moieties of BNA nucleosides include, but are not limited to, compounds having at least one bridge between the 4' and the 2' position of the sugar moiety wherein such bridges independently comprises 1 or from 2 to 4 linked groups independently selected from —[C(R$_1$)(R$_2$)]$_n$—, —C(R$_1$)=C(R$_2$)—, —C(R$_1$)=N—, —C(=NR$_1$)—, —C(=O)—, —C(=S)—, —O—, —Si(R$_1$)$_2$—, —S(=O)$_x$— and —N(R$_1$)—;

wherein:

x is 0, 1, or 2;

n is 1, 2, 3, or 4;

each R$_1$ and R$_2$ is, independently, H, a protecting group, hydroxyl, C$_1$-C$_{12}$ alkyl, substituted C$_1$-C$_{12}$ alkyl, C$_2$-C$_{12}$ alkenyl, substituted C$_2$-C$_{12}$ alkenyl, C$_2$-C$_{12}$ alkynyl, substituted C$_2$-C$_{12}$ alkynyl, C$_5$-C$_{20}$ aryl, substituted C$_5$-C$_{20}$ aryl, heterocycle radical, substituted heterocycle radical, heteroaryl, substituted heteroaryl, C$_5$-C$_7$ alicyclic radical, substituted C$_5$-C$_7$ alicyclic radical, halogen, OJ$_1$, NJ$_1$J$_2$, SJ$_1$, N$_3$, COOJ$_1$, acyl (C(=O)—H), substituted acyl, CN, sulfonyl (S(=O)$_2$-J$_1$), or sulfoxyl (S(=O)-J$_1$); and each J$_1$ and J$_2$ is, independently, H, C$_1$-C$_{12}$ alkyl, substituted C$_1$-C$_{12}$ alkyl, C$_2$-C$_{12}$ alkenyl, substituted C$_2$-C$_{12}$ alkenyl, C$_2$-C$_{12}$ alkynyl, substituted C$_2$-C$_{12}$ alkynyl, C$_5$-C$_{20}$ aryl, substituted C$_5$-C$_{20}$ aryl, acyl (C(=O)—H), substituted acyl, a heterocycle radical, a substituted heterocycle radical, C$_1$-C$_{12}$ aminoalkyl, substituted C$_1$-C$_{12}$ aminoalkyl or a protecting group.

In certain embodiments, the bridge of a bicyclic sugar moiety is, —[C(R$_1$)(R$_2$)]$_n$—, —[C(R$_1$)(R$_2$)]$_n$—O—, —C(R$_1$R$_2$)—N(R$_1$)—O— or —C(R$_1$R$_2$)—O—N(R$_1$). In certain embodiments, the bridge is 4'-CH$_2$-2', 4'-(CH$_2$)$_2$-2', 4'-(CH$_2$)$_3$-2', 4'-CH$_2$-O-2', 4'-(CH$_2$)$_2$-O-2', 4'-CH$_2$-O—N(R$_1$)-2' and 4'-CH$_2$—N(R$_1$)—O-2'- wherein each R$_1$ is, independently, H, a protecting group or C$_1$-C$_{12}$ alkyl. In certain embodiments, bicyclic nucleosides are further defined by isomeric configuration. For example, a nucleoside comprising a 4'-2' methylenoxy bridge, may be in the α-L configuration or in the β-D configuration. Previously, alpha-L-methyleneoxy (4'-CH$_2$—O-2') BNA's have been incorporated into antisense oligonucleotides that showed antisense activity (Frieden et al., *Nucleic Acids Research*, 2003, 21, 6365-6372).

In certain embodiments, bicyclic nucleosides include, but are not limited to, (A) α-L-Methyleneoxy (4'-CH$_2$—O-2') BNA, (B) β-D-Methyleneoxy (4'-CH$_2$—O-2') BNA, (C) Ethyleneoxy (4'-(CH$_2$)$_2$—O-2') BNA, (D) Aminooxy (4'-CH$_2$—O—N(R)-2') BNA and (E) Oxyamino (4'-CH$_2$—N(R)—O-2') BNA, as depicted below.

(A)

(B)

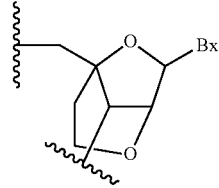

(C)

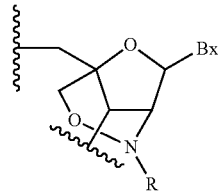

(D)

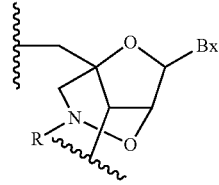

(E)

wherein Bx is the base moiety. In certain embodiments, bicyclic nucleosides include, but are not limited to, the structures below:

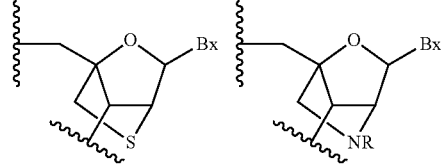

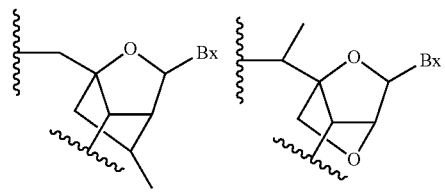

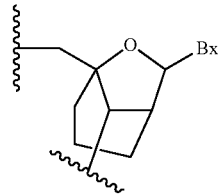

wherein Bx is the base moiety.

In certain embodiments, bicyclic nucleosides have the formula:

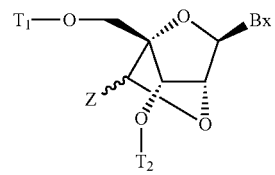

wherein:

Bx is a heterocyclic base moiety;

$T_1$ is H or a hydroxyl protecting group;

$T_2$ is H, a hydroxyl protecting group or a reactive phosphorus group;

Z is $C_1$-$C_6$ alkyl, $C_2$-$C_6$ alkenyl, $C_2$-$C_6$ alkynyl, substituted $C_1$-$C_6$ alkyl, substituted $C_2$-$C_6$ alkenyl, substituted $C_2$-$C_6$ alkynyl, acyl, substituted acyl, or substituted amide.

In one embodiment, each of the substituted groups, is, independently, mono or poly substituted with optionally protected substituent groups independently selected from halogen, oxo, hydroxyl, $OJ_1$, $NJ_1J_2$, $SJ_1$, $N_3$, $OC(=X)J_1$, $OC(=X)NJ_1J_2$, $NJ_3C(=X)NJ_1J_2$ and CN, wherein each $J_1$, $J_2$ and $J_3$ is, independently, H or $C_1$-$C_6$ alkyl, and X is O, S or $NJ_1$.

In certain such embodiments, each of the substituted groups, is, independently, mono or poly substituted with substituent groups independently selected from halogen, oxo, hydroxyl, $OJ_1$, $NJ_1J_2$, $SJ_1$, $N_3$, $OC(=X)J_1$, and $NJ_3C(=X)NJ_1J_2$, wherein each $J_1$, $J_2$ and $J_3$ is, independently, H, $C_1$-$C_6$ alkyl, or substituted $C_1$-$C_6$ alkyl and X is O or $NJ_1$.

In certain embodiments, the Z group is $C_1$-$C_6$ alkyl substituted with one or more $X^x$, wherein each $X^x$ is independently $OJ_1$, $NJ_1J_2$, $SJ_1$, $N_3$, $OC(=X)J_1$, $OC(=X)NJ_1J_2$, $NJ_3C(=X)NJ_1J_2$ or CN; wherein each $J_1$, $J_2$ and $J_3$ is, independently, H or $C_1$-$C_6$ alkyl, and X is O, S or $NJ_1$. In another embodiment, the Z group is $C_1$-$C_6$ alkyl substituted with one or more $X^x$, wherein each $X^x$ is independently halo (e.g., fluoro), hydroxyl, alkoxy (e.g., $CH_3O-$), substituted alkoxy or azido.

In certain embodiments, the Z group is $-CH_2X^x$, wherein $X^x$ is $OJ_1$, $NJ_1J_2$, $SJ_1$, $N_3$, $OC(=X)J_1$, $OC(=X)NJ_1J_2$, $NJ_3C(=X)NJ_1J_2$ or CN; wherein each $J_1$, $J_2$ and $J_3$ is, independently, H or $C_1$-$C_6$ alkyl, and X is O, S or $NJ_1$. In another embodiment, the Z group is $-CH_2X^x$, wherein $X^x$ is halo (e.g., fluoro), hydroxyl, alkoxy (e.g., $CH_3O-$) or azido.

In certain such embodiments, the Z group is in the (R)-configuration:

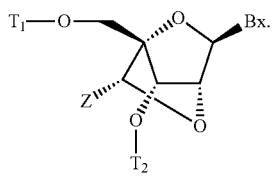

In certain such embodiments, the Z group is in the (S)-configuration:

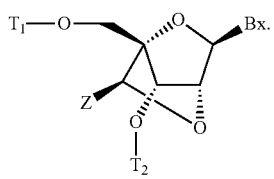

In certain embodiments, each $T_1$ and $T_2$ is a hydroxyl protecting group. A preferred list of hydroxyl protecting groups includes benzyl, benzoyl, 2,6-dichlorobenzyl, t-butyldimethylsilyl, t-butyldiphenylsilyl, mesylate, tosylate, dimethoxytrityl (DMT), 9-phenylxanthine-9-yl (Pixyl) and 9-(p-methoxyphenyl)xanthine-9-yl (MOX). In certain embodiments, $T_1$ is a hydroxyl protecting group selected from acetyl, benzyl, t-butyldimethylsilyl, t-butyldiphenylsilyl and dimethoxytrityl wherein a more preferred hydroxyl protecting group is $T_1$ is 4,4'-dimethoxytrityl.

In certain embodiments, $T_2$ is a reactive phosphorus group wherein preferred reactive phosphorus groups include diisopropylcyanoethoxy phosphoramidite and H-phosphonate. In certain embodiments $T_1$ is 4,4'-dimethoxytrityl and $T_2$ is diisopropylcyanoethoxy phosphoramidite.

In certain embodiments, oligomeric compounds have at least one monomer of the formula:

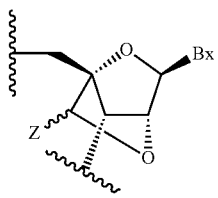

or of the formula:

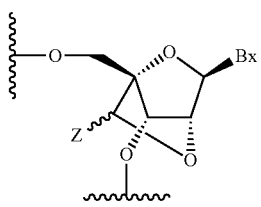

or of the formula:

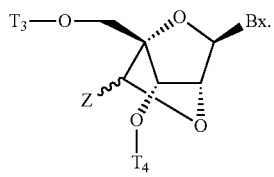

wherein

Bx is a heterocyclic base moiety;

$T_3$ is H, a hydroxyl protecting group, a linked conjugate group or an internucleoside linking group attached to a nucleoside, a nucleotide, an oligonucleoside, an oligonucleotide, a monomeric subunit or an oligomeric compound;

$T_4$ is H, a hydroxyl protecting group, a linked conjugate group or an internucleoside linking group attached to a nucleoside, a nucleotide, an oligonucleoside, an oligonucleotide, a monomeric subunit or an oligomeric compound;

wherein at least one of $T_3$ and $T_4$ is an internucleoside linking group attached to a nucleoside, a nucleotide, an oligonucleoside, an oligonucleotide, a monomeric subunit or an oligomeric compound; and Z is $C_1$-$C_6$ alkyl, $C_2$-$C_6$ alkenyl, $C_2$-$C_6$ alkynyl, substituted $C_1$-$C_6$ alkyl, substituted $C_2$-$C_6$ alkenyl, substituted $C_2$-$C_6$ alkynyl, acyl, substituted acyl, or substituted amide.

In one embodiment, each of the substituted groups, is, independently, mono or poly substituted with optionally protected substituent groups independently selected from halogen, oxo, hydroxyl, $OJ_1$, $NJ_1J_2$, $SJ_1$, $N_3$, $OC(=X)J_1$, $OC(=X)NJ_1J_2$, $NJ_3C(=X)NJ_1J_2$ and CN, wherein each $J_1$, $J_2$ and $J_3$ is, independently, H or $C_1$-$C_6$ alkyl, and X is O, S or $NJ_1$.

In one embodiment, each of the substituted groups, is, independently, mono or poly substituted with substituent groups independently selected from halogen, oxo, hydroxyl, $OJ_1$, $NJ_1J_2$, $SJ_1$, $N_3$, $OC(=X)J_1$, and $NJ_3C(=X)NJ_1J_2$, wherein each $J_1$, $J_2$ and $J_3$ is, independently, H or $C_1$-$C_6$ alkyl, and X is O or $NJ_1$.

In certain such embodiments, at least one Z is $C_1$-$C_6$ alkyl or substituted $C_1$-$C_6$ alkyl. In certain embodiments, each Z is, independently, $C_1$-$C_6$ alkyl or substituted $C_1$-$C_6$ alkyl. In certain embodiments, at least one Z is $C_1$-$C_6$ alkyl. In certain embodiments, each Z is, independently, $C_1$-$C_6$ alkyl. In certain embodiments, at least one Z is methyl. In certain embodiments, each Z is methyl. In certain embodiments, at least one Z is ethyl. In certain embodiments, each Z is ethyl. In certain embodiments, at least one Z is substituted $C_1$-$C_6$ alkyl. In certain embodiments, each Z is, independently, substituted $C_1$-$C_6$ alkyl. In certain embodiments, at least one Z is substituted methyl. In certain embodiments, each Z is substituted methyl. In certain embodiments, at least one Z is substituted ethyl. In certain embodiments, each Z is substituted ethyl.

In certain embodiments, at least one substituent group is $C_1$-$C_6$ alkoxy (e.g., at least one Z is $C_1$-$C_6$ alkyl substituted with one or more $C_1$-$C_6$ alkoxy). In another embodiment, each substituent group is, independently, $C_1$-$C_6$ alkoxy (e.g., each Z is, independently, $C_1$-$C_6$ alkyl substituted with one or more $C_1$-$C_6$ alkoxy).

In certain embodiments, at least one $C_1$-$C_6$ alkoxy substituent group is $CH_3O$— (e.g., at least one Z is $CH_3OCH_2$—). In another embodiment, each $C_1$-$C_6$ alkoxy substituent group is $CH_3O$— (e.g., each Z is $CH_3OCH_2$—).

In certain embodiments, at least one substituent group is halogen (e.g., at least one Z is $C_1$-$C_6$ alkyl substituted with one or more halogen). In certain embodiments, each substituent group is, independently, halogen (e.g., each Z is, independently, $C_1$-$C_6$ alkyl substituted with one or more halogen). In certain embodiments, at least one halogen substituent group is fluoro (e.g., at least one Z is $CH_2FCH_2$—, $CHF_2CH_2$— or $CF_3CH_2$—). In certain embodiments, each halo substituent group is fluoro (e.g., each Z is, independently, $CH_2FCH_2$—, $CHF_2CH_2$— or $CF_3CH_2$—).

In certain embodiments, at least one substituent group is hydroxyl (e.g., at least one Z is $C_1$-$C_6$ alkyl substituted with one or more hydroxyl). In certain embodiments, each substituent group is, independently, hydroxyl (e.g., each Z is, independently, $C_1$-$C_6$ alkyl substituted with one or more hydroxyl). In certain embodiments, at least one Z is $HOCH_2$—. In another embodiment, each Z is $HOCH_2$—.

In certain embodiments, at least one Z is $CH_3$—, $CH_3CH_2$—, $CH_2OCH_3$—, $CH_2F$— or $HOCH_2$—. In certain embodiments, each Z is, independently, $CH_3$—, $CH_3CH_2$—, $CH_2OCH_3$—, $CH_2F$— or $HOCH_2$—.

In certain embodiments, at least one Z group is $C_1$-$C_6$ alkyl substituted with one or more $X^x$, wherein each $X^x$ is, independently, $OJ_1$, $NJ_1J_2$, $SJ_1$, $N_3$, $OC(=X)J_1$, $OC(=X)NJ_1J_2$, $NJ_3C(=X)NJ_1J_2$ or CN; wherein each $J_1$, $J_2$ and $J_3$ is, independently, H or $C_1$-$C_6$ alkyl, and X is O, S or $NJ_1$. In another embodiment, at least one Z group is $C_1$-$C_6$ alkyl substituted with one or more $X^x$, wherein each $X^x$ is, independently, halo (e.g., fluoro), hydroxyl, alkoxy (e.g., $CH_3O$—) or azido.

In certain embodiments, each Z group is, independently, $C_1$-$C_6$ alkyl substituted with one or more $X^x$, wherein each $X^x$ is independently $OJ_1$, $NJ_1J_2$, $SJ_1$, $N_3$, $OC(=X)J_1OX(=X)NJ_1J_2$, $NJ_3C(=X)NJ_1J_2$ or CN; wherein each $J_1$, $J_2$ and $J_3$ is, independently, H or $C_1$-$C_6$ alkyl, and X is O, S or $NJ_1$. In another embodiment, each Z group is, independently, $C_1$-$C_6$ alkyl substituted with one or more $X^x$, wherein each $X^x$ is independently halo (e.g., fluoro), hydroxyl, alkoxy (e.g., $CH_3O$—) or azido.

In certain embodiments, at least one Z group is —$CH_2X^x$, wherein $X^x$ is $OJ_1$, $NJ_1J_2$, $SJ_1$, $N_3$, $OC(=X)J_1$, $OC(=X)NJ_1J_2$, $NJ_3C(=X)NJ_1J_2$ or CN; wherein each $J_1$, $J_2$ and $J_3$ is, independently, H or $C_1$-$C_6$ alkyl, and X is O, S or $NJ_1$ In certain embodiments, at least one Z group is —$CH_2X^x$, wherein $X^x$ is halo (e.g., fluoro), hydroxyl, alkoxy (e.g., $CH_3O$—) or azido.

In certain embodiments, each Z group is, independently, —$CH_2X^x$, wherein each $X^x$ is, independently, $OJ_1$, $NJ_1J_2$, $SJ_1$, $N_3$, $OC(=X)J_1$, $OC(=X)NJ_1J_2$, $NJ_3C(=X)NJ_1J_2$ or CN; wherein each $J_1$, $J_2$ and $J_3$ is, independently, H or $C_1$-$C_6$ alkyl, and X is O, S or $NJ_1$. In another embodiment, each Z group is, independently, —$CH_2X^x$, wherein each $X^x$ is, independently, halo (e.g., fluoro), hydroxyl, alkoxy (e.g., $CH_3O$—) or azido.

In certain embodiments, at least one Z is $CH_3$—. In another embodiment, each Z is, $CH_3$—.

In certain embodiments, the Z group of at least one monomer is in the (R)-configuration represented by the formula:

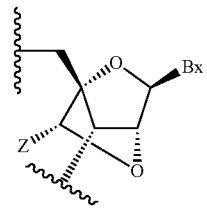

or the formula:

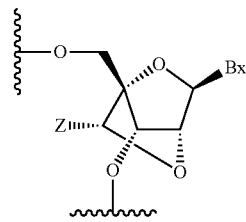

or the formula:

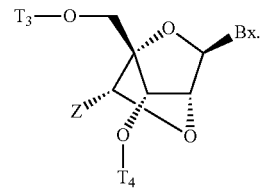

In certain embodiments, the Z group of each monomer of the formula is in the (R)-configuration.

In certain embodiments, the Z group of at least one monomer is in the (S)-configuration represented by the formula:

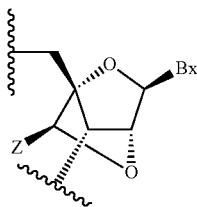

or the formula:

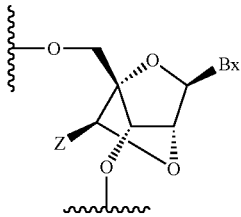

or the formula:

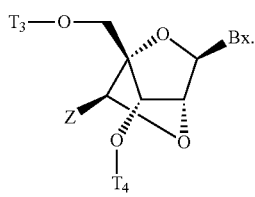

In certain embodiments, the Z group of each monomer of the formula is in the (S)-configuration.

In certain embodiments, $T_3$ is H or a hydroxyl protecting group. In certain embodiments, $T_4$ is H or a hydroxyl protecting group. In a further embodiment $T_3$ is an internucleoside linking group attached to a nucleoside, a nucleotide or a monomeric subunit. In certain embodiments, $T_4$ is an internucleoside linking group attached to a nucleoside, a nucleotide or a monomeric subunit. In certain embodiments, $T_3$ is an internucleoside linking group attached to an oligonucleoside or an oligonucleotide. In certain embodiments, $T_4$ is an internucleoside linking group attached to an oligonucleoside or an oligonucleotide. In certain embodiments, $T_3$ is an internucleoside linking group attached to an oligomeric compound. In certain embodiments, $T_4$ is an internucleoside linking group attached to an oligomeric compound. In certain embodiments, at least one of $T_3$ and $T_4$ comprises an internucleoside linking group selected from phosphodiester or phosphorothioate.

In certain embodiments, oligomeric compounds have at least one region of at least two contiguous monomers of the formula:

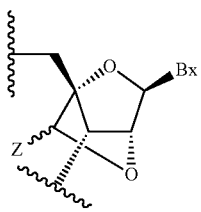

or of the formula:

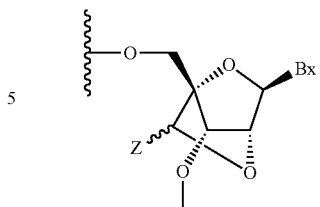

or of the formula:

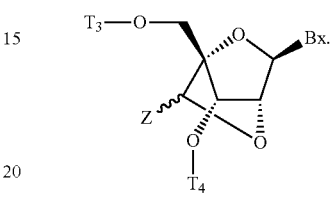

The synthesis and preparation of the methyleneoxy (4'-$CH_2$—O-2') BNA monomers adenine, cytosine, guanine, 5-methyl-cytosine, thymine and uracil, along with their oligomerization, and nucleic acid recognition properties have been described (Koshkin et al., Tetrahedron, 1998, 54, 3607-3630). BNAs and preparation thereof are also described in WO 98/39352 and WO 99/14226.

Analogs of methyleneoxy (4'-$CH_2$—O-2') BNA, phosphorothioate-methyleneoxy (4'-$CH_2$—O-2') BNA and 2'-thio-BNAs, have also been prepared (Kumar et al., Bioorg. Med. Chem. Lett., 1998, 8, 2219-2222). Preparation of locked nucleoside analogs comprising oligodeoxyribonucleotide duplexes as substrates for nucleic acid polymerases has also been described (Wengel et al., WO 99/14226). Furthermore, synthesis of 2'-amino-BNA, a novel comformationally restricted high-affinity oligonucleotide analog has been described in the art (Singh et al., J. Org. Chem., 1998, 63, 10035-10039). In addition, 2'-Amino- and 2'-methylamino-BNA's have been prepared and the thermal stability of their duplexes with complementary RNA and DNA strands has been previously reported.

Certain Non-Bicyclic Modified Sugar Moieties

In certain embodiments, the present invention provides modified nucleosides comprising modified sugar moieties that are not bicyclic sugar moieties. Certain such modified nucleosides are known. In certain embodiments, the sugar ring of a nucleoside may be modified at any position. Examples of sugar modifications useful in this invention include, but are not limited to compounds comprising a sugar substituent group selected from: OH; F; O-, S-, or N-alkyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. In certain such embodiments, such substituents are at the 2' position of the sugar.

In certain embodiments, modified nucleosides comprise a substituent at the 2' position of the sugar. In certain embodiments, such substituents are selected from among: a halide, including, but not limited to F; allyl, amino, azido, thio, O-allyl, O—C1-C10 alkyl, —OCF3, O—(CH2)2-O—CH3, 2'-O(CH2)2SCH3, O—(CH2)2-O—N(Rm)(Rn), or O—CH2-C(=O)—N(Rm)(Rn), where each Rm and Rn is, independently, H or substituted or unsubstituted C1-C10 alkyl.

In certain embodiments, modified nucleosides suitable for use in the present invention are: 2-methoxyethoxy (also known as 2'-O-methoxyethyl, 2'-MOE, or 2'-OCH$_2$CH$_2$OCH$_3$), 2'-O-methyl (2'-O—CH$_3$), 2'-fluoro (2'-F).

In one embodiment, modified nucleosides having a substituent group at the 2'-position selected from: O[CH$_2$)$_n$O]$_m$CH$_3$, O(CH$_2$)$_n$NH$_2$, O(CH$_2$)$_n$CH$_3$, O(CH$_2$)$_n$ONH$_2$, OCH$_2$C(=O)N(H)CH$_3$ and O(CH$_2$)$_n$ON[(CH$_2$)$_n$CH$_3$]$_2$, where n and m are from 1 to about 10. Other 2'-sugar substituent groups include: C$_1$ to C$_{10}$ alkyl, substituted alkyl, alkenyl, alkynyl, alkaryl, aralkyl, O-alkaryl or O-aralkyl, SH, SCH$_3$, OCN, Cl, Br, CN, CF$_3$, OCF$_3$, SOCH$_3$, SO$_2$CH$_3$, ONO$_2$, NO$_2$, N$_3$, NH$_2$, heterocycloalkyl, heterocycloalkaryl, aminoalkylamino, polyalkylamino, substituted silyl, an RNA cleaving group, a reporter group, an intercalator, a group for improving pharmacokinetic properties, or a group for improving the pharmacodynamic properties of an oligomeric compound, and other substituents having similar properties.

In certain embodiments, modified nucleosides comprise a 2'-MOE side chain (Baker et al., J. Biol. Chem., 1997, 272, 11944-12000). Such 2'-MOE substitution have been described as having improved binding affinity compared to unmodified nucleosides and to other modified nucleosides, such as 2'-O-methyl, O-propyl, and O-aminopropyl. Oligonucleotides having the 2'-MOE substituent also have been shown to be antisense inhibitors of gene expression with promising features for in vivo use (Martin, P., Hely. Chim. Acta, 1995, 78, 486-504; Altmann et al., Chimia, 1996, 50, 168-176; Altmann et al., Biochem. Soc. Trans., 1996, 24, 630-637; and Altmann et al., Nucleosides Nucleotides, 1997, 16, 917-926).

In certain embodiments, 2'-Sugar substituent groups are in either the arabino (up) position or ribo (down) position. In certain such embodiments, a 2'-arabino modification is 2'-F arabino (FANA). Similar modifications can also be made at other positions on the sugar, particularly the 3' position of the sugar on a 3' terminal nucleoside or in 2'-5' linked oligonucleotides and the 5' position of 5' terminal nucleotide.

In certain embodiment,s nucleosides suitable for use in the present invention have sugar mimetics such as cyclobutyl moieties in place of the pentofuranosyl sugar. Representative U.S. patents that teach the preparation of such modified sugar structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; 5,792,747; and 5,700,920, each of which is herein incorporated by reference in its entirety.

Certain Nucleobases

In certain embodiments, nucleosides of the present invention comprise unmodified nucleobases. In certain embodiments, nucleosides of the present invention comprise modifed nucleobases.

In certain embodiments, nucleobase modifications can impart nuclease stability, binding affinity or some other beneficial biological property to the oligomeric compounds. As used herein, "unmodified" or "natural" nucleobases include the purine bases adenine (A) and guanine (G), and the pyrimidine bases thymine (T), cytosine (C) and uracil (U). Modified nucleobases also referred to herein as heterocyclic base moieties include other synthetic and natural nucleobases, many examples of which such as 5-methylcytosine (5-me-C), 5-hydroxymethyl cytosine, 7-deazaguanine and 7-deazaadenine among others.

Heterocyclic base moieties can also include those in which the purine or pyrimidine base is replaced with other heterocycles, for example 7-deaza-adenine, 7-deazaguanosine, 2-aminopyridine and 2-pyridone. Certain modified nucleobases are disclosed in, for example, Swayze, E. E. and Bhat, B., The medicinal Chemistry of Oligonucleotides in ANTISENSE DRUG TECHNOLOGY, Chapter 6, pages 143-182 (Crooke, S. T., ed., 2008); U.S. Pat. No. 3,687,808, those disclosed in The Concise Encyclopedia Of Polymer Science And Engineering, pages 858-859, Kroschwitz, J. I., ed. John Wiley & Sons, 1990, those disclosed by Englisch et al., Angewandte Chemie, International Edition, 1991, 30, 613, and those disclosed by Sanghvi, Y. S., Chapter 15, Antisense Research and Applications, pages 289-302, Crooke, S. T. and Lebleu, B., ed., CRC Press, 1993. Certain of these nucleobases are particularly useful for increasing the binding affinity of the oligomeric compounds of the invention. These include 5-substituted pyrimidines, 6-azapyrimidines and N-2, N-6 and 0-6 substituted purines, including 2 aminopropyladenine, 5-propynyluracil and 5-propynylcytosine.

In certain embodiments, nucleobases comprise polycyclic heterocyclic compounds in place of one or more heterocyclic base moieties of a nucleobase. A number of tricyclic heterocyclic compounds have been previously reported. These compounds are routinely used in antisense applications to increase the binding properties of the modified strand to a target strand. The most studied modifications are targeted to guanosines hence they have been termed G-clamps or cytidine analogs.

Representative cytosine analogs that make 3 hydrogen bonds with a guanosine in a second strand include 1,3-diazaphenoxazine-2-one (R$_{10}$=O, R$_{11}$-R$_{14}$=H) (Kurchavov, et al., Nucleosides and Nucleotides, 1997, 16, 1837-1846), 1,3-diazaphenothiazine-2-one (R$_{10}$=S, R$_{11}$-R$_{14}$=H), (Lin, K.-Y.; Jones, R. J.; Matteucci, M. J. Am. Chem. Soc. 1995, 117, 3873-3874) and 6,7,8,9-tetrafluoro-1,3-diazaphenoxazine-2-one (R$_{10}$=O, R$_{11}$-R$_{14}$=F) (Wang, J.; Lin, K.-Y., Matteucci, M. Tetrahedron Lett. 1998, 39, 8385-8388). When incorporated into oligonucleotides, these base modifications have been shown to hybridize with complementary guanine and the latter was also shown to hybridize with adenine and to enhance helical thermal stability by extended stacking interactions (also see U.S. Patent Application Publication 20030207804 and U.S. Patent Application Publication 20030175906, both of which are incorporated herein by reference in their entirety).

Helix-stabilizing properties have been observed when a cytosine analog/substitute has an aminoethoxy moiety attached to the rigid 1,3-diazaphenoxazine-2-one scaffold (R$_{10}$=O, R$_{11}$=—O—(CH$_2$)$_2$—NH$_2$, R$_{12-14}$=H) (Lin, K.-Y.; Matteucci, M. J. Am. Chem. Soc. 1998, 120, 8531-8532). Binding studies demonstrated that a single incorporation could enhance the binding affinity of a model oligonucleotide to its complementary target DNA or RNA with a ΔT$_m$ of up to 18° relative to 5-methyl cytosine (dC5$^{me}$), which is the highest known affinity enhancement for a single modification. On the other hand, the gain in helical stability does not compromise the specificity of the oligonucleotides. The T$_m$ data indicate an even greater discrimination between the perfect match and mismatched sequences compared to dC5$^{me}$. It was suggested that the tethered amino group serves as an additional hydrogen bond donor to interact with the Hoogsteen face, namely the O6, of a complementary guanine thereby forming 4 hydrogen bonds. This means that the increased affinity of G-clamp is mediated by the combination of extended base stacking and additional specific hydrogen bonding.

Tricyclic heterocyclic compounds and methods of using them that are amenable to the present invention are disclosed in U.S. Pat. No. 6,028,183, and U.S. Pat. No. 6,007,992, the contents of both are incorporated herein in their entirety.

The enhanced binding affinity of the phenoxazine derivatives together with their sequence specificity makes them valuable nucleobase analogs for the development of more potent antisense-based drugs. The activity enhancement was even more pronounced in case of G-clamp, as a single substitution was shown to significantly improve the in vitro potency of a 20 mer 2'-deoxyphosphorothioate oligonucleotides (Flanagan, W. M.; Wolf, J. J.; Olson, P.; Grant, D.; Lin, K.-Y.; Wagner, R. W.; Matteucci, M. Proc. Natl. Acad. Sci. USA, 1999, 96, 3513-3518).

Modified polycyclic heterocyclic compounds useful as heterocyclic bases are disclosed in but not limited to, the above noted U.S. Pat. No. 3,687,808, as well as U.S. Pat. Nos. 4,845,205; 5,130,302; 5,134,066; 5,175,273; 5,367,066; 5,432,272; 5,434,257; 5,457,187; 5,459,255; 5,484,908; 5,502,177; 5,525,711; 5,552,540; 5,587,469; 5,594,121; 5,596,091; 5,614,617; 5,645,985; 5,646,269; 5,750,692; 5,830,653; 5,763,588; 6,005,096; and 5,681,941, and U.S. Patent Application Publication 20030158403, each of which is incorporated herein by reference in its entirety.

Certain nucleobase substitutions, including 5-methylcytosinse substitutions, have been shown to increase the binding affinity of oligonucleotides comprising them. For example, 5-methylcytosine substitutions have been shown to increase nucleic acid duplex stability by 0.6-1.2° C. (Sanghvi, Y. S., Crooke, S. T. and Lebleu, B., eds., *Antisense Research and Applications*, CRC Press, Boca Raton, 1993, pp. 276-278).

In certain embodiments, nucleosides of the present invention comprise unmodified pyrimidine nucleobases. In certain embodiments, nucleosides of the present invention are selected from Formula I and Formula II below:

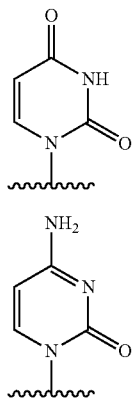

Formula I represents an unmodified uracil. Formula II represents an unmodified cytosine. In certain embodiments, nucleosides comprise modified sugar moieties and unmodified uracil or cytosine nucleobases.

Certain Nucleosides

In certain embodiments, the present invention provides oligonucleotides comprising nucleosides comprising any of the above described sugar moieties with any of the above described nucleobases. In certain embodiments, the invention provides nucleosides comprising a bicyclic sugar moiety and an unmodified pyrimidine nucleobase. In certain such embodiments, the bicyclic sugar moiety is a 4'-2' bicyclic sugar moiety. In certain embodiments, the sugar moiety is sugar moiety having the following Formula:

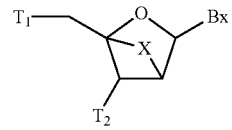

wherein independently for each of the at least one bicyclic nucleoside of formula III:

X is selected from among: 4'-$(CR_1R_2)_n$—Y-2';

wherein each $R^1$ and each $R^2$ is independently selected from among: hydrogen, a halogen, an optionally substituted $C_1$-$C_5$ alkyl, an optionally substituted $C_1$-$C_5$ alkenyl, an optionally substituted $C_1$-$C_5$ alkynyl, an optionally substituted heteroalkyl, an optionally substituted heteroalkenyl, and an optionally substituted heteroalkynyl;

Y is selected from among $CR_1R_2$, O, N(J), and S;

$T_1$ and $T_2$ are each, independently, an internucleoside linking group linking the bicyclic nucleoside to the oligonucleotide or one of $T_1$ and $T_2$ is an internucleoside linking group linking the bicyclic nucleoside to the oligonucleotide and the other of $T_1$ and $T_2$ is hydroxyl, a protected hydroxyl, a linked conjugate group or a 5' or 3'-terminal group;

n is from 1 to 3;

J is H, hydrogen, a halogen, an optionally substituted $C_1$-$C_5$ alkyl, an optionally substituted $C_1$-$C_5$ alkenyl, an optionally substituted $C_1$-$C_5$ alkynyl, an optionally substituted heteroalkyl, an optionally substituted heteroalkenyl, and an optionally substituted heteroalkynyl; and Bx is an unmodified pyrimidine.

Certain Internucleoside Linkages

In such embodiments, nucleosides may be linked together using any internucleoside linkage. The two main classes of internucleoside linking groups are defined by the presence or absence of a phosphorus atom. Representative phosphorus containing internucleoside linkages include, but are not limited to, phosphodiesters (P=O), phosphotriesters, methylphosphonates, phosphoramidate, and phosphorothioates (P=S). Representative non-phosphorus containing internucleoside linking groups include, but are not limited to, methylenemethylimino (—$CH_2$—$N(CH_3)$—O—$CH_2$—), thiodiester (—O—C(O)—S—), thionocarbamate (—O—C(O)(NH)—S—); siloxane (—O—Si(H)2-O—); and N,N'-dimethylhydrazine (—$CH_2$—$N(CH_3)$—$N(CH_3)$—). Oligonucleotides having non-phosphorus internucleoside linking groups may be referred to as oligonucleosides. Modified linkages, compared to natural phosphodiester linkages, can be used to alter, typically increase, nuclease resistance of the oligomeric compound. In certain embodiments, internucleoside linkages having a chiral atom can be prepared a racemic mixtures, as separate enantiomers. Representative chiral linkages include, but are not limited to, alkylphosphonates and phosphorothioates. Methods of preparation of phosphorous-containing and non-phosphorous-containing internucleoside linkages are well known to those skilled in the art.

The oligomeric compounds described herein contain one or more asymmetric centers and thus give rise to enantiomers, diastereomers, and other stereoisomeric configurations that may be defined, in terms of absolute stereochemistry, as (R) or (S), α or β such as for sugar anomers, or as (D) or (L) such as for amino acids et al. Included in the antisense compounds provided herein are all such possible isomers, as well as their racemic and optically pure forms.

Certain Oligonucleotides

In certain embodiments, the present invention provides oligonucleotides comprising linked nucleosides. In certain embodiments, any of the nucleosides described above can be linked using any of the linkages described above to generate oligonucleotides.

In certain embodiments, oligonucleotides of the present invention comprise at least one nucleoside comprising a modified sugar and an unmodified pyrimidine nucleobase. In certain embodiments, oligonucleotides of the present invention comprise at least one nucleoside comprising a bicyclic sugar and an unmodified cytosine or uracil nucleobase.

In certain embodiments, the present invention provides chimeric oligomeric compounds. In certain such embodiments, chimeric oligomeric compounds are chimeric oligonucleotides. In certain such embodiments, the chimeric oligonucleotides comprise differently modified nucleotides. In certain embodiments, chimeric oligonucleotides are mixed-backbone antisense oligonucleotides.

In general a chimeric oligomeric compound have modified nucleosides that can be in isolated positions or grouped together in regions that will define a particular motif. Any combination of modifications and/or mimetic groups can comprise a chimeric oligomeric compound as described herein.

In certain embodiments, chimeric oligomeric compounds typically comprise at least one region modified so as to confer increased resistance to nuclease degradation, increased cellular uptake, and/or increased binding affinity for the target nucleic acid. In certain embodiments, an additional region of the oligomeric compound may serve as a substrate for enzymes capable of cleaving RNA:DNA or RNA:RNA hybrids.

In certain embodiments, the present invention provides oligonucleotides of any of a variety of ranges of lengths. In certain embodiments, the invention provides oligonucleotides and/or oligomeric compounds consisting of X—Y linked oligonucleosides, where X and Y are each independently selected from 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and 50; provided that X<Y. For example, in certain embodiments, the invention provides oligonucleotides and/or oligomeric compounds consisting of: 8-9, 8-10, 8-11, 8-12, 8-13, 8-14, 8-15, 8-16, 8-17, 8-18, 8-19, 8-20, 8-21, 8-22, 8-23, 8-24, 8-25, 8-26, 8-27, 8-28, 8-29, 8-30, 9-10, 9-11, 9-12, 9-13, 9-14, 9-15, 9-16, 9-17, 9-18, 9-19, 9-20, 9-21, 9-22, 9-23, 9-24, 9-25, 9-26, 9-27, 9-28, 9-29, 9-30, 10-11, 10-12, 10-13, 10-14, 10-15, 10-16, 10-17, 10-18, 10-19, 10-20, 10-21, 10-22, 10-23, 10-24, 10-25, 10-26, 10-27, 10-28, 10-29, 10-30, 11-12, 11-13, 11-14, 11-15, 11-16, 11-17, 11-18, 11-19, 11-20, 11-21, 11-22, 11-23, 11-24, 11-25, 11-26, 11-27, 11-28, 11-29, 11-30, 12-13, 12-14, 12-15, 12-16, 12-17, 12-18, 12-19, 12-20, 12-21, 12-22, 12-23, 12-24, 12-25, 12-26, 12-27, 12-28, 12-29, 12-30, 13-14, 13-15, 13-16, 13-17, 13-18, 13-19, 13-20, 13-21, 13-22, 13-23, 13-24, 13-25, 13-26, 13-27, 13-28, 13-29, 13-30, 14-15, 14-16, 14-17, 14-18, 14-19, 14-20, 14-21, 14-22, 14-23, 14-24, 14-25, 14-26, 14-27, 14-28, 14-29, 14-30, 15-16, 15-17, 15-18, 15-19, 15-20, 15-21, 15-22, 15-23, 15-24, 15-25, 15-26, 15-27, 15-28, 15-29, 15-30, 16-17, 16-18, 16-19, 16-20, 16-21, 16-22, 16-23, 16-24, 16-25, 16-26, 16-27, 16-28, 16-29, 16-30, 17-18, 17-19, 17-20, 17-21, 17-22, 17-23, 17-24, 17-25, 17-26, 17-27, 17-28, 17-29, 17-30, 18-19, 18-20, 18-21, 18-22, 18-23, 18-24, 18-25, 18-26, 18-27, 18-28, 18-29, 18-30, 19-20, 19-21, 19-22, 19-23, 19-24, 19-25, 19-26, 19-29, 19-28, 19-29, 19-30, 20-21, 20-22, 20-23, 20-24, 20-25, 20-26, 20-27, 20-28, 20-29, 20-30, 21-22, 21-23, 21-24, 21-25, 21-26, 21-27, 21-28, 21-29, 21-30, 22-23, 22-24, 22-25, 22-26, 22-27, 22-28, 22-29, 22-30, 23-24, 23-25, 23-26, 23-27, 23-28, 23-29, 23-30, 24-25, 24-26, 24-27, 24-28, 24-29, 24-30, 25-26, 25-27, 25-28, 25-29, 25-30, 26-27, 26-28, 26-29, 26-30, 27-28, 27-29, 27-30, 28-29, 28-30, or 29-30 linked nucleosides.

Certain Chemical Motifs

In certain embodiments oligonucleotides of the present invention may be described by their chemical motif. Certain chemical motifs are known in the art.

In certain embodiments, oligonucleotids of the present invention are fully modified motif. In certain embodiments, such fully modified oligonucleotides are uniformly modified, wherein each nucleoside is comprises the same modified bicyclic sugar moiety.

In certain embodiments, oligonucleotides of the present invention have blockmer motif. In certain such embodiments, oligonucleotides of the present invention comprise a sequence of β-D-ribonucleosides or β-D-deoxyribonucleosides having one internal block of from 2 to 6, or from 2 to 4 sugar modified nucleosides. The internal block region can be at any position within the oligomeric compound as long as it is not at one of the termini which would then make it a hemimer. The base sequence and internucleoside linkages can vary at any position within a blockmer motif.

In certain embodiments, the present invention provides gapmers. In certain such embodiments, the wings of such gapmers comprise the same modification as one another (a symmetric gapmer). In certain embodiments, the wings of the gapmer comprise modifications that are different from one another (asymmetric gapmer).

In certain embodiments, the invention provides gapmers comprising at least one nucleoside comprising a bicyclic sugar moiety and an unmodified cytosine or uracil nucleobase. In certain embodiments, such nucleoside is in one or both wings of the gapmer. In certain such embodiments, the gap of the gapmer comprises unmodified deoxyribonucleosides and/or ribonucleosides. In certain such embodiments, one or more of the linkages is modified. In certain such embodiments, all of the linkages are modified.

In certain embodiments, a wing of a gapmer consists of 1-5 nucleosides. In certain embodiments, a wing of a gapmer consists of 1-4 nucleosides. In certain embodiments, a wing of a gapmer consists of 1-3 nucleosides. In certain embodiments, a wing of a gapmer consists of 1-2 nucleosides. In certain embodiments, a wing of a gapmer consists of one nucleoside. In certain embodiments, each wing of a gapmer comprises the same number of nucleosides. In certain embodiments, one wing of a gapmer comprises a different number of nucleosides than the other wing of the gapmer. In certain embodiments, the gap region of a gapmer consists of 5 to 23 nucleosides. In certain embodiments, the gap region of a gapmer consists of X to Y nucleosides, where X and Y are each independently selected from 6, 7, 8, 9, 10, 11, 12, 13, 14, 15, 16, 17, 18, 19, 20, 21, 22, 23; provided that X≤Y.

In certain embodiments, oligonuculeotides of the present invention are hemimers wherein chemical modifications to sugar moieties and/or internucleoside linkage distinguish a region of subunits at the 5' terminus from a region of subunits at the 3' terminus of the oligomeric compound. In certain such embodiments one of the 5'-end or the 3'-end has a sequence of from 2 to 12 nucleosides that are sugar modified nucleosides that are different from the other nucleosides in the hemimer modified oligomeric compound. An example of a typical hemimer is an oligomeric compound comprising β-D-ribonucleosides or β-D-deoxyribonucleosides that have a sequence of sugar modified nucleosides at one of the termini. One hemimer motif includes a sequence of β-D-ribonucleosides or β-D-deoxyribonucleosides having from 2-12 sugar modified nucleosides located at one of the termini. Another hemimer motif includes a sequence of β-D-ribonucleosides or β-D-deoxyribonucleosides having from 2-6 sugar modified nucleosides located at one of the termini with from 2-4 being suitable. In certain embodiments, β-D-deoxyribonucleosides comprise less than 13 contiguous nucleotides within the oligomeric compound. Such hemimer oligomeric compounds may comprise phosphodiester internucleotide linkages, phosphorothioate internucleotide linkages, or a combination of phosphodiester and phosphorothioate internucleotide linkages.

In certain embodiments, oligonucleotides of the present invention are positionally modified. Such positionally modified oligonucleotides comprise one or more region of uniformly modified nucleosides wherein the sequence is interrupted by two or more regions of 1 to about 8 differently modified nucleosides. The positionally modified motif includes internal regions of sugar modified nucleoside and can also include one or both termini. Each particular modification within a region of modified nucleosides essentially uniform. In certain embodiments, the nucleosides of regions are distinguished by differing sugar modifications. Positionally modified motifs are not determined by the nucleobase sequence or the location or types of internucleoside linkages. The term positionally modified oligomeric compound includes many different specific substitution patterns. In certain embodiments, positionally modified oligonucleotides have clusters of a first modification interspersed with a second modification, as follows 5'-MMmmMmMMMmmmmMMMMmmmmm-3'; and 5'-MMmMMmMMmMMmMMmMMmMMmMM-3'; wherein "M" represent the first modification, and "m" represents the second modification. For example, in certain embodiments, "M" could be 2'-MOE and "m" could be a bicyclic nucldoeside having a 4'-(CH$_2$)$_n$—O-2' where n is 1 or 2.

In certain embodiments, oligonucleotides of the present invention may have an alternating motif, which comprise two different types of nucleosides modification in alternating regions for essentially the entire sequence of the oligonucleotide. For example, in certain embodiments, the pattern of alternation can be described by the formula: 5'-A(-L-B-L-A)n(-L-B)nn-3' where A and B are nucleosides differentiated by having at least different sugar groups, each L is an internucleoside linking group, nn is 0 or 1 and n is from about 7 to about 11. This permits alternating oligomeric compounds from about 17 to about 24 nucleosides in length. This length range is not meant to be limiting as longer and shorter oligomeric compounds are also amenable to the present invention. This formula also allows for even and odd lengths for alternating oligomeric compounds wherein the 3' and 5'-terminal nucleosides are the same (odd) or different (even). These alternating oligomeric compounds may comprise phosphodiester internucleotide linkages, phosphorothioate internucleotide linkages, or a combination of phosphodiester and phosphorothioate internucleotide linkages.

The "A" and "B" nucleosides comprising alternating oligomeric compounds of the present invention are differentiated from each other by having at least different sugar moieties. Each of the A and B nucleosides has a modified sugar moiety selected from β-D-ribonucleosides, β-D-deoxyribonucleosides, 2'-modified nucleosides (such 2'-modified nucleosides may include 2'-MOE, 2'-fluoro, and 2'-O—CH3, among others), and bicyclic sugar modified nucleosides. The alternating motif is independent from the nucleobase sequence and the internucleoside linkages. The internucleoside linkage can vary at each position or at particular selected positions or can be uniform or alternating throughout the oligomeric compound.

Oligomeric Compounds

In certain embodiments, the present invention provides oligomeric compounds. In certain embodiments, oligomeric compounds comprise an oligonucleotide. In certain embodiments, an oligomeric compound comprises one or more conjugate and/or terminal group.

Such conjugate and/or terminal groups may be added to oligomeric compounds having any of the chemical motifs discussed above. Thus, for example, an oligomeric compound comprising a hemimer oligonucleotide may comprise a terminal group on the same terminal end as the block defining the hemimer and or at the other terminal end of the hemimer oligonucleotide.

Certain Conjugate Groups

In certain embodiments, oligomeric compounds are modified by attachment of one or more conjugate groups. In general, conjugate groups modify one or more properties of the attached oligomeric compound including but not limited to pharmacodynamics, pharmacokinetics, stability, binding, absorption, cellular distribution, cellular uptake, charge and clearance. Conjugate groups are routinely used in the chemical arts and are linked directly or via an optional conjugate linking moiety or conjugate linking group to a parent compound such as an oligomeric compound, such as an oligonucleotide. Conjugate groups includes without limitation, intercalators, reporter molecules, polyamines, polyamides, polyethylene glycols, thioethers, polyethers, cholesterols, thiocholesterols, cholic acid moieties, folate, lipids, phospholipids, biotin, phenazine, phenanthridine, anthraquinone, adamantane, acridine, fluoresceins, rhodamines, coumarins and dyes. Certain conjugate groups have been described previously, for example: cholesterol moiety (Letsinger et al., Proc. Natl. Acad. Sci. USA, 1989, 86, 6553-6556), cholic acid (Manoharan et al., Bioorg. Med. Chem. Let., 1994, 4, 1053-1060), a thioether, e.g., hexyl-S-tritylthiol (Manoharan et al., Ann. N.Y. Acad. Sci., 1992, 660, 306-309; Manoharan et al., Bioorg. Med. Chem. Let., 1993, 3, 2765-2770), a thiocholesterol (Oberhauser et al., Nucl. Acids Res., 1992, 20, 533-538), an aliphatic chain, e.g., do-decan-diol or undecyl residues (Saison-Behmoaras et al., EMBO J., 1991, 10, 1111-1118; Kabanov et al., FEBS Lett., 1990, 259, 327-330; Svinarchuk et al., Biochimie, 1993, 75, 49-54), a phospholipid, e.g., di-hexadecyl-rac-glycerol or triethyl-ammonium 1,2-di-O-hexadecyl-rac-glycero-3-H-phosphonate (Manoharan et al., Tetrahedron Lett., 1995, 36, 3651-3654; Shea et al., Nucl. Acids Res., 1990, 18, 3777-3783), a polyamine or a polyethylene glycol chain (Manoharan et al., Nucleosides & Nucleotides, 1995, 14, 969-973), or adamantane acetic acid (Manoharan et al., Tetrahedron Lett., 1995, 36, 3651-3654), a palmityl moiety (Mishra et al., Biochim. Biophys. Acta, 1995, 1264, 229-237), or an octadecylamine or hexylaminocarbonyl-oxycholesterol moiety (Crooke et al., J. Pharmacol. Exp. Ther., 1996, 277, 923-937).

In certain embodiments, a conjugate group comprises an active drug substance, for example, aspirin, warfarin, phenylbutazone, ibuprofen, suprofen, fen-bufen, ketoprofen, (S)-(+)-pranoprofen, carprofen, dansylsarcosine, 2,3,5-triiodobenzoic acid, flufenamic acid, folinic acid, a benzothiadiazide, chlorothiazide, a diazepine, indo-methicin, a barbiturate, a cephalosporin, a sulfa drug, an antidiabetic, an antibacterial or an antibiotic. Oligonucleotide-drug conjugates and their preparation are described in U.S. patent application Ser. No. 09/334,130.

Representative U.S. patents that teach the preparation of oligonucleotide conjugates include, but are not limited to, U.S. Pat. Nos. 4,828,979; 4,948,882; 5,218,105; 5,525,465; 5,541,313; 5,545,730; 5,552,538; 5,578,717; 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241, 5,391,723; 5,416,203, 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941.

In certain embodiments, conjugate groups are directly attached to oligonucleotides in oligomeric compounds. In certain embodiments, conjugate groups are attached to oligonucleotides by a conjugate linking group. In certain such embodiments, conjugate linking groups, including, but not limited to, bifunctional linking moieties such as those known in the art are amenable to the compounds provided herein. Conjugate linking groups are useful for attachment of conjugate groups, such as chemical stabilizing groups, functional groups, reporter groups and other groups to selective sites in a parent compound such as for example an oligomeric compound. In general a bifunctional linking moiety comprises a hydrocarbyl moiety having two functional groups. One of the functional groups is selected to bind to a parent molecule or compound of interest and the other is selected to bind essentially any selected group such as chemical functional group or a conjugate group. In some embodiments, the conjugate linker comprises a chain structure or an oligomer of repeating units such as ethylene glycol or amino acid units. Examples of functional groups that are routinely used in a bifunctional linking moiety include, but are not limited to, electrophiles for reacting with nucleophilic groups and nucleophiles for reacting with electrophilic groups. In some embodiments, bifunctional linking moieties include amino, hydroxyl, carboxylic acid, thiol, unsaturations (e.g., double or triple bonds), and the like.

Some nonlimiting examples of conjugate linking moieties include pyrrolidine, 8-amino-3,6-dioxaoctanoic acid (ADO), succinimidyl 4-(N-maleimidomethyl) cyclohexane-l-carboxylate (SMCC) and 6-aminohexanoic acid (AHEX or AHA). Other linking groups include, but are not limited to, substituted C1-C10 alkyl, substituted or unsubstituted C2-C10 alkenyl or substituted or unsubstituted C2-C10 alkynyl, wherein a nonlimiting list of preferred substituent groups includes hydroxyl, amino, alkoxy, carboxy, benzyl, phenyl, nitro, thiol, thioalkoxy, halogen, alkyl, aryl, alkenyl and alkynyl.

Conjugate groups may be attached to either or both ends of an oligonucleotide (terminal conjugate groups) and/or at any internal position.

Terminal Groups

In certain embodiments, oligomeric compounds comprise terminal groups at one or both ends. In certain embodiments, a terminal group may comprise any of the conjugate groups discussed above. In certain embodiments, terminal groups may comprise additional nucleosides and/or inverted abasic nucleosides. In certain embodiments, a terminal group is a stabilizing group.

In certain embodiments, oligomeric compounds comprise one or more terminal stabilizing group that enhances properties such as for example nuclease stability. Included in stabilizing groups are cap structures. The terms "cap structure" or "terminal cap moiety," as used herein, refer to chemical modifications, which can be attached to one or both of the termini of an oligomeric compound. These terminal modifications protect the oligomeric compounds having terminal nucleic acid moieties from exonuclease degradation, and can help in delivery and/or localization within a cell. The cap can be present at the 5'-terminus (5'-cap) or at the 3'-terminus (3'-cap) or can be present on both termini. In non-limiting examples, the 5'-cap includes inverted abasic residue (moiety), 4',5'-methylene nucleotide; 1-(beta-D-erythrofuranosyl) nucleotide, 4'-thio nucleotide, carbocyclic nucleotide; 1,5-anhydrohexitol nucleotide; L-nucleotides; alpha-nucleotides; modified base nucleotide; phosphorodithioate linkage; threo-pentofuranosyl nucleotide; acyclic 3',4'-seco nucleotide; acyclic 3,4-dihydroxybutyl nucleotide; acyclic 3,5-dihydroxypentyl riucleotide, 3'-3'-inverted nucleotide moiety; 3'-3'-inverted abasic moiety; 3'-2'-inverted nucleotide moiety; 3'-2'-inverted abasic moiety; 1,4-butanediol phosphate; 3'-phosphoramidate; hexylphosphate; aminohexyl phosphate; 3'-phosphate; 3'-phosphorothioate; phosphorodithioate; or bridging or non-bridging methylphosphonate moiety (for more details see Wincott et al., International PCT publication No. WO 97/26270).

Particularly suitable 3'-cap structures of the present invention include, for example 4',5'-methylene nucleotide; 1-(beta-D-erythrofuranosyl) nucleotide; 4'-thio nucleotide, carbocyclic nucleotide; 5'-amino-alkyl phosphate; 1,3-diamino-2-propyl phosphate, 3-aminopropyl phosphate; 6-aminohexyl phosphate; 1,2-aminododecyl phosphate; hydroxypropyl phosphate; 1,5-anhydrohexitol nucleotide; L-nucleotide; alpha-nucleotide; modified base nucleotide; phosphorodithioate; threo-pentofuranosyl nucleotide; acyclic 3',4'-seco nucleotide; 3,4-dihydroxybutyl nucleotide; 3,5-dihydroxy-pentyl nucleotide, 5'-5'-inverted nucleotide moiety; 5'-5'-inverted abasic moiety; 5'-phosphoramidate; 5'-phosphorothioate; 1,4-butanediol phosphate; 5'-amino; bridging and/or non-bridging 5'-phosphoramidate, phosphorothioate and/or phosphorodithioate, bridging or non bridging methylphosphonate and 5'-mercapto moieties (for more details see Beaucage and Tyer, 1993, Tetrahedron 49, 1925 and Published U.S. Patent Application Publication No. US 2005/0020525 published on Jan. 27, 2005). Further 3' and 5'-stabilizing groups that can be used to cap one or both ends of an oligomeric compound to impart nuclease stability include those disclosed in WO 03/004602.

Additional Nucleosides

In certain embodiments, one or more additional nucleosides is added to one or both terminal ends of an oligonucleotide or an oligomeric compound. In a double-stranded compound, such additional nucleosides are terminal (3' and/or 5') overhangs. In the setting of double-stranded antisense compounds, such additional nucleosides may or may not be complementary to a target nucleic acid. In a single-stranded antisense oligomeric compound, additional nucleosides are non-hybridizing terminal nucleosides.

Synthesis, Purification and Analysis

Oligomerization of modified and unmodified nucleosides and nucleotides can be routinely performed according to literature procedures for DNA (Protocols for Oligonucleotides and Analogs, Ed. Agrawal (1993), Humana Press) and/or RNA (Scaringe, Methods (2001), 23, 206-217. Gait et al., Applications of Chemically synthesized RNA in RNA: Protein Interactions, Ed. Smith (1998), 1-36. Gallo et al., Tetrahedron (2001), 57, 5707-5713).

Oligomeric compounds provided herein can be conveniently and routinely made through the well-known technique of solid phase synthesis. Equipment for such synthesis is sold by several vendors including, for example, Applied Biosystems (Foster City, Calif.). Any other means for such synthesis known in the art may additionally or alternatively be employed. It is well known to use similar techniques to prepare oligonucleotides such as the phosphorothioates and alkylated derivatives. The invention is not limited by the method of antisense compound synthesis.

Methods of purification and analysis of oligomeric compounds are known to those skilled in the art. Analysis methods include capillary electrophoresis (CE) and electrospray-mass spectroscopy. Such synthesis and analysis methods can be performed in multi-well plates. The method of the invention is not limited by the method of oligomer purification.

Antisense

In certain embodiments, oligomeric compounds of the present invention are antisense compounds. In such embodiments, the oligomeric compound is complementary to a target nucleic acid. In certain embodiments, a target nucleic acid is selected from a mRNA, a pre-mRNA, a microRNA, a non-coding RNA, including small non-coding RNA, and a promoter-directed RNA, each of which has been described.

Antisense mechanisms include any mechanism involving the hybridization of an oligomeric compound with target nucleic acid, wherein the hybridization results in a biological effect. In certain embodiments, such hybridization results in either target nucleic acid degradation or occupancy with concomitant stalling of the cellular machinery involving, for example, translation, transcription or splicing.

One type of antisense mechanism involving degradation of target RNA is RNase H mediated antisense. RNase H is a cellular endonuclease which cleaves the RNA strand of an RNA:DNA duplex. It is known in the art that single-stranded antisense compounds which are "DNA-like" elicit RNase H activity in mammalian cells. Activation of RNase H, therefore, results in cleavage of the RNA target, thereby greatly enhancing the efficiency of DNA-like oligonucleotide-mediated inhibition of gene expression.

Antisense mechanism also include, without limitation siRNA and RNAi mechanism. In certain instances, such mechanisms utilize the RISC pathway.

Antisense mechanism also include, without limitation microRNA mechanism. Such mechanism include creation of a microRNA mimic and/or an anti-microRNA.

Antisense mechanisms also include, without limitation, mechanisms that hybridize or mimic non-coding RNA other than microRNA or mRNA. Such non-coding RNA includes, but is not limited to promoter-directed RNA and short and long RNA that effects transcription or translation of one or more nucleic acids.

In certain embodiments, antisense compounds specifically hybridize when there is a sufficient degree of complementarity to avoid non-specific binding of the antisense compound to non-target nucleic acid sequences under conditions in which specific binding is desired, i.e., under physiological conditions in the case of in vivo assays or therapeutic treatment, and under conditions in which assays are performed in the case of in vitro assays.

As used herein, "stringent hybridization conditions" or "stringent conditions" refers to conditions under which an antisense compound will hybridize to its target sequence, but to a minimal number of other sequences. Stringent conditions are sequence-dependent and will be different in different circumstances, and "stringent conditions" under which antisense compounds hybridize to a target sequence are determined by the nature and composition of the antisense compounds and the assays in which they are being investigated.

It is understood in the art that incorporation of nucleotide affinity modifications may allow for a greater number of mismatches compared to an unmodified compound. Similarly, certain oligonucleotide sequences may be more tolerant to mismatches than other oligonucleotide sequences. One of ordinary skill in the art is capable of determining an appropriate number of mismatches between oligonucleotides, or between an oligonucleotide and a target nucleic acid, such as by determining melting temperature ($T_m$). $T_m$ or $\Delta T_m$ can be calculated by techniques that are familiar to one of ordinary skill in the art. For example, techniques described in Freier et al. (*Nucleic Acids Research*, 1997, 25, 22: 4429-4443) allow one of ordinary skill in the art to evaluate nucleotide modifications for their ability to increase the melting temperature of an RNA:DNA duplex.

Certain Bicyclic Nucleoside Containing Compounds

Oligomeric compounds for use as antisense compounds often comprise pyrimidine nucleobases that are modified to include a methyl at the C5 position (5-methyl pyrimidines). It has been reported that such methyl modification at this position improves affinity. See e.g., *Antisense Drug Technology*, Second Edition, Crooke, Ed., page 165. It has also been reported that in certain circumstances, such modification decreases toxicity. See, for example, Henry et al., *Chemically modified Oligonucleotides Exhibit Decreases Immune Stimulation in Mice*, J. of Phamacology and Experimental Therapeutics, 292(2) 468-479 (2000). Since this modification is reported to both improve affinity and reduce toxicity, most reported antisense oligomeric compounds comprise C5 methylated pyrimidines: 5-methyl cytosine and 5-methyl uracil (thymine).

In certain embodiments, the present invention provides oligomeric compounds comprising at least one nucleoside comprising a bicyclic sugar moiety and an unmodified cytosine or uracil. In certain embodiments, such oligomeric compounds do not comprise any nucleosides comprising a bicyclic sugar moiety and a 5-methyl cytosine or 5-methyl uracil (thymine).

Certain oligomeric compounds comprising one or more bicyclic nucleoside have been shown to have improved affinity for a target nucleic acid, relative to oligomeric compounds having different modifications or no modifications. It has also been shown that certain such oligomeric compounds have improved in vitro and in vivo potency compared to oligomeric compounds having different modifications or no modifications. However, it has also been shown that such compounds have increased toxicity when administered to animals, compared to those differently modified oligomeric compounds. See, e.g., Swayze, E. E., et al., *Antisense oligonucleotides containing locked nucleic acid improve potency but cause significant hepatotoxicity in animals*, Nucleic Acid Research, Vol. 35, No. 2, 687-700 (2007).

The present invention provides certain oligomeric compounds comprising nucleosides having bicyclic sugar moieties with reduced toxicity. In certain embodiments, compounds of the present invention comprising nucleosides having bicyclic sugar moieties and pyrimidine nucleobases without methyl groups at the 5-carbon have reduced toxicity compared to a counterpart oligomeric compound having the same modifications except that the pyrimidines are methylated at the 5-carbon. Thus, in certain embodiments, replacing 5-methyl cytosine and thymine of bicyclic nucleosides with unmodified cytosine and uracil results in oligomeric compounds having decreased toxicity. In certain embodiments, such compounds have reduced potency compared to their methylated counterparts, however, in such embodiments, the loss in potency is typically less than the loss in toxicity. Accordingly, in certain embodiments, such compounds have an improved (increased) therapeutic index. In certain embodiments, compounds have an improved activity to toxicity ratio.

In certain embodiments, compounds comprising bicyclic nucleosides comprising non-methylated pyrimidines are less toxic compared to their methylated counterparts. In certain embodiments, such compounds are less pro-inflammatory. In certain embodiments, such compounds are less immunostimulatory. In certain embodiments, administration of such compounds to an animal results in reduced undesired side-effects. For example, such compounds, in certain embodiments results in reduced or absent enlargement of spleen, injection site reaction, weight loss, inflammation, etc.

In certain embodiments, the present invention envisions using bicyclic nucleosides comprising non-methylated pyrimidine nucleobases in any application for which 5-methylated counterparts have been used. For example, certain oligomeric compounds comprising bicyclic nucleotides with 5-methyl pyrimidines have been advanced as potential therapeutics. In certain embodiments, the present invention provides less toxic counterparts to such oligomeric compounds, wherein such less toxic counterparts are identical to the parent oligomeric compound, except that they lack methyl groups at the 5-positions of the pyrimidines of the bicyclic nucleosides. In certain embodiments, such oligomeric compounds are less toxic than their 5-methyl-pyrimidine counterparts. Thus, the present invention provides compounds with improved toxicity properties.

In certain embodiments, the present invention provides methods for improving the toxic properties of a parent oligomeric compound wherein the parent oligomeric compound comprises at least one bicyclic nucleoside comprising a bicyclic sugar moiety and a 5-methyl pyrimidine. In certain such embodiments the invention provides producing a less toxic counterpart compound that is the same as the parent compound, except that one or more bicyclic nucleobases that comprised a 5-methy pyrimidine in the parent oligomeric compound is replaced with the same pyrimidine lacking the 5-methyl in the less toxic counterpart oligomeric compound.

In certain embodiments, bicyclic nucleosides without 5-methyl modifications on the pyrimidines may be incorporated into oligonucleotides having any chemical motif. Thus, for example, in certain embodiments, the present invention provides oligomeric compounds comprising gapmers, wherein the nucleosides of the wings of the gapmer comprise bicyclic sugar moieties, wherein the nucleobases of those nucleosides are not 5-methyl cytosine or thymine. In such embodiments, the nucleosides of the gap may be modified or unmodified and may include 5-methyl cytosine and/or thymine nucleobases. In certain embodiments, oligomeric compounds of the present invention are fully modified. In certain such embodiments, each nucleoside is a bicyclic nucleoside and none of the nucleobases is a 5-methyl pyrimidine.

In certain embodiments, oligomeric compounds comprise one or more bicyclic nucleoside wherein the sugar bridge is 4'-CH$_2$O-2' and none of the nucleobases of any of those one or more nucleosides is a 5-methyl cytosine or a thymine. In certain embodiments, oligomeric compounds comprise one or more bicyclic nucleoside wherein the sugar bridge is 4'-CH$_2$CH$_2$O-2' and none of the nucleobases of any of those one or more nucleosides is a 5-methyl cytosine or a thymine.

Use of pyrimidine nucleosides modified to include a methyl group at the 5C position improves affinity of antisense compounds to their target. Such modified pyrimidines have not been reported to cause toxicity and have been reported to reduce immune stimulation in mice. Consequently, such nucleosides are routinely used in the antisense art. Incorporation of certain bicyclic nucleosides results in antisense compounds having good affinity and potency. However the therapeutic potential of such compounds is diminished by their toxicity. In certain embodiments of the present invention, it is shown that oligomeric compounds comprising bicyclic nucleosides lacking the standard methyl group at the 5C position of pyrimidines have reduced toxicity. Further, such compounds have no loss or only slight loss in activity and potency. Thus, the therapeutic index of such compounds is improved compared to their counterparts comprising 5-methyl pyrimidine bicyclic nucleosides. In certain embodiments, any parent oligomeric compound comprising one or more bicyclic pyrimidine nucleoside comprising a methyl group at the 5C position can be made less toxic by removal of the 5-methyl. Thus, in certain embodiments, the present invention provides methods of preparing an oligomeric compound having reduced toxicity compared to a parent compound wherein the parent compound comprises at least one 5-methyl pyrimidine bicyclic nucleoside, comprising preparing the same oligomeric compound except that the at least one 5-methyl pyrimidine bicyclic nucleoside is replaced with the same pyrimidine bicyclic nucleoside lacking a 5-methyl.

Compositions and Methods for Formulating Pharmaceutical Compositions

Oligomeric compounds may be admixed with pharmaceutically acceptable active and/or inert substances for the preparation of pharmaceutical compositions or formulations. Compositions and methods for the formulation of pharmaceutical compositions are dependent upon a number of criteria, including, but not limited to, route of administration, extent of disease, or dose to be administered.

Oligomeric compounds, including antisense compounds and/or antidote compounds, can be utilized in pharmaceutical compositions by combining such oligomeric compounds with a suitable pharmaceutically acceptable diluent or carrier. A pharmaceutically acceptable diluent includes phosphate-buffered saline (PBS). PBS is a diluent suitable for use in compositions to be delivered parenterally. Accordingly, in one embodiment, employed in the methods described herein is a pharmaceutical composition comprising an antisense compound and/or antidote compound and a pharmaceutically acceptable diluent. In certain embodiments, the pharmaceutically acceptable diluent is PBS.

Pharmaceutical compositions comprising oligomeric compounds encompass any pharmaceutically acceptable salts, esters, or salts of such esters. In certain embodiments, pharmaceutical compositions comprising oligomeric compounds comprise one or more oligonucleotide which, upon administration to an animal, including a human, is capable of providing (directly or indirectly) the biologically active metabolite or residue thereof. Accordingly, for example, the disclosure is also drawn to pharmaceutically acceptable salts of antisense compounds, prodrugs, pharmaceutically acceptable salts of such prodrugs, and other bioequivalents. Suitable pharmaceutically acceptable salts include, but are not limited to, sodium and potassium salts.

A prodrug can include the incorporation of additional nucleosides at one or both ends of an oligomeric compound which are cleaved by endogenous nucleases within the body, to form the active oligomeric compound.

Nonlimiting Disclosure and Incorporation by Reference

While certain compounds, compositions and methods described herein have been described with specificity in accordance with certain embodiments, the following examples serve only to illustrate the compounds described herein and are not intended to limit the same. Each of the references, GenBank accession numbers, and the like recited in the present application is incorporated herein by reference in its entirety.

The nucleoside sequences set forth in the sequence listing and Examples, are independent of any modification to a sugar moiety, a monomeric linkage, or a nucleobase. As such, oligomeric compounds defined by a SEQ ID NO may comprise, independently, one or more modifications to a sugar moiety, an internucleoside linkage, or a nucleobase. Oligomeric compounds described by Isis Number (Isis NO.) indicate a combination of nucleobase sequence and one or more modifications to a sugar moiety, an internucleoside linkage, or a nucleobase, as indicated.

The sequence listing accompanying this filing provides certain nucleic acid sequences independent of chemical modification. Though that listing identifies each sequence as either "RNA" or "DNA" as required, in reality, those sequences may be modified with any combination of chemical modifications and/or motifs. One of skill in the art will readily appreciate that such designation as "RNA" or "DNA" to describe modified oligonucleotides is, in certain instances, arbitrary. For example, an oligonucleotide comprising a nucleoside comprising a 2'-OH sugar moiety and a thymine base could be described as a DNA having a modified sugar (2'-OH for the natural 2'-H of DNA) or as an RNA having a modified base (thymine (methylated uracil) for natural uracil of RNA).

All publications, patents, and patent applications referenced herein are incorporated by reference. While in the foregoing specification this invention has been described in relation to certain preferred embodiments thereof, and many details have been set forth for purposes of illustration, it will be apparent to those skilled in the art that the invention is susceptible to additional embodiments and that certain of the details described herein may be varied considerably without departing from the basic principles of the invention.

EXAMPLES

Examples (General)

$^1$H and $^{13}$C NMR spectra were recorded on a 300 MHz and 75 MHz Bruker spectrometer, respectively.

Example 1

Synthesis of Nucleoside Phosphoramidites

The preparation of nucleoside phosphoramidites is performed following procedures that are illustrated herein and in the art such as but not limited to U.S. Pat. No. 6,426,220 and published PCT WO 02/36743.

Example 2

Oligonucleoside Synthesis

The oligomeric compounds used in accordance with this invention may be conveniently and routinely made through the well-known technique of solid phase synthesis. Equipment for such synthesis is sold by several vendors including, for example, Applied Biosystems (Foster City, Calif.). Any other means for such synthesis known in the art may additionally or alternatively be employed. It is well known to use similar techniques to prepare oligonucleotides such as the phosphorothioates and alkylated derivatives.

Oligonucleotides: Unsubstituted and substituted phosphodiester (P=O) oligonucleotides can be synthesized on an automated DNA synthesizer (Applied Biosystems model 394) using standard phosphoramidite chemistry with oxidation by iodine.

Phosphorothioates (P=S) are synthesized similar to phosphodiester oligonucleotides with the following exceptions: thiation is effected by utilizing a 10% w/v solution of 3,H-1,2-benzodithiole-3-one 1,1-dioxide in acetonitrile for the oxidation of the phosphite linkages. The thiation reaction step time is increased to 180 sec and preceded by the normal capping step. After cleavage from the CPG column and deblocking in concentrated ammonium hydroxide at 55° C. (12-16 hr), the oligonucleotides are recovered by precipitating with greater than 3 volumes of ethanol from a 1 M NH$_4$OAc solution. Phosphinate oligonucleotides can be prepared as described in U.S. Pat. No. 5,508,270.

Alkyl phosphonate oligonucleotides can be prepared as described in U.S. Pat No. 4,469,863.

3'-Deoxy-3'-methylene phosphonate oligonucleotides can be prepared as described in U.S. Pat. Nos. 5,610,289 or 5,625,050.

Phosphoramidite oligonucleotides can be prepared as described in U.S. Pat. No. 5,256,775 or U.S. Pat. No. 5,366,878.

Alkylphosphonothioate oligonucleotides can be prepared as described in published PCT applications PCT/US94/00902 and PCT/US93/06976 (published as WO 94/17093 and WO 94/02499, respectively).

3'-Deoxy-3'-amino phosphoramidate oligonucleotides can be prepared as described in U.S. Pat. No. 5,476,925.

Phosphotriester oligonucleotides can be prepared as described in U.S. Pat. No. 5,023,243.

Borano phosphate oligonucleotides can be prepared as described in U.S. Pat. Nos. 5,130,302 and 5,177,198.

Oligonucleosides: Methylenemethylimino linked oligonucleosides, also identified as MMI linked oligonucleosides, methylenedimethylhydrazo linked oligonucleosides, also identified as MDH linked oligonucleosides, and methylenecarbonylamino linked oligonucleosides, also identified as amide-3 linked oligonucleosides, and methyleneaminocarbonyl linked oligonucleosides, also identified as amide-4 linked oligonucleosides, as well as mixed backbone oligomeric compounds having, for instance, alternating MMI and P=O or P=S linkages can be prepared as described in U.S. Pat. Nos. 5,378,825, 5,386,023, 5,489,677, 5,602,240 and 5,610,289.

Formacetal and thioformacetal linked oligonucleosides can be prepared as described in U.S. Pat. Nos. 5,264,562 and 5,264,564.

Ethylene oxide linked oligonucleosides can be prepared as described in U.S. Pat. No. 5,223,618.

Example 3

Oligonucleotide Isolation

After cleavage from the controlled pore glass solid support and deblocking in concentrated ammonium hydroxide at 55° C. for 12-16 hours, the oligonucleotides or oligonucleosides are recovered by precipitation out of 1 M NH$_4$OAc with >3 volumes of ethanol. Synthesized oligonucleotides are analyzed by electrospray mass spectroscopy (molecular weight determination) and by capillary gel electrophoresis. The relative amounts of phosphorothioate and phosphodiester linkages obtained in the synthesis is determined by the ratio of correct molecular weight relative to the −16 amu product (+/−32 +/−48). For some studies oligonucleotides are purified by HPLC, as described by Chiang et al., J. Biol. Chem. 1991, 266, 18162-18171. Results obtained with HPLC-purified material are generally similar to those obtained with non-HPLC purified material.

Example 4

Oligonucleotide Synthesis—96 Well Plate Format

Oligonucleotides can be synthesized via solid phase P(III) phosphoramidite chemistry on an automated synthesizer capable of assembling 96 sequences simultaneously in a 96-well format. Phosphodiester internucleotide linkages are afforded by oxidation with aqueous iodine. Phosphorothioate internucleotide linkages are generated by sulfurization utilizing 3,H-1,2 benzodithiole-3-one 1,1 dioxide (Beaucage Reagent) in anhydrous acetonitrile. Standard base-protected beta-cyanoethyl-diiso-propyl phosphoramidites are purchased from commercial vendors (e.g. PE-Applied Biosystems, Foster City, Calif., or Pharmacia, Piscataway, N.J.). Non-standard nucleosides are synthesized as per standard or patented methods. They are utilized as base protected beta-cyanoethyldiisopropyl phosphoramidites.

Oligonucleotides are cleaved from support and deprotected with concentrated $NH_4OH$ at elevated temperature (55-60° C.) for 12-16 hours and the released product then dried in vacuo. The dried product is then re-suspended in sterile water to afford a master plate from which all analytical and test plate samples are then diluted utilizing robotic pipettors.

Example 5

Oligonucleotide Analysis using 96-Well Plate Format

The concentration of oligonucleotide in each well is assessed by dilution of samples and UV absorption spectroscopy. The full-length integrity of the individual products is evaluated by capillary electrophoresis (CE) in either the 96-well format (Beckman P/ACE™ MDQ) or, for individually prepared samples, on a commercial CE apparatus (e.g., Beckman P/ACE™ 5000, ABI 270). Base and backbone composition is confirmed by mass analysis of the oligomeric compounds utilizing electrospray-mass spectroscopy. All assay test plates are diluted from the master plate using single and multi-channel robotic pipettors. Plates are judged to be acceptable if at least 85% of the oligomeric compounds on the plate are at least 85% full length.

Example 6

Cell Culture and Oligonucleotide Treatment

The effect of oligomeric compounds on target nucleic acid expression is tested in any of a variety of cell types provided that the target nucleic acid is present at measurable levels. This can be routinely determined using, for example, PCR or Northern blot analysis. Cell lines derived from multiple tissues and species can be obtained from American Type Culture Collection (ATCC, Manassas, Va.).

The following cell type is provided for illustrative purposes, but other cell types can be routinely used, provided that the target is expressed in the cell type chosen. This can be readily determined by methods routine in the art, for example Northern blot analysis, ribonuclease protection assays or RT-PCR.

b.END cells: The mouse brain endothelial cell line b.END was obtained from Dr. Werner Risau at the Max Plank Institute (Bad Nauheim, Germany). b.END cells were routinely cultured in DMEM, high glucose (Invitrogen Life Technologies, Carlsbad, Calif.) supplemented with 10% fetal bovine serum (Invitrogen Life Technologies, Carlsbad, Calif.). Cells were routinely passaged by trypsinization and dilution when they reached approximately 90% confluence. Cells were seeded into 96-well plates (Falcon-Primaria #353872, BD Biosciences, Bedford, Mass.) at a density of approximately 3000 cells/well for uses including but not limited to oligomeric compound transfection experiments.

Experiments involving treatment of cells with oligomeric compounds:

When cells reach appropriate confluency, they are treated with oligomeric compounds using a transfection method as described.

LIPOFECTIN™

When cells reached 65-75% confluency, they are treated with oligonucleotide. Oligonucleotide is mixed with LIPOFECTIN™ Invitrogen Life Technologies, Carlsbad, Calif.) in Opti-MEM™-1 reduced serum medium (Invitrogen Life Technologies, Carlsbad, Calif.) to achieve the desired concentration of oligonucleotide and a LIPOFECTIN™ concentration of 2.5 or 3 µg/mL per 100 nM oligonucleotide. This transfection mixture is incubated at room temperature for approximately 0.5 hours. For cells grown in 96-well plates, wells are washed once with 100 µL OPTI-MEM™-1 and then treated with 130 µL of the transfection mixture. Cells grown in 24-well plates or other standard tissue culture plates are treated similarly, using appropriate volumes of medium and oligonucleotide. Cells are treated and data are obtained in duplicate or triplicate. After approximately 4-7 hours of treatment at 37° C., the medium containing the transfection mixture is replaced with fresh culture medium. Cells are harvested 16-24 hours after oligonucleotide treatment.

Other suitable transfection reagents known in the art include, but are not limited to, CYTOFECTIN™, LIPOFECTAMINE™, OLIGOFECTAMINE™, and FUGENE™. Other suitable transfection methods known in the art include, but are not limited to, electroporation.

Example 7

Real-Time Quantitative PCR Analysis of Target mRNA Levels

Quantitation of a target mRNA levels was accomplished by real-time quantitative PCR using the ABI PRISM™ 7600, 7700, or 7900 Sequence Detection System (PE-Applied Biosystems, Foster City, Calif.) according to manufacturer's instructions. This is a closed-tube, non-gel-based, fluorescence detection system which allows high-throughput quantitation of polymerase chain reaction (PCR) products in real-time. As opposed to standard PCR in which amplification products are quantitated after the PCR is completed, products in real-time quantitative PCR are quantitated as they accumulate. This is accomplished by including in the PCR reaction an oligonucleotide probe that anneals specifically between the forward and reverse PCR primers, and contains two fluorescent dyes. A reporter dye (e.g., FAM or JOE, obtained from either PE-Applied Biosystems, Foster City, Calif., Operon Technologies Inc., Alameda, Calif. or Integrated DNA Technologies Inc., Coralville, Iowa) is attached to the 5' end of the probe and a quencher dye (e.g., TAMRA, obtained from either PE-Applied Biosystems, Foster City, Calif., Operon Technologies Inc., Alameda, Calif. or Integrated DNA Technologies Inc., Coralville, Iowa) is attached to the 3' end of the probe. When the probe and dyes are intact, reporter dye emission is quenched by the proximity of the 3' quencher dye. During amplification, annealing of the probe to the target sequence creates a substrate that can be cleaved by the 5'-exonuclease activity of Taq polymerase. During the extension phase of the PCR amplification cycle, cleavage of the probe by Taq polymerase releases the reporter dye from the remainder of the probe (and hence from the quencher moiety) and a sequence-specific fluorescent signal is generated. With each cycle, additional reporter dye molecules are cleaved from their respective probes, and the fluorescence intensity is monitored at regular intervals by laser optics built into the ABI PRISM™ Sequence Detection System. In each assay, a series of parallel reactions containing serial dilutions of mRNA from untreated control samples generates a standard curve that is used to quantitate the percent inhibition after antisense oligonucleotide treatment of test samples.

Prior to quantitative PCR analysis, primer-probe sets specific to the target gene being measured are evaluated for their ability to be "multiplexed" with a GAPDH amplification reaction. In multiplexing, both the target gene and the internal standard gene GAPDH are amplified concurrently in a single sample. In this analysis, mRNA isolated from untreated cells is serially diluted. Each dilution is amplified in the presence of primer-probe sets specific for GAPDH only, target gene only ("single-plexing"), or both (multiplexing). Following PCR amplification, standard curves of GAPDH and target mRNA signal as a function of dilution are generated from both the single-plexed and multiplexed samples. If both the slope and correlation coefficient of the GAPDH and target signals generated from the multiplexed samples fall within 10% of their corresponding values generated from the single-plexed samples, the primer-probe set specific for that target is deemed multiplexable. Other methods of PCR are also known in the art.

RT and PCR reagents were obtained from Invitrogen Life Technologies (Carlsbad, Calif.). RT, real-time PCR was carried out by adding 20 μL PCR cocktail (2.5× PCR buffer minus $MgCl_2$, 6.6 mM $MgCl_2$, 375 μM each of dATP, dCTP, dCTP and dGTP, 375 nM each of forward primer and reverse primer, 125 nM of probe, 4 Units RNAse inhibitor, 1.25 Units PLATINUM® Taq, 5 Units MuLV reverse transcriptase, and 2.5× ROX dye) to 96-well plates containing 30 μL total RNA solution (20-200 ng). The RT reaction was carried out by incubation for 30 minutes at 48° C. Following a 10 minute incubation at 95° C. to activate the PLATINUM® Taq, 40 cycles of a two-step PCR protocol were carried out: 95° C. for 15 seconds (denaturation) followed by 60° C. for 1.5 minutes (annealing/extension).

Gene target quantities obtained by RT, real-time PCR are normalized using either the expression level of GAPDH, a gene whose expression is constant, or by quantifying total RNA using RIBOGREEN™ (Molecular Probes, Inc. Eugene, Oreg.). GAPDH expression is quantified by real time RT-PCR, by being run simultaneously with the target, multiplexing, or separately. Total RNA is quantified using RiboGreen™ RNA quantification reagent (Molecular Probes, Inc. Eugene, Oreg.). Methods of RNA quantification by RIBOGREEN™ are taught in Jones, L. J., et al, (Analytical Biochemistry, 1998, 265, 368-374).

In this assay, 170 μL of RIBOGREEN™ working reagent (RIBOGREEN™ reagent diluted 1:350 in 10 mM Tris-HCl, 1 mM EDTA, pH 7.5) is pipetted into a 96-well plate containing 30 μL purified, cellular RNA. The plate is read in a CytoFluor 4000 (PE Applied Biosystems) with excitation at 485 nm and emission at 530 nm.

Example 8

Analysis of Oligonucleotide Inhibition of a Target Expression

Antisense modulation of a target expression can be assayed in a variety of ways known in the art. For example, a target mRNA levels can be quantitated by, e.g., Northern blot analysis, competitive polymerase chain reaction (PCR), or real-time PCR. Real-time quantitative PCR is presently desired. RNA analysis can be performed on total cellular RNA or poly(A)+ mRNA. One method of RNA analysis of the present invention is the use of total cellular RNA as described in other examples herein. Methods of RNA isolation are well known in the art. Northern blot analysis is also routine in the art. Real-time quantitative (PCR) can be conveniently accomplished using the commercially available ABI PRISM™ 7600, 7700, or 7900 Sequence Detection System, available from PE-Applied Biosystems, Foster City, Calif. and used according to manufacturer's instructions.

Protein levels of a target can be quantitated in a variety of ways well known in the art, such as immunoprecipitation, Western blot analysis (immunoblotting), enzyme-linked immunosorbent assay (ELISA) or fluorescence-activated cell sorting (FACS). Antibodies directed to a target can be identified and obtained from a variety of sources, such as the MSRS catalog of antibodies (Aerie Corporation, Birmingham, Mich.), or can be prepared via conventional monoclonal or polyclonal antibody generation methods well known in the art. Methods for preparation of polyclonal antisera are taught in, for example, Ausubel, F. M. et al., *Current Protocols in Molecular Biology*, Volume 2, pp. 11.12.1-11.12.9, John Wiley & Sons, Inc., 1997. Preparation of monoclonal antibodies is taught in, for example, Ausubel, F. M. et al., *Current Protocols in Molecular Biology*, Volume 2, pp. 11.4.1-11.11.5, John Wiley & Sons, Inc., 1997.

Immunoprecipitation methods are standard in the art and can be found at, for example, Ausubel, F. M. et al., *Current Protocols in Molecular Biology*, Volume 2, pp. 10.16.1-10.16.11, John Wiley & Sons, Inc., 1998. Western blot (immunoblot) analysis is standard in the art and can be found at, for example, Ausubel, F. M. et al., *Current Protocols in Molecular Biology*, Volume 2, pp. 10.8.1-10.8.21, John Wiley & Sons, Inc., 1997. Enzyme-linked immunosorbent assays (ELISA) are standard in the art and can be found at, for example, Ausubel, F. M. et al., *Current Protocols in Molecular Biology*, Volume 2, pp. 11.2.1-11.2.22, John Wiley & Sons, Inc., 1991.

Example 9

Design of Phenotypic Assays and in vivo Studies for the use of Target Inhibitors Phenotypic Assays Once target inhibitors have been identified by the methods disclosed herein, the oligomeric compounds are further investigated in one or more phenotypic assays, each having measurable endpoints predictive of efficacy in the treatment of a particular disease state or condition.

Phenotypic assays, kits and reagents for their use are well known to those skilled in the art and are herein used to investigate the role and/or association of a target in health and disease. Representative phenotypic assays, which can be purchased from any one of several commercial vendors, include those for determining cell viability, cytotoxicity, proliferation or cell survival (Molecular Probes, Eugene, Oreg.; PerkinElmer, Boston, Mass.), protein-based assays including enzymatic assays (Panvera, LLC, Madison, Wis.; BD Biosciences, Franklin Lakes, N.J.; Oncogene Research Products, San Diego, Calif.), cell regulation, signal transduction, inflammation, oxidative processes and apoptosis (Assay Designs Inc., Ann Arbor, Mich.), triglyceride accumulation (Sigma-Aldrich, St. Louis, Mo.), angiogenesis assays, tube formation assays, cytokine and hormone assays and metabolic assays (Chemicon International Inc., Temecula, Calif.; Amersham Biosciences, Piscataway, N.J.).

In one non-limiting example, cells determined to be appropriate for a particular phenotypic assay (i.e., MCF-7 cells selected for breast cancer studies; adipocytes for obesity studies) are treated with a target inhibitors identified from the in vitro studies as well as control compounds at optimal concentrations which are determined by the methods described above. At the end of the treatment period, treated and untreated cells are analyzed by one or more methods specific for the assay to determine phenotypic outcomes and endpoints.

Phenotypic endpoints include changes in cell morphology over time or treatment dose as well as changes in levels of cellular components such as proteins, lipids, nucleic acids, hormones, saccharides or metals. Measurements of cellular status which include pH, stage of the cell cycle, intake or excretion of biological indicators by the cell, are also endpoints of interest.

Measurement of the expression of one or more of the genes of the cell after treatment is also used as an indicator of the efficacy or potency of the a target inhibitors. Hallmark genes, or those genes suspected to be associated with a specific disease state, condition, or phenotype, are measured in both treated and untreated cells.

In vivo Studies

The individual subjects of the in vivo studies described herein are warm-blooded vertebrate animals, which includes humans.

Example 10

RNA Isolation

Poly(A)+ mRNA Isolation

Poly(A)+ mRNA is isolated according to Miura et al., (Clin. Chem., 1996, 42, 1758-1764). Other methods for poly (A)+ mRNA isolation are routine in the art. Briefly, for cells grown on 96-well plates, growth medium is removed from the cells and each well is washed with 200 µL cold PBS. 60 µL lysis buffer (10 mM Tris-HCl, pH 7.6, 1 mM EDTA, 0.5 M NaCl, 0.5% NP-40, 20 mM vanadyl-ribonucleoside complex) is added to each well, the plate is gently agitated and then incubated at room temperature for five minutes. 55 µL of lysate is transferred to Oligo d(T) coated 96-well plates (AGCT Inc., Irvine Calif.). Plates are incubated for 60 minutes at room temperature, washed 3 times with 200 µL of wash buffer (10 mM Tris-HCl pH 7.6, 1 mM EDTA, 0.3 M NaCl). After the final wash, the plate is blotted on paper towels to remove excess wash buffer and then air-dried for 5 minutes. 60 µL of elution buffer (5 mM Tris-HCl pH 7.6), preheated to 70° C., is added to each well, the plate is incubated on a 90° C. hot plate for 5 minutes, and the eluate is then transferred to a fresh 96-well plate.

Cells grown on 100 mm or other standard plates may be treated similarly, using appropriate volumes of all solutions.

Total RNA Isolation

Total RNA is isolated using an RNEASY 96™ kit and buffers purchased from Qiagen Inc. (Valencia, Calif.) following the manufacturer's recommended procedures. Briefly, for cells grown on 96-well plates, growth medium is removed from the cells and each well is washed with 200 µL cold PBS. 150 µL Buffer RLT is added to each well and the plate vigorously agitated for 20 seconds. 150 µL of 70% ethanol is then added to each well and the contents mixed by pipetting three times up and down. The samples are then transferred to the RNEASY 96™ well plate attached to a QIAVAC™ manifold fitted with a waste collection tray and attached to a vacuum source. Vacuum is applied for 1 minute. 500 µL of Buffer RW1 is added to each well of the RNEASY 96™ plate and incubated for 15 minutes and the vacuum is again applied for 1 minute. An additional 500 µL of Buffer RW1 is added to each well of the RNEASY 96™ plate and the vacuum is applied for 2 minutes. 1 mL of Buffer RPE is then added to each well of the RNEASY 96™ plate and the vacuum applied for a period of 90 seconds. The Buffer RPE wash is then repeated and the vacuum is applied for an additional 3 minutes. The plate is then removed from the QIAVAC™ manifold and blotted dry on paper towels. The plate is then re-attached to the QIAVAC™ manifold fitted with a collection tube rack containing 1.2 mL collection tubes. RNA is then eluted by pipetting 140 µL of RNAse free water into each well, incubating 1 minute, and then applying the vacuum for 3 minutes.

The repetitive pipetting and elution steps may be automated using a QIAGEN Bio-Robot 9604 (Qiagen, Inc., Valencia Calif.). Essentially, after lysing of the cells on the culture plate, the plate is transferred to the robot deck where the pipetting, DNase treatment and elution steps are carried out.

Example 11

Target-Specific Primers and Probes

Probes and primers may be designed to hybridize to a target sequence, using published sequence information.

For example, for human PTEN, the following primer-probe set was designed using published sequence information (GENBANK™ accession number U92436.1, SEQ ID NO: 1).

Forward primer: AATGGCTAAGTGAAGATGACAAT-CAT (SEQ ID NO: 2)

Reverse primer: TGCACATATCATTACACCAGTTCGT (SEQ ID NO: 3) And the PCR probe:

FAM-TTGCAGCAATTCACTGTAAAGCTG-GAAAGG-TAMRA (SEQ ID NO: 4), where FAM is the fluorescent dye and TAMRA is the quencher dye.

Example 12

Western Blot Analysis of Target Protein Levels

Western blot analysis (immunoblot analysis) is carried out using standard methods. Cells are harvested 16-20 h after oligonucleotide treatment, washed once with PBS, suspended in Laemmli buffer (100 µl/well), boiled for 5 minutes and loaded on a 16% SDS-PAGE gel. Gels are run for 1.5 hours at 150 V, and transferred to membrane for western blotting. Appropriate primary antibody directed to a target is used, with a radiolabeled or fluorescently labeled secondary antibody directed against the primary antibody species. Bands are visualized using a PHOSPHORIMAGER™ (Molecular Dynamics, Sunnyvale Calif.).

Example 13

4'-CH$_2$—O-2' BNA Gapped Oligomeric Compounds Targeted to PTEN: in vivo Study

In accordance with the present invention, oligomeric compounds were synthesized and tested for their ability to reduce PTEN expression in vivo at doses of 20 and 60 mg/kg. Six week old male Balb/c mice (Jackson Laboratory, Bar Harbor, Me.) were administered a single intraperitoneal (i.p) injection at either 20 or 60 mg/kg of 4'-CH$_2$—O-2' BNA 2-10-2 gapped oligomers (3920 and 392745). The 4'-CH$_2$—O-2' BNA gapped oligomer, 392745, contains non-methylated pyrimidine in the wings. The 4'-CH$_2$—O-2' BNA gapped oligomer, 392063, contains methylated pyrimidine in the wings (i.e. each cytosine residues in the 4'-CH$_2$—O-2' BNA wings of 392745 are replaced with 5-methylcytosines, while the thymidine residues in the 4'-CH$_2$—O-2' BNA wings of 392745 are replaced with 5-methyl thymidines). All internucleoside linkages are phosphorothioates, nucleosides not followed by a subscript are βD-2'-deoxyribonucleosides, nucleosides followed by a subscript 1 are 4'-CH$_2$—O-2' modified bicyclic nucleosides and $^{Me}$C indicates a 5'-methyl cytosine nucleoside.

| SEQ ID NO./ ISIS NO. | Composition (5' to 3') | Wing Chemistry |
|---|---|---|
| 5/392745 | C$_1$U$_1$TAGCACTGGCC$_1$U$_1$ | 4'-CH$_2$—O-2' BNA (U/C) |
| 6/392063 | $^{Me}$C$_1$T$_1$TAGCACTGGC$^{Me}$C$_1$T$_1$4'-CH$_2$—O-2' BNA (T/$^{Me}$C) |

Each dose group consisted of four animals. The mice were sacrificed 72 hours following the final administration to determine the PTEN mRNA levels in liver using real-time PCR and RIBOGREEN® RNA quantification reagent (Molecular Probes, Inc. Eugene, Oreg.) according to standard protocols. PTEN mRNA levels were determined relative to total RNA (using Ribogreen), prior to normalization to saline-treated control. Results are listed below as the average % inhibition of mRNA expression for each treatment group, normalized to saline-injected control. Resulting dose-response curves were used to determine the IC$_{50}$. Tm's were assessed in 100 mM phosphate buffer, 0.1 mM EDTA, pH 7, at 260 nm using 4 μM modified oligomers and 4 μM complementary RNA. The activities are listed below.

| SEQ ID NO./ ISIS NO. | Dose (mg/kg) | % inhibition | IC50 (nM) | Tm (° C.) |
|---|---|---|---|---|
| 6/392063 | 20 | 86 | 5.8 | 60.5 |
| | 60 | 92 | | |
| 5/392745 | 20 | 89 | 6.8; 6.2 | 58.6 |
| | 60 | 92 | | |

Liver transaminase levels, alanine aminotranferease (ALT) and aspartate aminotransferase (AST), in serum were also measured relative to saline injected mice. Increases in the transaminase levels can indicate hepatotoxicity. The transaminase levels measured for mice treated with the 2-10-2 gapped oligomers comprising LNA nucleosides (both 392063 and 392745) at lower doses (20 mg/kg) were not elevated to a level indicative of hepatotoxicity with respect to saline treated control. Treatment with 60 mg/kg does of 392063 substantially increased ALT and AST levels. The ALT and AST levels measured for mice treated with 60 mg/kg does of 392745 were decreased about 4.5-fold and 3 fold as compared to 392063 treatment. The approximate liver transaminase levels are listed below.

| SEQ ID NO./ ISIS NO. | Dose (mg/kg) | AST (IU/L) | ALT (IU/L) |
|---|---|---|---|
| saline | n/a | 68 | 24 |
| 6/392063 | 20 | 56 | 28 |
| | 60 | 598 | 489 |
| 5/392745 | 20 | 81 | 29 |
| | 60 | 202 | 108 |

The effects on liver, kidney, spleen weights and body weight gain were also determined. Approximate average tissue weights and body weight gain for each treatment group are presented in the table below. As show, treatment with the 2-10-2 gapped oligomers comprising LNA nucleosides (both 392063 and 392745) did not substantially alter liver, kidney, spleen weights or body weight gain in normal mice as compared to the organ weights of mice treated with saline alone.

| SEQ ID NO./ ISIS NO. | Dose (mg/kg) | Liver | Kidney | Spleen | Body weight gain |
|---|---|---|---|---|---|
| Saline | | 1.00 | 1.00 | 1.00 | 1.05 |
| 6/392063 | 20 | 1.22 | 1.02 | 0.99 | 1.05 |
| | 60 | 1.29 | 1.00 | 1.11 | 0.99 |
| 5/392745 | 20 | 1.22 | 1.02 | 1.14 | 1.06 |
| | 60 | 1.25 | 1.02 | 1.12 | 1.01 |

Example 14

4'-CH$_2$—O-2', 4'-CH$_2$CH$_2$—O-2' BNA 2-10-2 Gapped Oligomeric Compounds Targeted to PTEN: in vivo Study Six week old male Balb/c mice (Jackson Laboratory, Bar Harbor, Me.) were administered a single intraperitoneal (i.p) injection with 4'-CH$_2$—O-2' BNA containing oligomers (392745 and 392063) and 6(S)-4'-CH(CH$_3$)—O-2' BNA containing oligomers (392749 and 411847) at a does of 3.2, 10, 32, 66 and 100 mg/kg. Oligomers 392063 and 411847 contain LNA nucleosides with methylated pyrimidines, and oligomers 392745 and 392749 contain LNA nucleosides with non-methylated pyrimidines in the wings. All internucleoside linkages are phosphorothioates, nucleosides not followed by a subscript are βD-2'-deoxyribonucleosides, nucleosides followed by a subscript 1 are 4'-CH$_2$—O-2' modified bicyclic nucleosides, nucleosides followed by a subscript S are 6(S)-4'-CH(CH$_3$)—O-2' modified bicyclic nucleosides wherein S indicates the configuration at the 6 carbon atom and $^{Me}$C indicates a 5'-methyl cytosine nucleoside.

| SEQ ID NO./ ISIS NO. | Composition (5' to 3') | Wing Chemistry |
|---|---|---|
| 5/392745 | $C_I U_I$TAGCACTGGCC$_I U_I$ | 4'-$CH_2$—O—2' BNA (U/C) |
| 6/392063 | $^{Me}C_I T_I$TAGCACTGGC$^{Me}C_I T_I$ | 4'-$CH_2$—O—2' BNA (T/$^{Me}$C) |
| 5/392749 | $C_S U_S$TAGCACTGGCC$_S U_S$ | 6(S)—$CH_2$—O—$CH_3$ BNA (U/C) |
| 6/411847 | $^{Me}C_S T_S$TAGCACTGGC$^{Me}C_S T_S$ | 6(S)—$CH_2$—O—$CH_3$ BNA (T/$^{Me}$C) |

Each dose group consisted of four animals. The mice were sacrificed 72 hours following the final administration to determine the PTEN mRNA levels in liver using real-time PCR and RIBOGREEN® RNA quantification reagent (Molecular Probes, Inc. Eugene, Oreg.) according to standard protocols. PTEN mRNA levels were determined relative to total RNA (using Ribogreen), prior to normalization to saline-treated control. Results are listed below as the average % inhibition of mRNA expression for each treatment group, normalized to saline-injected control.

| SEQ ID NO./ ISIS NO. | PTEN mRNA levels (% inhibition) | | | | |
|---|---|---|---|---|---|
| | 3.2 mg/kg | 10 mg/kg | 32 mg/kg | 66 mg/kg | 100 mg/kg |
| 5/392745 | 0 | 58 | 90 | 90 | 93 |
| 6/392063 | 0 | 68 | 88 | 90 | 91 |
| 7/392749 | 14 | 20 | 81 | 92 | 93 |
| 8/411847 | 0 | 32 | 87 | 84 | 92 |

Estimated $ED_{50}$ concentrations for each oligomers were calculated using Graphpad Prism. $ED_{50}$ is the dose at which 50% mRNA reduction is observed.

| SEQ ID NO./ ISIS NO. | $ED_{50}$ |
|---|---|
| 5/392745 | 9 |
| 6/392063 | 8 |
| 5/392749 | 15 |
| 6/411847 | 12 |

Liver transaminase levels, alanine aminotranferease (ALT) and aspartate aminotransferase (AST), in serum were also measured relative to saline injected mice. Increases in the transaminase levels can indicate hepatotoxicity. The approximate liver transaminase levels are listed below.

| SEQ ID NO./ ISIS NO. | ALT levels (IU/L) | | | | |
|---|---|---|---|---|---|
| | 3.2 mg/kg | 10 mg/kg | 32 mg/kg | 66 mg/kg | 100 mg/kg |
| 5/392745 | 30 | 20 | 13 | 59 | 3842 |
| 6/392063 | 20 | 17 | 20 | 4292 | 13811 |
| 5/392749 | 18 | 24 | 14 | 18 | 33 |
| 6/411847 | 26 | 27 | 16 | 279 | 2816 |
| Saline | | | ALT = 24 IU/L | | |

Similar to the results indicated in the previous example, treatment with higher doses (66 mg/kg and 100 mg/kg) of 4'-$CH_2$—O-2'BNA 2-10-2 gapped oligomer 392063 substantially increased ALT levels. Treatment with lower doses (3.2, 10, 32 and 66 mg/kg) of 392745 were not elevated to a level indicative of hepatotoxicity with respect to saline treated control. Treatment with the higher doses (100 mg/kg) of 392745 decreased the ALT levels about 3.5-fold as compared to 392063 treatment. Treatment with 6(S)-4'-CH($CH_3$)—O-2' BNA 2-10-2 gapped oligomer 411847 decreased the ALT levels about 5-fold as compared to 392063 treatment. The measured ALT levels at all doses amounts for mice treated with 6(S)-4'-CH($CH_3$)—O-2' BNA 2-10-2 gapped oligomer 392749 were not elevated to a level indicative of hepatotoxicity.

This example compared parent gapmer compounds comprising bicyclic nucleosides with 5-metyl pyrimidines in the wings with counterpart compounds that were identical, except that they lacked the 5-methyl on the pyrimidines of the bicyclic nucleosides. The counterpart compounds lacking 5-methyl modifications on the pyrimidines were dramatically less toxic than the parent compounds with 5-methyl pyrimidines as measured by ALT levels. Potency of the parent compounds and the less toxic counterparts were similar.

Example 15

BNA 2-10-2 Gapped Oligomeric Compounds Targeted to PTEN: in vivo Study

Six week old male Balb/c mice (Jackson Laboratory, Bar Harbor, Me.) were administered a single intraperitoneal (i.p) injection of oligomers as set forth in the table below.

| SEQ ID NO./ ISIS NO. | Composition (5' to 3') | Wing Chemistry |
|---|---|---|
| 5/396006 | $C_{as}$ $U_{as}$ $T_{ds}$ $A_{ds}$ $G_{ds}$ $C_{ds}$ $A_{ds}$ $C_{ds}$ $T_{ds}$ $G_{ds}$ $G_{ds}$ $C_{ds}$ $C_{as}$ $U_a$ | α-L-LNA (C/U) |
| 6/435854 | $^m C_{as}$ $T_{as}$ $T_{ds}$ $A_{ds}$ $G_{ds}$ $C_{ds}$ $A_{ds}$ $C_{ds}$ $T_{ds}$ $G_{ds}$ $G_{ds}$ $C_{ds}$ $^m C_{as}$ $T_a$ | α-L-LNA ($^{me}$C/T) |

Subscript key: a = α-L-LNA; d = 2'-deoxy; s = phosphorothioate linkage

Mice were divided into 9 groups, with 4 mice in each group. The mice of 8 groups received a single dose, administered i.p., of one of the above oligomeric compounds at a dose of 100, 32, 10, or 3.2 mg/kg. The final group was dosed with phosphate buffered saline (PBS) as a control. The mice were sacrificed 72 hours after administration. Antisense activity was determined by measuring PTEN RNA in liver. The average of each of oligomer-treated group, expressed as % reduction compared to the PBS control group, is provided in the table below.

| ISIS NO | Wing bases | Dose (mg/kg) | % Reduction PTEN RNA |
|---|---|---|---|
| 396006 | C/U | 100 | 97 |
|  |  | 32 | 95 |
|  |  | 10 | 77 |
|  |  | 3.2 | 47 |
| 435854 | $^{me}$C/T | 100 | 95 |
|  |  | 32 | 94 |
|  |  | 10 | 73 |
|  |  | 3.2 | 48 |

These oligomers showed very similar PTEN RNA antisense activity in liver.

Serum ALT was measured for each animal and is provided in the table below.

| ISIS NO | Wing bases | Dose (mg/kg) | ALT levels (IU/L) - Individual animals | | | |
|---|---|---|---|---|---|---|
| PBS | NA | 0 | 16 | 23 | 20 | 18 |
| 396006 | C/U | 100 | 28 | 23 | 23 | 28 |
|  |  | 32 | 24 | 19 | 15 | 23 |
|  |  | 10 | 18 | 22 | 19 | 20 |
|  |  | 3.2 | 27 | 19 | 17 | 24 |
| 435854 | $^{me}$C/T | 100 | 1575 | 854 | 1665 | 3948 |
|  |  | 32 | 24 | 29 | 16 | 46 |
|  |  | 10 | 23 | 21 | 33 | 28 |
|  |  | 3.2 | 15 | 22 | 20 | 11 |

Serum ALT was elevated at the highest dose of ISIS 43584, which includes methylated pyrimidines on bicylcic nucleosides.

Body weight was measured before treatment and again at sacrifice 72 hours after treatment. Average body weight for each group at sacrifice relative to pre-dose body weight is reported in the table below.

| ISIS NO | Wing bases | Dose (mg/kg) | % of pre-dose weight |
|---|---|---|---|
| PBS | NA | 0 | 99 |
| 396006 | C/U | 100 | 100 |
|  |  | 32 | 101 |
|  |  | 10 | 101 |
|  |  | 3.2 | 100 |
| 435854 | $^{me}$C/T | 100 | 94 |
|  |  | 32 | 102 |
|  |  | 10 | 102 |
|  |  | 3.2 | 99 |

The highest dose of ISIS 435854 shows some weight loss.

Spleens were weighed as a measure of inflammatory response. Average spleen weight for each treatment group relative to PBS control is provided in the table below.

| ISIS NO | Wing bases | Dose (mg/kg) | % control |
|---|---|---|---|
| PBS | NA | 0 | 100 |
| 396006 | C/U | 100 | 120 |
|  |  | 32 | 97 |
|  |  | 10 | 100 |
|  |  | 3.2 | 95 |
| 435854 | $^{me}$C/T | 100 | 160 |
|  |  | 32 | 115 |
|  |  | 10 | 87 |
|  |  | 3.2 | 112 |

Treatment with ISIS 43584, which comprises bicyclic nucleosides having methylated pyrimidines had a marked increase in spleen weight compared to control and compared to the same compound with non-methylated pyrimidine bicyclic nucleosides. This suggests that the removal of the 5-methyl of the pyrimidine results in a less pro-inflammatory oligomer.

Example 16

BNA 2-10-2 Gapped Oligomeric Compounds Targeted to PTEN: in vivo Study

Six week old male Balb/c mice (Jackson Laboratory, Bar Harbor, Me.) were administered a single intraperitoneal (i.p) injection of oligomers as set forth in the table below.

| SEQ ID NO./ ISIS NO. | Composition (5' to 3') | Wing Chemistry |
|---|---|---|
| 5/443393 | $C_{js} U_{os} T_{ds} A_{ds} G_{ds} C_{ds} A_{ds} C_{ds} T_{ds} G_{ds} G_{ds} C_{ds} C_{js} U_j$ | U/C ENA |
| 6/443394 | $^mC_{js} T_{js} T_{ds} A_{ds} G_{ds} C_{ds} A_{ds} C_{ds} T_{ds} G_{ds} G_{ds} C_{ds}\ ^mC_{js} T_j$ | T/$^m$C ENA |
| 5/445544 | $C_{xs} U_{xs} T_{ds} A_{ds} G_{ds} C_{ds} A_{ds} C_{ds} T_{ds} G_{ds} G_{ds} C_{ds} C_{xs} U_x$ | U/C 2'-S-LNA |
| 6/445545 | $^mC_{xs} T_{xs} T_{ds} A_{ds} G_{ds} C_{ds} A_{ds} C_{ds} T_{ds} G_{ds} G_{ds} C_{ds}\ ^mC_{xs} T_x$ | T/$^m$C 2'-S-LNA |

Subscript key: x = S-LNA; j = ENA; k = constrained ethyl BNA; d = 2'-deoxy; s = phosphorothioate linkage Mice were divided into 17 groups, with 4 mice in each group. The mice of 16 groups received a single dose, administered i.p., of one of the above oligomeric compounds at a dose of 100, 32, 10, or 3.2 mg/kg. The final group was dosed with phosphate buffered saline (PBS) as a control. The mice were sacrificed 72 hours after administration. Antisense activity was determined by measuring PTEN RNA in liver and is expressed as % reduction compared to PBS control mice. The results are summarized in the table below.

| ISIS NO | Wings Chem | Dose (mg/kg) | % Reduction PTEN RNA | ED$_{50}$ (mg/kg) |
|---|---|---|---|---|
| 443393 | U/C ENA | 100 | 91 | 16.2 |
| | | 32 | 64 | |
| | | 10 | 35 | |
| | | 3.2 | 10 | |
| 443394 | T/$^m$C ENA | 100 | 89 | 13.5 |
| | | 32 | 68 | |
| | | 10 | 39 | |
| | | 3.2 | 16 | |
| 445544 | U/C 2'-S-LNA | 100 | 95 | 4.9 |
| | | 32 | 93 | |
| | | 10 | 72 | |
| | | 3.2 | 31 | |
| 445545 | T/$^m$C 2'-S-LNA | 100 | 92 | 7.7 |
| | | 32 | 87 | |
| | | 10 | 55 | |
| | | 3.2 | 21 | |

Each of the oligomers reduced PTEN RNA in liver.

Toxicity was assessed by measuring alanine aminotranferease (ALT) in serum. Results for each animal are provided below.

| ISIS NO | Wings Chem | Dose (mg/kg) | ALT levels (IU/L) - Individual animals | | | |
|---|---|---|---|---|---|---|
| PBS | NA | 0 | 34 | 25 | 33 | 32 |
| 443393 | U/C ENA | 100 | 16 | 22 | 42 | 23 |
| | | 32 | 21 | 24 | 53 | 53 |
| | | 10 | 26 | 33 | 30 | 29 |
| | | 3.2 | 19 | 36 | 83 | 20 |
| 443394 | T/$^m$C ENA | 100 | 23 | 44 | 18 | 23 |
| | | 32 | 55 | 25 | 28 | 25 |
| | | 10 | 55 | 28 | 32 | 32 |
| | | 3.2 | 28 | 26 | 30 | 69 |
| 445544 | U/C 2'-S-LNA | 100 | 977 | 1061 | 88 | 133 |
| | | 32 | 23 | 38 | 19 | 22 |
| | | 10 | 23 | 33 | 20 | 36 |
| | | 3.2 | 21 | 28 | 30 | 36 |
| 445545 | T/$^m$C 2'-S-LNA | 100 | 102 | 135 | 277 | 85 |
| | | 32 | 22 | 45 | 24 | 47 |
| | | 10 | 79 | 19 | 28 | 18 |
| | | 3.2 | 20 | 34 | 31 | 34 |

In this example, ALT was not elevated in either of the ENA groups, whether or not the ENA-pyrimidines included a 5-methyl. Two animals treated with 2'-S-LNA having non-methylated pyrimidines had considerably elevated ALT, while the other two animals had only mild elevation. The methylated counterpart showed mild ALT elevation.

Body weight was measured before treatment and again at sacrifice 72 hours after treatment. Average body weight for each group at sacrifice relative to pre-dose body weight is reported in the table below.

| ISIS NO | Wings Chem | Dose (mg/kg) | % pre-dose wt |
|---|---|---|---|
| PBS | NA | 0 | 102 |
| 443393 | U/C ENA | 100 | 98 |
| | | 32 | 99 |
| | | 10 | 104 |
| | | 3.2 | 101 |
| 443394 | T/$^m$C ENA | 100 | 101 |
| | | 32 | 101 |
| | | 10 | 102 |
| | | 3.2 | 102 |
| 445544 | U/C 2'-S-LNA | 100 | 98 |
| | | 32 | 102 |
| | | 10 | 101 |
| | | 3.2 | 103 |
| 445545 | T/$^m$C 2'-S-LNA | 100 | 102 |
| | | 32 | 101 |
| | | 10 | 102 |
| | | 3.2 | 100 |

Spleens were weighed as a measure of inflammatory response. Average spleen weight for each treatment group relative to PBS control is provided in the table below.

| ISIS NO | Wings Chem | Dose (mg/kg) | % Control |
|---|---|---|---|
| PBS | NA | 0 | 100 |
| 443393 | U/C ENA | 100 | 96 |
| | | 32 | 110 |
| | | 10 | 96 |
| | | 3.2 | 89 |
| 443394 | T/$^m$C ENA | 100 | 98 |
| | | 32 | 97 |
| | | 10 | 96 |
| | | 3.2 | 106 |
| 445544 | U/C 2'-S-LNA | 100 | 109 |
| | | 32 | 101 |
| | | 10 | 92 |
| | | 3.2 | 98 |
| 445545 | T/$^m$C 2'-S-LNA | 100 | 139 |
| | | 32 | 134 |
| | | 10 | 99 |
| | | 3.2 | 100 |

Treatment with ISIS445545, which comprises bicyclic nucleosides having methylated pyrimidines had an increase in spleen weight compared to control and compared to the same compound with non-methylated pyrimidine bicyclic nucleosides. This suggests that the removal of the 5-methyl of the pyrimidine results in a less pro-inflammatory oligomer.

The invention claimed is:

1. A method comprising administering to an animal an oligomeric compound comprising an oligonucleotide consisting of 15-26 linked nucleosides wherein the oligonucleotide is a gapmer, wherein each wing of the gapmer consists of 1-5 linked nucleosides and at least one nucleoside of at least one wing is a bicyclic nucleoside comprising a bicyclic sugar moiety and a nucleobase selected from among Formula I and Formula II:

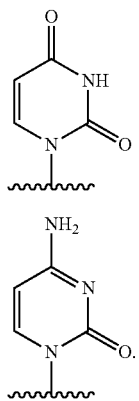

2. The method of claim 1, wherein the at least one bicyclic nucleoside has a bicyclic sugar moiety having Formula III:

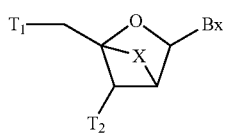

wherein independently for each of the at least one bicyclic nucleoside of formula III:

X is selected from among: 4'-(CR$_1$R$_2$)$_n$—Y-2';

wherein each R$_1$ and each R$_2$ is independently selected from among: hydrogen, a halogen, an optionally substituted C$_1$-C$_6$ alkyl, an optionally substituted C$_2$-C$_6$ alkenyl, an optionally substituted C$_2$-C$_6$ alkynyl, an optionally substituted heteroalkyl, an optionally substituted heteroalkenyl, and an optionally substituted heteroalkynyl;

Y is selected from among CR$_1$R$_2$, O, N(J), and S;

T$_1$ and T$_2$ are each, independently, an internucleoside linking group linking the bicyclic nucleoside to the oligonucleotide or one of T$_1$ and T$_2$ is an internucleoside linking group linking the bicyclic nucleoside to the oligonucleotide and the other of T$_1$ and T$_2$ is hydroxyl, a protected hydroxyl, a linked conjugate group or a 5' or 3'-terminal group;

n is from 1 to 3;

J is hydrogen, a halogen, an optionally substituted C$_1$-C$_5$ alkyl, an optionally substituted C$_2$-C$_5$ alkenyl, an optionally substituted C$_2$-C$_5$ alkynyl, an optionally substituted heteroalkyl, an optionally substituted heteroalkenyl, or an optionally substituted heteroalkynyl; and Bx is the nucleobase of Formula I or Formula II.

3. The method of claim 2, wherein the oligonucleotide comprises at least one modified non-bicyclic nucleoside.

4. The method of claim 2, wherein the oligonucleotide comprises at least one bicyclic nucleoside of Formula III in each wing of the gapmer.

5. The method of claim 2, wherein at least one wing of the gapmer consists of 1-3 linked nucleosides.

6. The method of claim 1, wherein the oligonucleotide comprises at least one modified internucleoside linkage.

7. The method of claim 2, wherein the oligonucleotide is an antisense compound.

8. The method of claim 7, wherein the oligonucleotide is complementary to a target nucleic acid selected from among: target mRNA, target pre-mRNA, target microRNA, and a target non-coding RNA.

9. The method of claim 8 wherein the oligomeric compound has an activity to toxicity ratio of greater than 5 when tested in an animal.

10. The method of claim 9 comprising assessing toxicity in the animal, wherein the assessing toxicity comprises measuring the concentration of one or more liver transaminase in the serum of the animal.

11. An oligonucleotide of Formula:
5'-LDLDDLLDDLDLDLL-3' wherein, each L is a bicylcic nucleoside comprising a bicyclic sugar moiety and a nucleobase, wherein none of the nucleobases of the L nucleosides has the structure of Formula IV or Formula V:

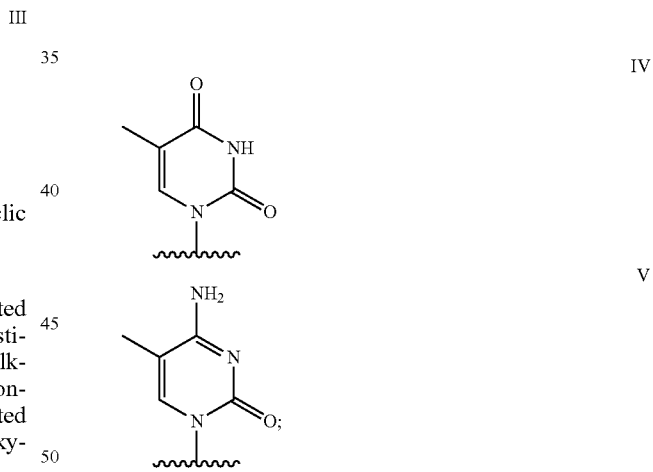

and wherein each D is an unmodified deoxynucleoside.

12. The oligonucleotide of claim 11, wherein the sugar moiety of each L nucleoside comprises a 4'-2' bridge having the formula: 4'-CH$_2$O-2'.

13. The method of claim 2, wherein the oligonucleotide has the formula:

$$5'\text{-}(L)_{1\text{-}5}(D)_{6\text{-}18}(L)_{1\text{-}5}\text{-}3'$$

wherein, each L is a bicylcic nucleoside comprising a bicyclic sugar moiety and a nucleobase, wherein none of the nucleobases of the L nucleosides has the structure of Formula IV or Formula V:

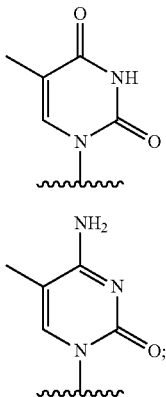

and wherein each D is an unmodified deoxynucleoside.

14. A method of producing a compound having reduced toxicity when compared to a parent compound wherein the parent compound comprises at least one bicyclic nucleoside comprising a 5-methylpyrimidine, comprising:
preparing a compound wherein at least one bicyclic nucleoside comprising a 5-methyl pyrimidine in the parent is instead a bicyclic nucleoside comprising an unmodified pyrimidine; and
thereby producing a compound having reduced toxicity compared to the parent compound.

15. A method of treating a disease or condition in an animal comprising:
administering to the animal an oligomeric compound, wherein the oligomeric compound comprises an oligonucleotide, wherein the oligonucleotide is a gapmer, wherein the wings of the gapmer comprise bicyclic nucleosides wherein none of the bicyclic nucleosides comprises a pyrimidine nucleobase comprising a methyl group at the 5-position; and
thereby treating the disease or condition in the animal.

* * * * *